US012782350B2

(12) United States Patent
Hellmich-Duong et al.

(10) Patent No.: US 12,782,350 B2
(45) Date of Patent: Nov. 3, 2026

(54) MACHINE READABLE DIAGNOSTIC TEST DEVICES AND METHODS AND APPARATUS TO MAKE AND/OR PROCESS THE SAME

(71) Applicant: Abbott Rapid Diagnostics International Unlimited Company, Dublin (IE)

(72) Inventors: Thanh Tu Hellmich-Duong, Jena (DE); Thomas Uhlig, Jena (DE); Carsten Buenning, Gross-Rohrheim (DE); Thomas Ullrich, Jena (DE); Stefan Kügler, Jena (DE); Heidi Klemm, Jena (DE); Chris Smit, Berkshire (GB)

(73) Assignee: Abbott Rapid Diagnostics International Unlimited Company, Dublin (IE)

( * ) Notice: Subject to any disclaimer, the term of this patent is extended or adjusted under 35 U.S.C. 154(b) by 849 days.

(21) Appl. No.: 17/928,188

(22) PCT Filed: May 31, 2021

(86) PCT No.: PCT/EP2021/064581
§ 371 (c)(1),
(2) Date: Nov. 28, 2022

(87) PCT Pub. No.: WO2021/240020
PCT Pub. Date: Dec. 2, 2021

(65) Prior Publication Data
US 2023/0221312 A1 Jul. 13, 2023

Related U.S. Application Data

(60) Provisional application No. 63/129,375, filed on Dec. 22, 2020, provisional application No. 63/032,093, filed on May 29, 2020.

(51) Int. Cl.
*G01N 33/543* (2006.01)
*G01N 15/01* (2024.01)
(Continued)

(52) U.S. Cl.
CPC ... *G01N 33/54388* (2021.08); *G01N 33/5438* (2013.01); *G01N 33/549* (2013.01); *G01N 33/581* (2013.01); *G01N 15/01* (2024.01)

(58) Field of Classification Search
CPC ......... G01N 33/54388; G01N 33/5438; G01N 33/549; G01N 33/581; G01N 15/01;
(Continued)

(56) References Cited

U.S. PATENT DOCUMENTS 3,714,056 A 1/1973 Tallent
4,095,077 A 6/1978 Schneider et al.
(Continued)

FOREIGN PATENT DOCUMENTS

AU 746886 5/1999
AU 341360 S 3/2012
(Continued)

OTHER PUBLICATIONS

Olivares-Ramírez et al., "Lateral flow assay HIV-based microfluidic blood fuel cell," Paper—Open Access, III Colombian Congress of Electrochemistry, 2018 Journal of Physics: Conference Series, 8 pages.
(Continued)

*Primary Examiner* — Christopher L Chin
*Assistant Examiner* — Ellis Follett Lusi
(74) *Attorney, Agent, or Firm* — Hanley, Flight & Zimmerman, LLC

(57) ABSTRACT

Methods, apparatus, systems, and articles of manufacture to make and/or process a diagnostic test device are disclosed. An example apparatus includes a sensor to measure a current
(Continued)

between a first electrode and a second electrode of a bio-electrochemical cell coupled to a test zone corresponding to a target analyte on a porous media of a device; a processor to compare the current to a threshold; and when the current is more than the threshold, identify that the target analyte is present in a sample; and an antenna to wirelessly transmit results.

17 Claims, 26 Drawing Sheets

(51) Int. Cl.
*G01N 33/549* (2006.01)
*G01N 33/58* (2006.01)

(58) Field of Classification Search
CPC ........... G01N 33/558; G01N 33/54387; G01N 33/54389; G16H 40/60; H04W 4/80; B01L 2300/0825
USPC ....... 422/400, 401, 420, 421, 425, 426, 430; 435/287.7, 287.9, 970, 805, 810; 436/169, 170, 514, 518, 530, 810
See application file for complete search history.

(56) References Cited

U.S. PATENT DOCUMENTS 4,234,538 A 11/1980 Ginsberg et al.
4,319,996 A 3/1982 Mncent et al.
4,335,693 A 6/1982 Cowles
4,390,391 A 6/1983 Fujita et al.
4,515,752 A 5/1985 Miramanda
4,608,472 A 8/1986 Kato
4,743,423 A 5/1988 Turner et al.
4,756,877 A 7/1988 Veronesi et al.
4,774,055 A 9/1988 Wakatake et al.
5,171,538 A 12/1992 Tremmel
5,244,633 A 9/1993 Jakubowicz et al.
5,266,268 A 11/1993 Antocci et al.
5,413,690 A 5/1995 Kost
5,427,912 A 6/1995 Brown
5,444,152 A 8/1995 Ishikawa et al.
5,458,852 A 10/1995 Buechler
5,494,170 A 2/1996 Burns
5,538,381 A 7/1996 Erbes
5,580,524 A 12/1996 Forrest et al.
5,609,822 A 3/1997 Carey et al.
5,610,073 A 3/1997 Chu et al.
5,621,778 A 4/1997 Erbes
5,641,006 A 6/1997 Autrey
5,670,114 A 9/1997 Sakazume et al.
5,679,309 A 10/1997 Bell
5,682,026 A 10/1997 Auclair et al.
5,702,019 A 12/1997 Grimard
5,708,247 A 1/1998 McAleer
5,765,490 A 6/1998 Colin et al.
5,788,928 A 8/1998 Carey et al.
5,795,784 A 8/1998 Arnquist et al.
5,819,964 A 10/1998 Grimard
5,843,376 A 12/1998 Ishihara et al.
5,856,194 A 1/1999 Arnquist et al.
5,876,670 A 3/1999 Mitsumaki et al.
5,882,594 A 3/1999 Kawaguchi et al.
5,927,547 A 7/1999 Papen et al.
5,947,274 A 9/1999 Taskis et al.
5,958,791 A 9/1999 Roberts et al.
5,965,086 A 10/1999 Rose et al.
5,972,295 A 10/1999 Hanawa et al.
5,985,672 A 11/1999 Kegelman et al.
6,002,474 A 12/1999 Thomas et al.
6,019,945 A 2/2000 Ohishi et al.
6,021,170 A 2/2000 Reimer et al.
6,031,454 A 2/2000 Lovejoy et al.
6,073,732 A 6/2000 Angerfors
6,123,819 A 9/2000 Peeters
6,149,872 A 11/2000 Mack et al.
6,299,567 B1 10/2001 Forrest et al.
6,358,752 B1 3/2002 Durst
6,375,898 B1 4/2002 Frank
6,394,992 B1 5/2002 Sjoeholm
6,473,190 B1 10/2002 Dosmann
6,540,891 B1 4/2003 Stewart
6,541,216 B1 4/2003 Wilsey
6,632,654 B1 10/2003 Gebrian et al.
6,723,289 B2 4/2004 Iheme et al.
6,762,056 B1 7/2004 Peeters
6,776,961 B2 8/2004 Lindsey et al.
6,846,457 B1 1/2005 Tokiwa et al.
6,872,299 B2 3/2005 Kermani et al.
6,926,864 B2 8/2005 Peeters et al.
7,109,859 B2 9/2006 Peeters
7,115,090 B2 10/2006 Lagarde
7,148,803 B2 12/2006 Bandy et al.
7,220,597 B2 5/2007 Zin et al.
7,238,521 B2 7/2007 Hahn et al.
7,239,394 B2 7/2007 Sharrock et al.
7,315,378 B2 1/2008 Phelan et al.
7,317,532 B2 1/2008 Sharrock et al.
7,381,370 B2 6/2008 Chow et al.
7,395,474 B2 7/2008 Maltseff et al.
7,446,288 B2 11/2008 Boege et al.
7,461,972 B2 12/2008 Cohen
7,492,254 B2 2/2009 Bandy et al.
7,518,504 B2 4/2009 Peeters
7,601,544 B2 10/2009 Rehm
7,641,855 B2 1/2010 Farina et al.
7,678,250 B2 3/2010 Bell et al.
7,713,703 B1 5/2010 Buechler et al.
7,749,371 B2 7/2010 Guo et al.
7,858,384 B2 12/2010 Feaster et al.
7,867,369 B2 1/2011 Bhullar et al.
7,879,624 B2 2/2011 Sharrock
7,969,307 B2 6/2011 Peeters
8,041,463 B2 10/2011 Pollack et al.
8,048,633 B2 11/2011 Collier et al.
8,057,659 B2 11/2011 Harding et al.
8,062,490 B2 11/2011 Bell et al.
8,077,042 B2 12/2011 Peeters
8,232,045 B2 7/2012 Charlton
8,308,924 B2 11/2012 Cheng et al.
8,317,997 B2 11/2012 Bar-Or et al.
8,318,099 B2 11/2012 Potyrailo et al.
8,329,012 B2 12/2012 Bar-Or et al.
8,357,276 B2 1/2013 Wang et al.
8,387,810 B2 3/2013 Livingston et al.
8,390,455 B2 3/2013 Goodnow et al.
8,394,246 B2 3/2013 Celentano et al.
D679,410 S 4/2013 Parsons et al.
8,409,412 B2 4/2013 Young et al.
8,506,775 B2 8/2013 Surridge et al.
8,545,693 B2 10/2013 McColl et al.
8,613,850 B2 12/2013 Lin et al.
8,623,292 B2 1/2014 Song et al.
8,641,888 B2 2/2014 Bar-Or et al.
8,652,831 B2 2/2014 Boecker
8,758,582 B2 6/2014 Harding et al.
8,895,315 B2 11/2014 Batman et al.
9,011,658 B2 4/2015 Bryan
9,034,159 B2 5/2015 Bar-Or et al.
9,041,538 B2 5/2015 Peeters
9,121,050 B2 9/2015 Franciskovich et al.
D745,182 S 12/2015 Parsons et al.
D745,183 S 12/2015 Parsons et al.
9,336,423 B2 5/2016 Goodnow et al.
9,390,237 B2 7/2016 Myers et al.
9,400,285 B2 7/2016 Ochranek et al.
9,435,763 B2 9/2016 Le Neel et al.
9,437,798 B2 9/2016 Le Neel et al.
9,459,232 B2 10/2016 Malecha et al.
9,470,699 B2 10/2016 Peeters
9,528,959 B2 12/2016 Bar-Or
9,599,623 B2 3/2017 Chance et al.

(56) References Cited

U.S. PATENT DOCUMENTS

| | | | |
|---|---|---|---|
| 9,638,685 | B2 | 5/2017 | Gasperino et al. |
| 9,807,543 | B2 | 10/2017 | Zin et al. |
| 9,877,672 | B2 | 1/2018 | Dahl et al. |
| 9,907,470 | B2 | 3/2018 | Goodnow et al. |
| 9,921,228 | B2 | 3/2018 | Nguyen et al. |
| 9,939,438 | B2 | 4/2018 | Kavusi et al. |
| 9,939,440 | B2 | 4/2018 | Harding et al. |
| 9,949,642 | B2 | 4/2018 | Love et al. |
| D825,061 | S | 8/2018 | Parsons et al. |
| 10,071,373 | B2 | 9/2018 | Ding et al. |
| 10,110,603 | B2 | 10/2018 | Love et al. |
| 10,133,978 | B2 | 11/2018 | Beerling et al. |
| 10,136,816 | B2 | 11/2018 | Bernstein et al. |
| 10,228,377 | B2 | 3/2019 | Mccarthy et al. |
| 10,271,738 | B2 | 4/2019 | Peeters |
| 10,327,677 | B2 | 6/2019 | Hoss et al. |
| 10,331,924 | B2 | 6/2019 | Pulitzer et al. |
| 10,364,452 | B2 | 7/2019 | Wang et al. |
| D855,825 | S | 8/2019 | Parsons et al. |
| 10,392,646 | B2 | 8/2019 | Ayyub et al. |
| 10,458,972 | B2 | 10/2019 | Hengstler et al. |
| 10,578,556 | B2 | 3/2020 | Parsons et al. |
| D884,919 | S | 5/2020 | Parsons et al. |
| 10,760,111 | B2 | 9/2020 | Harding et al. |
| 10,786,229 | B2 | 9/2020 | McBean et al. |
| 10,788,485 | B2 | 9/2020 | Swager et al. |
| 10,867,701 | B1 | 12/2020 | Anhold |
| 10,913,967 | B2 | 2/2021 | Kasten |
| 11,629,369 | B2 | 4/2023 | Delile et al. |
| 2002/0079303 | A1 | 6/2002 | Offer et al. |
| 2002/0127147 | A1 | 9/2002 | Kacian et al. |
| 2002/0132353 | A1 | 9/2002 | Tamura et al. |
| 2002/0134923 | A1 | 9/2002 | Watari et al. |
| 2002/0169518 | A1 | 11/2002 | Luoma et al. |
| 2003/0032171 | A1 | 2/2003 | Gemmell et al. |
| 2003/0044317 | A1 | 3/2003 | Catt et al. |
| 2003/0044323 | A1 | 3/2003 | Diamond et al. |
| 2003/0124738 | A1 | 7/2003 | Crosby |
| 2003/0138967 | A1 | 7/2003 | Hall et al. |
| 2003/0180815 | A1 | 9/2003 | Rawson et al. |
| 2003/0202905 | A1 | 10/2003 | Devlin et al. |
| 2003/0211006 | A1 | 11/2003 | Qian et al. |
| 2004/0052688 | A1 | 3/2004 | Adema et al. |
| 2004/0114248 | A1 | 6/2004 | Hokazono et al. |
| 2004/0118705 | A1 | 6/2004 | Khan |
| 2004/0131506 | A1 | 7/2004 | Zurcher |
| 2004/0134750 | A1 | 7/2004 | Luoma |
| 2004/0144474 | A1 | 7/2004 | Drummond et al. |
| 2004/0166043 | A1 | 8/2004 | Vandine et al. |
| 2004/0214253 | A1 | 10/2004 | Paek |
| 2005/0029097 | A1 | 2/2005 | Cheng et al. |
| 2005/0036148 | A1 | 2/2005 | Phelan |
| 2005/0106756 | A1 | 5/2005 | Blankenstein et al. |
| 2005/0112589 | A1 | 5/2005 | Hahn et al. |
| 2005/0142040 | A1 | 6/2005 | Hanawa et al. |
| 2005/0153426 | A1 | 7/2005 | Muller et al. |
| 2005/0230380 | A1 | 10/2005 | Yoshino et al. |
| 2005/0261562 | A1 | 11/2005 | Zhou et al. |
| 2006/0003400 | A1 | 1/2006 | Byrd et al. |
| 2006/0116269 | A1 | 6/2006 | Lagarde |
| 2006/0243591 | A1 | 11/2006 | Plotkin et al. |
| 2006/0246214 | A1 | 11/2006 | Plotkin et al. |
| 2006/0263248 | A1 | 11/2006 | Gomm et al. |
| 2006/0281193 | A1 | 12/2006 | Petrilla et al. |
| 2006/0286004 | A1 | 12/2006 | Jacobs et al. |
| 2006/0290496 | A1 | 12/2006 | Peeters |
| 2006/0293200 | A1 | 12/2006 | Takayama et al. |
| 2007/0034592 | A1 | 2/2007 | Pavlovic et al. |
| 2007/0116599 | A1 | 5/2007 | Walters |
| 2007/0156129 | A1 | 7/2007 | Kovalcheck |
| 2007/0193882 | A1 | 8/2007 | Dai et al. |
| 2007/0205114 | A1 | 9/2007 | Mathur |
| 2007/0298487 | A1 | 12/2007 | Bachur et al. |
| 2008/0020481 | A1 | 1/2008 | Yamamoto et al. |
| 2008/0044311 | A1 | 2/2008 | Iguchi et al. |
| 2008/0064090 | A1 | 3/2008 | Whittlinger |
| 2008/0085222 | A1 | 4/2008 | Fukuda et al. |
| 2008/0114228 | A1 | 5/2008 | McCluskey et al. |
| 2008/0158552 | A1 | 7/2008 | Tokunaga et al. |
| 2008/0213742 | A1 | 9/2008 | Asgari et al. |
| 2008/0251490 | A1 | 10/2008 | Livingston et al. |
| 2008/0269950 | A1 | 10/2008 | Greco et al. |
| 2008/0297769 | A1 | 12/2008 | Bamberg et al. |
| 2008/0317632 | A1 | 12/2008 | Shimasaki et al. |
| 2009/0004058 | A1 | 1/2009 | Liang et al. |
| 2009/0017491 | A1 | 1/2009 | Lemme et al. |
| 2009/0035867 | A1 | 2/2009 | Yagi et al. |
| 2009/0081081 | A1 | 3/2009 | Kowari et al. |
| 2009/0098662 | A1 | 4/2009 | Birch et al. |
| 2009/0107927 | A1 | 4/2009 | Belgrader |
| 2009/0123955 | A1 | 5/2009 | Marfurt |
| 2009/0148345 | A1 | 6/2009 | Hamazumi et al. |
| 2009/0162247 | A1 | 6/2009 | Tokieda et al. |
| 2009/0181361 | A1 | 7/2009 | Xu et al. |
| 2009/0192813 | A1 | 7/2009 | Gejdos et al. |
| 2009/0203059 | A1* | 8/2009 | Davis ........................ C12Q 1/37 435/23 |
| 2009/0215159 | A1 | 8/2009 | Kirby |
| 2009/0218704 | A1 | 9/2009 | Murakami |
| 2009/0220379 | A1 | 9/2009 | Wakamiya et al. |
| 2009/0280551 | A1 | 11/2009 | Cardosi |
| 2009/0325309 | A1 | 12/2009 | Favuzzi et al. |
| 2010/0028215 | A1 | 2/2010 | Schenk |
| 2010/0034700 | A1 | 2/2010 | Rousseau et al. |
| 2010/0055716 | A1 | 3/2010 | Tsutsui et al. |
| 2010/0056387 | A1 | 3/2010 | Schulz et al. |
| 2010/0059474 | A1 | 3/2010 | Brandenburger et al. |
| 2010/0107784 | A1 | 5/2010 | Stein |
| 2010/0112678 | A1 | 5/2010 | Dilleen |
| 2010/0133292 | A1 | 6/2010 | Ware et al. |
| 2010/0140149 | A1 | 6/2010 | Fulkerson et al. |
| 2010/0150298 | A1 | 6/2010 | Gilmore et al. |
| 2010/0159611 | A1 | 6/2010 | Song et al. |
| 2010/0206226 | A1 | 8/2010 | Ishii et al. |
| 2010/0206727 | A1 | 8/2010 | Cardosi |
| 2010/0213057 | A1 | 8/2010 | Feldman et al. |
| 2010/0219072 | A1 | 9/2010 | Cheng et al. |
| 2010/0233035 | A1 | 9/2010 | Denawa et al. |
| 2010/0267065 | A1 | 10/2010 | Geiger |
| 2010/0290952 | A1 | 11/2010 | Koike et al. |
| 2011/0014633 | A1 | 1/2011 | Ifuku et al. |
| 2011/0117540 | A1 | 5/2011 | Cary |
| 2011/0155590 | A1 | 6/2011 | Huffstodt |
| 2011/0157580 | A1 | 6/2011 | Nogami et al. |
| 2011/0162438 | A1 | 7/2011 | Tokieda et al. |
| 2011/0165299 | A1 | 7/2011 | Sato et al. |
| 2011/0188095 | A1 | 8/2011 | Shiraishi |
| 2011/0236959 | A1 | 9/2011 | Wei |
| 2011/0236990 | A1 | 9/2011 | Mizutani et al. |
| 2011/0271773 | A1 | 11/2011 | Komatsu et al. |
| 2011/0284393 | A1 | 11/2011 | Macfie |
| 2011/0303221 | A1 | 12/2011 | Kohnle |
| 2011/0306072 | A1 | 12/2011 | Nicholls |
| 2012/0039748 | A1 | 2/2012 | Mimura et al. |
| 2012/0073986 | A1 | 3/2012 | Jackson et al. |
| 2012/0107851 | A1 | 5/2012 | Killard |
| 2012/0114526 | A1 | 5/2012 | Watanabe et al. |
| 2012/0152935 | A1 | 6/2012 | Kitaizumi et al. |
| 2012/0156764 | A1 | 6/2012 | Kondo |
| 2012/0195808 | A1 | 8/2012 | Arras et al. |
| 2012/0199497 | A1 | 8/2012 | Liu et al. |
| 2012/0199498 | A1 | 8/2012 | Alvarez-Icaza |
| 2012/0206713 | A1 | 8/2012 | Nogami et al. |
| 2012/0218854 | A1 | 8/2012 | Behringer et al. |
| 2012/0248144 | A1 | 10/2012 | Barron |
| 2012/0284049 | A1 | 11/2012 | Baym et al. |
| 2012/0298528 | A1 | 11/2012 | Asano et al. |
| 2012/0301359 | A1 | 11/2012 | Kraemer et al. |
| 2013/0017535 | A1 | 1/2013 | Frey et al. |
| 2013/0059376 | A1 | 3/2013 | Justice et al. |
| 2013/0084590 | A1 | 4/2013 | Lugo |
| 2013/0084591 | A1 | 4/2013 | Mccoll et al. |
| 2013/0095508 | A1 | 4/2013 | Campitelli et al. |
| 2013/0116524 | A1 | 5/2013 | Cole et al. |

(56) References Cited

U.S. PATENT DOCUMENTS

2013/0123089 A1 5/2013 Johns et al.
2013/0125648 A1 5/2013 Murashie et al.
2013/0129166 A1 5/2013 Mueller et al.
2013/0157380 A1 6/2013 Zhou et al.
2013/0164193 A1 6/2013 Semenov et al.
2013/0167872 A1 7/2013 Weston et al.
2013/0199942 A1 8/2013 Whitehead et al.
2013/0199943 A1 8/2013 Craggs
2013/0220835 A1 8/2013 Liu et al.
2013/0230846 A1 9/2013 Babu et al.
2013/0280795 A1 10/2013 Dahl et al.
2013/0284609 A1 10/2013 Liu et al.
2013/0323758 A1 12/2013 Oguri et al.
2013/0341207 A1 12/2013 Whitehead et al.
2013/0341208 A1 12/2013 Whyte
2013/0341209 A1 12/2013 Whyte
2014/0043187 A1 2/2014 Ellum et al.
2014/0202829 A1 7/2014 Eberhardt et al.
2014/0260089 A1 9/2014 Luoma, II
2014/0262830 A1 9/2014 Cha et al.
2014/0263316 A1 9/2014 Accurso
2014/0269158 A1 9/2014 Luoma, II
2014/0271411 A1 9/2014 Luoma, II et al.
2014/0273242 A1 9/2014 Ochranek et al.
2014/0273245 A1 9/2014 Ochranek et al.
2014/0273268 A1 9/2014 Cerra et al.
2014/0305227 A1 10/2014 Johns
2014/0323350 A1 10/2014 Nguyen et al.
2014/0339100 A1 11/2014 Malecha
2015/0044098 A1 2/2015 Smart et al.
2015/0094227 A1 4/2015 McCarthy et al.
2015/0176049 A1 6/2015 Elder et al.
2015/0182153 A1 7/2015 Feldman
2015/0204891 A1 7/2015 Parsons
2015/0207334 A1 7/2015 Mitcheson et al.
2015/0224503 A1 8/2015 Dulaff
2015/0226761 A1 8/2015 Mizutani et al.
2015/0241378 A1 8/2015 Liu
2015/0241455 A1 8/2015 Parsons
2015/0241457 A1 8/2015 Miller
2015/0244852 A1 8/2015 Erickson et al.
2015/0260713 A1 9/2015 Ghaffari
2015/0346143 A1 12/2015 Gover
2015/0346177 A1 12/2015 Vardi
2015/0362453 A1 12/2015 Macfie
2016/0017399 A1 1/2016 Cardosi et al.
2016/0103075 A1 4/2016 Borich et al.
2016/0109350 A1 4/2016 Esaki et al.
2016/0139156 A1 5/2016 Lakdawala
2016/0167042 A1 6/2016 Tyrrell et al.
2016/0178607 A1 6/2016 Husheer
2016/0184826 A1 6/2016 Nemoto
2016/0187283 A1 6/2016 Cooper
2016/0202204 A1 7/2016 Rodgers
2016/0318022 A1 11/2016 Accurso
2016/0349237 A1 12/2016 Klinec et al.
2016/0352329 A1 12/2016 Southern et al.
2016/0356770 A1 12/2016 Fleischer
2016/0370293 A1 12/2016 Parsons et al.
2017/0016044 A1 1/2017 Kolehmainen et al.
2017/0020424 A1 1/2017 Holweg et al.
2017/0102378 A1 4/2017 Florescu et al.
2017/0121754 A1 5/2017 Feldman
2017/0173578 A1 6/2017 Crooks
2017/0194115 A1 7/2017 Blus
2017/0240945 A1 8/2017 Marquant
2018/0008239 A1 1/2018 McBean et al.
2018/0059006 A1 3/2018 Fritchie et al.
2018/0156792 A1 6/2018 Parsons et al.
2018/0193498 A1 7/2018 Fritchie et al.
2018/0197623 A1 7/2018 Sim
2018/0229232 A1 8/2018 Chang
2018/0231491 A1 8/2018 Liu et al.
2018/0304260 A1 10/2018 Thomas
2019/0079045 A1 3/2019 Goebbert et al.
2019/0086431 A1 3/2019 Isaacson et al.
2019/0126265 A1 5/2019 Weigl et al.
2019/0168217 A1 6/2019 Eason
2019/0204334 A1 7/2019 Mccarthy et al.
2019/0351415 A1 11/2019 Barman
2019/0362841 A1 11/2019 Aysin et al.
2020/0096470 A1 3/2020 Wester et al.
2020/0124595 A1 4/2020 Irudayaraj et al.
2020/0155127 A1 5/2020 Fry et al.
2020/0166461 A1 5/2020 Fung et al.
2020/0166462 A1 5/2020 Parsons et al.
2020/0166473 A1 5/2020 Hatamian
2020/0174025 A1 6/2020 Joyce
2020/0209235 A1 7/2020 Guckenberger
2020/0225218 A1 7/2020 Ranzoni et al.
2020/0232982 A1 7/2020 Parsons et al.
2020/0242769 A1 7/2020 Limburg et al.
2020/0242809 A1 7/2020 Limburg et al.
2020/0271614 A1 8/2020 Elder
2020/0372680 A1 11/2020 Limburg
2020/0386751 A1 12/2020 Takulapalli
2020/0392556 A1 12/2020 Harding et al.
2021/0063339 A1 3/2021 Kuo et al.
2021/0068730 A1 3/2021 Johnson et al.
2021/0080451 A1 3/2021 Klemm
2021/0080475 A1 3/2021 Parsons
2021/0102232 A1 4/2021 González-Macia et al.
2021/0109055 A1 * 4/2021 Hatamian ................ B01L 9/52
2021/0113131 A1 4/2021 Lee et al.
2021/0131973 A1 5/2021 Berg
2021/0148888 A1 5/2021 Pekec et al.
2021/0148902 A1 5/2021 Esquivel Bojorquez et al.
2021/0156855 A1 5/2021 Ranzoni et al.
2021/0255111 A1 8/2021 Bernd
2021/0258565 A1 8/2021 Bernd
2021/0263018 A1 8/2021 Taran
2021/0285888 A1 9/2021 Limburg
2021/0285910 A1 9/2021 Hatamian
2021/0349098 A1 11/2021 Yehudai-Reshef et al.
2021/0372985 A1 12/2021 Hengstler et al.
2022/0065847 A1 3/2022 Hasan
2022/0104736 A1 4/2022 Berg
2022/0112536 A1 4/2022 Bui et al.
2022/0122254 A1 4/2022 Limburg
2022/0250060 A1 8/2022 Werthman
2022/0308049 A1 9/2022 Miller et al.
2022/0341919 A1 10/2022 Venkatesan et al.
2023/0030862 A1 2/2023 Eiichi et al.
2023/0333118 A1 * 10/2023 Laufer ............... G01N 33/5438
2024/0066521 A1 2/2024 Uhlig et al.
2024/0125777 A1 4/2024 Takulapalli
2025/0060365 A1 2/2025 Uhlig et al.

FOREIGN PATENT DOCUMENTS

AU 2013204428 A1 5/2013
AU 2015201635 A1 4/2015
AU 2014284128 1/2016
AU 201615947 S 11/2016
AU 201615949 S 11/2016
CN 1461810 A 12/2003
CN 1512175 A 7/2004
CN 2629037 Y 7/2004
CN 1781022 A 5/2006
CN 101236171 A 8/2008
CN 101266243 A 9/2008
CN 101762628 A 6/2010
CN 201514408 U 6/2010
CN 103196960 A 7/2013
CN 203148884 8/2013
CN 203310799 U 11/2013
CN 203662765 6/2014
CN 103940988 A 7/2014
CN 104749228 7/2015
CN 105899132 A 8/2016
CN 106483284 3/2017
CN 106680347 5/2017
CN 109580742 4/2019
CN 209979545 1/2020

(56) References Cited

FOREIGN PATENT DOCUMENTS

| | | | |
|---|---|---|---|
| CN | 111033249 | | 4/2020 |
| CN | 111189899 | | 5/2020 |
| CN | 111610239 | | 9/2020 |
| CN | 111781351 | A | 10/2020 |
| CN | 112098479 | | 12/2020 |
| CN | 112683955 | | 4/2021 |
| EP | 0121980 | A2 | 10/1984 |
| EP | 1254365 | | 11/2002 |
| EP | 1269173 | | 1/2003 |
| EP | 1612275 | | 1/2006 |
| EP | 1724580 | | 10/2008 |
| EP | 2098863 | | 9/2009 |
| EP | 2280276 | | 2/2011 |
| EP | 2365329 | A1 | 9/2011 |
| EP | 2387714 | | 11/2011 |
| EP | 2485044 | A1 | 8/2012 |
| EP | 2182355 | B1 | 10/2012 |
| EP | 2245174 | B1 | 11/2012 |
| EP | 2611042 | A1 | 7/2013 |
| EP | 2681543 | A1 | 1/2014 |
| EP | 2803987 | | 11/2014 |
| EP | 2460009 | B1 | 3/2015 |
| EP | 2843848 | | 3/2015 |
| EP | 2984597 | A1 | 2/2016 |
| EP | 3022557 | A1 | 5/2016 |
| EP | 2971063 | B1 | 4/2017 |
| EP | 2737078 | B1 | 11/2017 |
| EP | 3117006 | B1 | 7/2018 |
| EP | 2681538 | B1 | 3/2019 |
| EP | 3569312 | A1 | 11/2019 |
| EP | 3602074 | A1 | 2/2020 |
| EP | 3649470 | A1 | 5/2020 |
| EP | 3655766 | A1 | 5/2020 |
| EP | 3771908 | | 2/2021 |
| EP | 4080213 | A1 | 10/2022 |
| GB | 2553512 | | 3/2018 |
| JP | HI062432 | A | 3/1998 |
| JP | 2000506610 | A | 5/2000 |
| JP | 2004505279 | A | 2/2004 |
| JP | 2006343336 | | 12/2006 |
| JP | 2007519484 | A | 7/2007 |
| JP | 2010054308 | A | 3/2010 |
| JP | 2015505251 | A | 2/2015 |
| JP | 201658390 | A | 4/2016 |
| JP | 2016517017 | A | 6/2016 |
| JP | 2017504392 | A | 2/2017 |
| JP | 2017512986 | A | 5/2017 |
| JP | 2017522556 | A | 8/2017 |
| JP | 2018091678 | A | 6/2018 |
| JP | 2019506206 | A | 3/2019 |
| JP | 6714256 | B1 | 6/2020 |
| KR | 102230114 | | 12/1899 |
| KR | 20030011165 | | 2/2003 |
| KR | 20040024489 | A | 3/2004 |
| KR | 100506165 | B1 | 8/2005 |
| KR | 20060024131 | A | 3/2006 |
| KR | 20060109595 | A | 10/2006 |
| KR | 20080076434 | A | 8/2008 |
| KR | 20110046307 | A | 5/2011 |
| KR | 20110126799 | A | 11/2011 |
| KR | 20170029603 | | 3/2017 |
| KR | 101753133 | | 7/2017 |
| KR | 102009116 | B1 | 8/2019 |
| KR | 102034352 | | 10/2019 |
| KR | 20210013578 | | 2/2021 |
| WO | 9322054 | A1 | 11/1993 |
| WO | 9324231 | A1 | 12/1993 |
| WO | 9503543 | A1 | 2/1995 |
| WO | 9506115 | A1 | 3/1995 |
| WO | 9730344 | A1 | 8/1997 |
| WO | 9734148 | A1 | 9/1997 |
| WO | 9907879 | A1 | 2/1999 |
| WO | 9958709 | A1 | 11/1999 |
| WO | 0069389 | A2 | 11/2000 |
| WO | 0072019 | A2 | 11/2000 |
| WO | WO0072019 | | 11/2000 |
| WO | 0128701 | A1 | 4/2001 |
| WO | 0157238 | A2 | 8/2001 |
| WO | 0173124 | A2 | 10/2001 |
| WO | 0210754 | A2 | 2/2002 |
| WO | WO0210754 | | 2/2002 |
| WO | 02072265 | A1 | 9/2002 |
| WO | 02086514 | A2 | 10/2002 |
| WO | 3091717 | A1 | 11/2003 |
| WO | WO2005074161 | | 8/2005 |
| WO | WO2006026748 | | 3/2006 |
| WO | 2006109311 | A2 | 10/2006 |
| WO | WO2009015291 | | 1/2009 |
| WO | 2010085271 | A1 | 7/2010 |
| WO | WO2010094504 | | 8/2010 |
| WO | 2011014673 | A1 | 2/2011 |
| WO | 2011032228 | A1 | 3/2011 |
| WO | WO2011032228 | | 3/2011 |
| WO | WO2013057630 | | 4/2013 |
| WO | 2013070716 | A2 | 5/2013 |
| WO | 2013070744 | A2 | 5/2013 |
| WO | 2013070756 | A2 | 5/2013 |
| WO | 2013117233 | A1 | 8/2013 |
| WO | 2014025817 | A1 | 2/2014 |
| WO | WO2014042979 | | 3/2014 |
| WO | WO2014051425 | | 4/2014 |
| WO | WO2014080212 | | 5/2014 |
| WO | 2014165373 | A1 | 10/2014 |
| WO | 2014171891 | A1 | 10/2014 |
| WO | WO2014171891 | | 10/2014 |
| WO | 2015017591 | A1 | 2/2015 |
| WO | WO2015017591 | | 2/2015 |
| WO | 2015036392 | A1 | 3/2015 |
| WO | 2016037234 | A1 | 3/2016 |
| WO | 2016154672 | A1 | 10/2016 |
| WO | 2017207958 | A1 | 12/2017 |
| WO | 2017216339 | A1 | 12/2017 |
| WO | 2018053501 | A1 | 3/2018 |
| WO | 2018060706 | A1 | 4/2018 |
| WO | WO2018152573 | | 8/2018 |
| WO | 2018218284 | A1 | 12/2018 |
| WO | 2019023597 | A1 | 1/2019 |
| WO | WO2019006500 | | 1/2019 |
| WO | WO2019108859 | | 6/2019 |
| WO | 2019238500 | A1 | 12/2019 |
| WO | 2019238501 | A1 | 12/2019 |
| WO | WO2019243314 | | 12/2019 |
| WO | 2020109525 | A1 | 6/2020 |
| WO | 2020117709 | A1 | 6/2020 |
| WO | 2020152679 | A1 | 7/2020 |
| WO | WO2020231159 | | 11/2020 |
| WO | 2020255172 | A1 | 12/2020 |
| WO | 2020260246 | A1 | 12/2020 |
| WO | WO2020237308 | | 12/2020 |
| WO | WO2020264058 | | 12/2020 |
| WO | 2021001285 | A1 | 1/2021 |
| WO | WO2021053206 | | 3/2021 |
| WO | WO2021076933 | | 4/2021 |
| WO | 2021125173 | A1 | 6/2021 |
| WO | 2021240020 | A2 | 12/2021 |
| WO | 2021240023 | A1 | 12/2021 |
| WO | 2022155380 | A1 | 7/2022 |

OTHER PUBLICATIONS

Yuan et al., "Sensing by Growing Antennas: A Novel Approach for Designing Passive RFID based Biosensors," IEEE, 2015, 4 pages.

Du et al., "Integrated Lateral Flow Test Strip with Electrochemical Sensor for Quantification of Phosphorylated Cholinesterase: Biomarker of Exposure to Organophosphorus Agents," Article, Analytical Chemistry, ACS Publications, published Dec. 15, 2011, 6 pages.

Harvey, LibreTexts, Chemistry, "11.4: Voltammetric Methods," Nov. 10, 2020, retrieved from: https://chem.libretexts.org/@go/page/5604, 26 pages.

B. B. Lal, "The Decomposition of Hydrogen Peroxide by Potassium Ferrocyanide," received Dec. 11, 1952, 12 pages.

(56) References Cited

OTHER PUBLICATIONS

Katz et al., "A non-compartmentalized glucose | O2 biofuel cell by bioengineered electrode surfaces," Short Communication, Journal of Electroanalytical Chemistry, 479 (1999) 64-68, 5 pages.
Wohlfahrt, "The chemical mechanism of action of glucose oxidase from Aspergillus niger," Molecular and Cellular Biochemistry 260: 69-83, (2004), Kluwer Academic Publishers. Printed in the Netherlands, accepted Sep. 10, 2003, 17 pages.
Maenga et al., "A novel microfluidic biosensor based on an electrical detection system for alpha-fetoprotein," Biosensors and Bioelectronics 23 (2008) 1319-1325, accepted Nov. 28, 2007, 7 pages.
Liu et al., "Design and Characterization of a Silver-Enhanced Gold Nanoparticle-Based Biochip," IEE, 2009, 4 pages.
Liu et al., "Exploiting Sub-threshold and Above-threshold Characteristics in a Silver-Enhanced Gold Nanoparticle Based Biochip," 31st Annual International Conference of the IEEE EMBS, Minneapolis, Minnesota, USA, Sep. 2-6, 2009, 4 pages.
Lui et al., "Biomolecules Detection Using a Silver-Enhanced Gold Nanoparticle-Based Biochip," Special issue Article, Springer, Nanoscale Res Lett (2010), published online on Feb. 2, 2010, 6 pages.
Yáñez-Sedeño et al., "Magnetic Particles Coupled to Disposable Screen Printed Transducers for Electrochemical Biosensing," Review, Sensors, MDPI, published Sep. 25, 2016, 32 pages.
Lui et al., "Aptamer-based Origami Paper Analytical Device for Electrochemical Detection of Adenosine**," National Institute of Health, Author Manuscript, Published in final edited form as: Angew Chem Int Ed Engl., Jul. 9, 2012, 9 pages.
Narahari, "Electrically Actuated Microfluidics in Fabric," A Dissertation, Chemical Engineering, Northeastern University, Boston Massachusetts, Aug. 2016, 195 pages.
Neto et al., "New Energy Sources: The Enzymatic Biofuel Cell," Review, J. Braz. Chem. Soc., vol. 24, No. 12, pp. 1891-1912, 2013, 22 pages.
Liu et al., "Paper-Based Electrochemical Biosensors: From Test Strips to Paper-Based Microfluidics," Review, Wiley Online Library, Electroanalysis, Jun. 2014, 11 pages.
International Searching Authority, "International Preliminary Report on Patentability," issued in connection with Application No. PCT/EP2021/064581, mailed Dec. 8, 2022, 16 pages.
Yuan et al., "A Novel Biosensor Based on Silver-Enhanced Self-Assembled Radio-Frequency Antennas," IEEE Sensors Journal, vol. 14, No. 4, Apr. 2014, 2 pages.
Eltzov et al., "Lateral Flow Immunoassays—from Paper Strip to Smartphone Technology," Review, Wiley Online Library, Electroanalysis, 2015, 15 pages.
Kiba et al., "Electrochemical detection of redox species flowing in a nitrocellulose membrane and application to quantitative immunochromatography," Elsevier, Contents lists available at SciVerse ScienceDirect, Electrochimica Acta, available online Jul. 27, 2012, 6 pages.
Lan et al., "Paper-Based Potentiometric Ion Sensing," ACS Publications, American Chemical Society, publication date Sep. 8, 2014, 11 pages.
Wang et al., "A novel immunochromatographic electrochemical biosensor for highly sensitive and selective detection of trichloropyridinol, a biomarker of exposure to chlorpyrifos," Elsevier, Biosensors and Bioelectronics 26 (2011), 2835-2840, available online Nov. 30, 2010, 6 pages.
Perju et al., "Integrating high-performing electrochemical transducers in lateral flow assay," Analytical and Bioanalytical Chemistry, TRENDS, accepted Mar. 17, 2021, 15 pages.
Kokkinos, "Electrochemical DNA Biosensors Based on Labeling with Nanoparticles," Review, nanomaterials, MDPI, Laboratory of Analytical Chemistry, Department of Chemistry, National and Kapodistrian University of Athens, published Sep. 23, 2019, 20 pages.
Dalamarche, "Precision diagnostics," IBM Research—Zurich Science & Technology, Technologies for healthcare and life science, retrieved Dec. 17, 2019, 3 pages.
Tominaga et al., "Quantitative and Single-step Enzyme Immunosensing Based on an Electrochemical Detection Coupled with Lateral-flow System," Analytical Sciences, The Japan Society for Analytical Chemistry, Apr. 2017, 7 pages.
Fernandez-Sanchez, "Quantitative impedimetric immunosensor for free and total prostate specific antigen based on a lateral flow assay format," Elsevier, Electrochemistry Communications 6, (2004), published online Nov. 21, 2003, 7 pages.
Rackus, "Tools for Point-of-Care Digital Microfluidics," A thesis submitted in conformity with the requirements, for the degree of Doctor of Philosophy, Department of Chemistry, University of Toronto, 2017, 159 pages.
Lu et al., "Rapid, quantitative and sensitive immunochromatographic assay based on stripping voltammetric detection of a metal ion label," Paper, The Royal Society of Chemistry 2005, Analyst, published Sep. 8, 2005, 5 pages.
Pilavaki et al., "Optimized Lateral Flow Immunoassay Reader for the Detection of Infectious Diseases in Developing Countries," Article, sensors, MDPI, published Nov. 20, 2017, 11 pages.
Zhu et al., "Using a glucose meter to quantitatively detect disease biomarkers through a universal nanozyme integrated lateral fluidic sensing platform," Elsevier, Biosensors and Bioelectronics 126 (2019) 690-696, accepted Nov. 19, 2018, 7 pages.
Venkatraman et al., "Integrated NFC power source for zero on-board power in fluorescent paper-based lateral flow immunoassays," Paper, Flexible and Printed Electronics, 2016, 8 pages.
Cui, "Wireless Biological Electronic Sensors," Biosensors, sensors, published Oct. 9, 2017, 3 pages, abstract only.
Yazawa et al., "Electronic immunochromatography embedding RFID sensor," Extended Abstracts of the 2010 International Conference on Solid State Devices and Materials, Tokyo, 2010, pp. 179-180, 2 pages.
Yuan et al., "Self-powered Wireless Affinity-based Biosensor based on Integration of Paper-based Microfluidics and Self-assembled RFID Antennas," IEEE Transactions On Biomedical Circuits and Systems, 9 pages.
Wang et al., "Semiconductor Quantum Dots for Electrochemical Biosensors," A Presentation for Partial Fulfillment of the Requirements for the Theory Class of Biosensor Nanomaterial under the supervision of Prof. Joong Hee Lee., Chapter-10, Oct. 31, 2017, 27 pages.
Kim et al., "Review of Near-Field Wireless Power and Communication for Biomedical Applications," IEEE Access, Special Section on Energy Efficient Wireless Communications With Energy Harvesting and Wireless Power Transfer, published Sep. 27, 2017, 22 pages.
Gonzalez-Solino et al., "Enzymatic Fuel Cells: Towards Self-Powered Implantable and Wearable Diagnostics," Review, biosensors, MDPI, published Jan. 29, 2018, 18 pages.
Grattieri et al., "Self-Powered Biosensors," Review, ACS Sensors, ACS Publications, American Chemical Society, published Nov. 21, 2017, 10 pages.
Iwata et al., "H2O2 Detection by Redox-based Potentiometric Sensors under Biological Environments," Sensors and Materials, vol. 30, No. 10 (2018) 2359-2367, accepted Sep. 7, 2018, 9 pages.
Ross et al., "Consumer-friendly food allergen detection: moving towards smartphone-based immunoassays," Review, Analytical and Bioanalytical Chemistry (2018), published Mar. 26, 2018, 19 pages.
Carrell et al., "Beyond the lateral flow assay: A review of paper-based microfluidics," Elsevier, Microelectronic Engineering 206 (2019) 45-54, available online Jan. 7, 2019, 10 pages.
Dincer et al., "Disposable Sensors in Diagnostics, Food, and Environmental Monitoring," Review, Disposable sensors, Advanced Materials, last revised Mar. 29, 2019, 28 pages.
Khlebtsov et al., "Quantifying the Numbers of Gold Nanoparticles in the Test Zone of Lateral Flow Immunoassay Strips," ACS, Applied Nano Materials, 2019, published Jun. 28, 2019, 9 pages.
Kitadai et al., "Metals likely promoted protometabolism in early ocean alkaline hydrothermal systems," Science Advances, Research Article, Oct. 1, 2019, 10 pages.

(56) References Cited

OTHER PUBLICATIONS

Zhu et al., "A paper electrode integrated lateral flow immunosensor for quantitative analysis of oxidative stress induced DNA damage," Paper, Analyst, Royal Society of Chemistry, accepted Mar. 9, 2014, 8 pages.
Martín-Yerga, "Electrochemical Detection and Characterization of Nanoparticles with Printed Devices," Review, Biosensors, MDPI, published Mar. 28, 2019, 23 pages.
Xiao et al., "Tackling the Challenges of Enzymatic (Bio) Fuel Cells," HAL, archives-ouvertes, submitted Jun. 28, 2019, 138 pages.
Dempsey et al., "Disposable Printed Lateral Flow Electrochemical Immunosensors for Human Cardiac Troponin T," IEEE Sensors Journal, vol. 18, No. 5, Mar. 1, 2018, 7 pages.
Lin et al., "A nanoparticle label/immunochromatographic electrochemical biosensor for rapid and sensitive detection of prostate-specific antigen," Elsevier, Biosensors and Bioelectronics 23 (2008), available online Feb. 21, 2008, 7 pages.
Cao et al., "An Integrated Electrochemical Immunochromatographic Test Strip Based on the Amplification of Gold Nanoparticles for Quantitative Detection of Alpha-Fetoprotein," Article, American Scientific Publishers, Journal of Nanoscience and Nanotechnology, vol. 16, pp. 12187-12193, 2016, accepted Sep. 5, 2015, 8 pages.
Akanda et al., "An interference-free and rapid electrochemical lateral-flow immunoassay for one-step ultrasensitive detection with serum," Paper, Analyst, Royal Society of Chemistry, published on Jan. 30, 2014, 6 pages.
Juntenen, "Lateral Flow Immunoassays with Fluorescent Reporter Technologies," Turun yliopisto University of Turku, 2018, 96 pages.
Gonzalez Guerrero, "Enzymatic Microfluidic Fuel Cells: From Active to Passive Power Sources," Doctorado en Ciencia de Materiales, Departamento de Física, 149 pages.
Kuo et al., "Biofuel Cells Composed by Using Glucose Oxidase on Chitosan Coated Carbon Fiber Cloth," International Journal of Electrochemical Science, (2013), published Jul. 1, 2013, 14 pages.
Pellitero et al., "Rapid prototyping of electrochemical lateral flow devices: stencilled electrodes," Paper, Royal Society of Chemistry, Analyst, 2016, accepted Mar. 7, 2016, 8 pages.
Chen et al., "Computational Lateral Flow Biosensor for Proteins and Small Molecules: A New Class of Strip Logic Gates," Letter, analytical chemistr, ACS Publications, published Jul. 5, 2012, 5 pages.
Sajid et al., "Designs, formats and applications of lateral flow assay: A literature review," Original Article, Journal of Saudi Chemical Society (2015) 19, 689-705, King Saud University, available online Sep. 16, 2014, 17 pages.
International Searching Authority, "Invitation to Pay Additional Fees," issued in connection with Application No. PCT/EP2021/064581, mailed Sep. 2, 2021, 13 pages.
Möller, "DNA-Chips mit elektrischer Detektion," Dissertation, 136 pages.
Dropsens, "Innovative Technology for Miniaturized Electrochemistry," www.dropsens.com, 40 pages.
Medina-Sánchez et al., "Eco-friendly electrochemical lab-on-paper for heavy metal detection," Research Paper, Analytical & Bioanalytical Chemistry (2015), Springer Science & Business Media B.V, published online Sep. 24, 2015, 6 pages.
Kiba et al., "Electrochemical detection of redbox species flowing in a nitrocellulose membrane and application to quantitative immunochromatography," ScienceDirect, Electrochimica Acta, vol. 81, Oct. 30, 2012, 2 pages, abstract only, 2 pages.
Ruiz-Vega et al., "Electrochemical Lateral Flow Devices: Towards Rapid Immunomagnetic Assays," Article, ChemElectroChem, 2017 Wiley-VCH Verlag GmbH & Co. KGaA, Weinheim, 11 pages.
Mahato et al., "Electrochemical Immunosensors: Fundamentals and Applications in Clinical Diagnostics," Chapter 14, Handbook of Immunoassay Technologies, 2018 Elsevier Inc., 56 pages.
Lateral Flow Assays: What can we expect for the future?, "Exploring the future of Lateral Flow Assays Development," GE Healthcare Life Sciences, 2019, retrieved Jan. 23, 2019, 4 pages.
Mao et al., "Multiplex electrochemical immunoassay using gold nanoparticle probes and immunochromatographic strips," Elsevier, Electrochemistry Communications 10 (2008), available online Aug. 23, 2008, 6 pages.
Lu et al., "Dual Immunomagnetic Nanobeads-Based Lateral Flow Test Strip for Simultaneous Quantitative Detection of Carcinoembryonic Antigen and Neuron Specific Enolase," Scientific Reports, www.nature.com/scientificreports/, published Feb. 10, 2017, 10 pages.
International Searching Authority, "International Preliminary Report on Patentability," issued in connection with International Application No. PCT/IB2023/058451, issued Feb. 25, 2025, 13 pages.
Kitamura, "Chronoamperometry," Electrochemistry, No. 1, 2000, pp. 63-68, 12 pages.
Krorakai et al., "Smartphone-Based NFC Potentiostat for Wireless Electrochemical Sensing," Applied Sciences 11, No. 1:392, Jan. 3, 2021, 13 pages. https://doi.org/10.3390/app11010392.
Larpant et al. "Paper-Based Competitive Immunochromatography Coupled with an Enzyme-Modified Electrode to Enable the Wireless Monitoring and Electrochemical Sensing of Cotinine in Urine," MDPI, Sensors, vol. 21, No. 5, published Feb. 28, 2021, p. 1659, 16 pages.
International Searching Authority, "Search Report and Written Opinion of the International Searching Authority," issued in connection with International Patent Application No. PCT/EP2022/083431, mailed on Apr. 13, 2023, 11 pages.
International Searching Authority, "Partial International Search Report," issued in connection with International Patent Application No. PCT/IB2023/058451, mailed on Nov. 27, 2023, 11 pages.
International Searching Authority, "International Preliminary Report on Patentability," issued in connection with International Patent Application No. PCT/EP2022/083431, mailed on Jun. 13, 2024, 13 pages.
European Patent Office, "Communication pursuant to Article 94(3) EPC," issued in connection with European Patent Application No. 21 731 707.2, dated Dec. 10, 2024, 7 pages.
Japanese Patent Office, "Search Report by Registered Search Organization ," issued in connection with Japanese Patent Application No. 2022-573419, dated Mar. 19, 2025, 36 pages. [English Translation Included].
Japanese Patent Office, "Notice of Reasons for Refusal," issued in connection with Japanese Patent Application No. 2022-573419, dated Apr. 1, 2025, 9 pages. [English Translation Included].
Japanese Patent Office, "Search Report by Registered Search Organization," issued in connection with Japanese Patent Application No. 2024-532245, dated May 20, 2025, 33 pages. [English Translation Included].
Japanese Patent Office, "Notice of Reasons for Refusal," issued in connection with Japanese Patent Application No. 2024-532245, dated Jun. 3, 2025, 11 pages. [English Translation Included].
The State Intellectual Property of People's Republic of China, "First Office Action and First Search," issued in connection with Chinese patent Application No. 202180059130.0, dated Jul. 24, 2025, 28 pages. [English Translation Included].
European Patent Office, "Communication under Rule 71(3) EPC," issued in connection with European Patent Application No. 21 731 707.2, dated Aug. 19, 2025, 9 pages.
Japanese Patent Office, "Decision to Grant a Patent," issued in connection with Japanese Patent Application No. 2022-573419, dated Aug. 26, 2025, 5 pages. [English Translation Included].
Park et al., "Array-based electrical detection of DNA with nanoparticle probes. (Reports)" Reports, American Association for the Advancement of Science, vol. 295, No. 5559, published Feb. 22, 2002, 7 pages.
Shapley, "Reduction Potentials," published in connection with the University of Illinois, retreived from: http://butane.chem.uiuc.edu/pshapley/genchem2/b9/2.html, published 2012, 2 pages.
Zhang et al., Lab on a Chip, Lab Chip, "Stacking Flow Immunoassay for the Detection of Dengue-Specific Immunoglobulins in Salivary Fluid," Royal Society of Chemistry, 2015, 15, 1465-1471, first published Jan. 12, 2015, 8 pages.
Cao Liangli et al., "An Integrated Electrochemical Immunochromatographic Test Strip Based on the Amplification of Gold Nanoparticles for Quantitative Detection of Alpha-

(56) References Cited

OTHER PUBLICATIONS

Fetoprotein," Journal of Nanoscience and Nanotechnology, US, vol. 16, No. 12, doi: 10.1166/jnn.2016.12983, ISSN 1533-4880, URL: http://dx.doi.org/10.1166/jnn.2016.12983, published Dec. 1, 2016, pp. 12187-12193, 7 pages.

Wikipedia, "Concentration Cell," retrieved from: https://en.wikipedia.org/wiki/Concentration_cell, accessed Jan. 30, 2023, 3 pages.

European Patent Office, "Communication pursuant to Article 94(3) EPC," issued in connection with Application No. 21731707.2, dated Jan. 17, 2024, 6 pages.

International Searching Authority, "Written Opinion," issued in connection with International Patent Application No. PCT/IB2023/058451, mailed on Jan. 23, 2024, 14 pages.

International Searching Authority, "International Search Report," issued in connection with International Patent Application No. PCT/IB2023/058451, mailed on Jan. 23, 2024, 7 pages.

International Searching Authority, "International Search Report and Written Opinion," issued in connection with PCT Application No. PCT/EP2021/064581, mailed Nov. 30, 2021, 27 pages.

Narahari, "Electrically Actuated Microfluidics in Fabric," PhD Thesis (Dissertation), Aug. 2016, 195 pages.

Cao et al., "An Integrated Electrochemical Immunochromatographic Test Strip Based on the Amplification of Gold Nanoparticles for Quantitative Detection of Alpha-Fetoprotein," Article, Journal of Nanoscience and Nanotechnology, vol. 16, 12187-12193, 2016, 7 pages.

Korean Intellectual Property Office,"Request for the Submission of an Opinion," issued in connection with Korean Patent Application No. 10-2022-7045984, issued on Dec. 21, 2021, 6 pages. (English Translation Included).

Japanese Patent Office, "Decision to Grant a Patent," issued in connection with Japanese Patent Application No. 2024-532245, dated Jan. 6, 2026, 5 pages. [English Translation Included].

* cited by examiner

MACHINE READABLE DIAGNOSTIC TEST DEVICES AND METHODS AND APPARATUS TO MAKE AND/OR PROCESS THE SAME

RELATED APPLICATIONS

This patent arises from a national stage of International Patent Application Serial No. PCT/EP2021/064581, which was filed on May 31, 2021, which claims priority to U.S. Provisional Patent Application Ser. No. 63/129,375, which was filed on Dec. 22, 2020 and to U.S. Provisional Patent Application Ser. No. 63/032,093, which was filed on May 29, 2020. International Patent Application Serial No. PCT/EP2021/064581, U.S. Provisional Patent Application Ser. No. 63/129,375, and U.S. Provisional Patent Application Ser. No. 63/032,093 are hereby incorporated herein by reference in their entireties. Priority to International Patent Application Serial No. PCT/EP2021/064581, U.S. Provisional Patent Application Ser. No. 63/032,093, and U.S. Provisional Patent Application Ser. No. 63/129,375 is hereby claimed.

FIELD OF THE DISCLOSURE

This disclosure relates generally to biosensors, and, more particularly, to a machine readable diagnostic test devices and methods and apparatus to make and/or process the same.

BACKGROUND

A biosensor (e.g., a lateral flow device, such as a lateral flow assay (LFA)) is a device that is capable of detecting a condition, disease, etc., in a human or animal based on a sample (e.g., a blood sample, a saliva sample, a urine sample, etc.) from the human or animal. LFAs have been used to detect the presence of a target analyte to determine pregnancy, presence of HIV, presence of Ebola, presence of different toxins, etc.

Figure 1A:
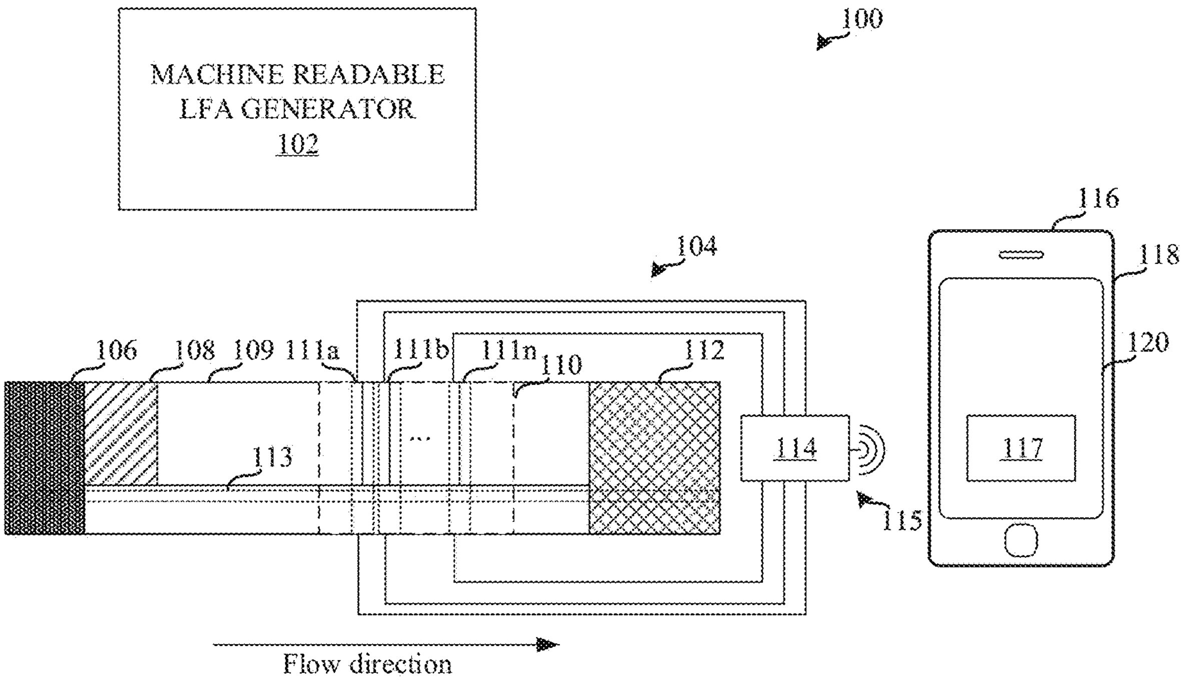
FIG. 1A is an example environment including an example machine readable lateral flow immunoassay generator to generate a machine readable lateral flow immunoassay described in conjunction with examples disclosed herein.

The figures are not to scale. Instead, the thickness of the layers or regions may be enlarged in the drawings. In general, the same reference numbers will be used throughout the drawing(s) and accompanying written description to refer to the same or like parts. As used in this patent, stating that any part (e.g., a layer, film, area, region, or plate) is in any way on (e.g., positioned on, located on, disposed on, or formed on, etc.) another part, indicates that the referenced part is either in contact with the other part, or that the referenced part is above the other part with one or more intermediate part(s) located therebetween. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Stating that any part is in "contact" with another part means that there is no intermediate part between the two parts. Although the figures show layers and regions with clean lines and boundaries, some or all of these lines and/or boundaries may be idealized. In reality, the boundaries and/or lines may be unobservable, blended, and/or irregular.

DETAILED DESCRIPTION

Rapid diagnostic tests include a biosensor or test strip device (e.g., lateral flow immunoassay (LFA)), which is a device including a first region to obtain a sample (e.g., blood, urine, saliva, etc.) and a second region that changes (e.g., changes color and/or experiences another change in a physical property) when a target analyte corresponding to a particular disease or condition is present in the sample. For example, a user applies the sample to a sample pad of a test strip device, or simply "test strip" (e.g., an LFA, etc.). Once applied, the sample migrates along the test strip to a conjugate pad that contains conjugates (e.g., detectable labels, tags, linkers, antibodies, antigens, etc.) specific to the target analyte. If the sample includes the target analyte, a reaction (e.g., a chemical reaction, biochemical reaction, physical reaction, etc.) will occur on the conjugate pad to bind the target analyte with the conjugates. The test strip also includes a test line that contains molecules (e.g., immobilized antibodies, antigens, analytes, aptamers, etc., specific to the target analyte), which bind the first set of conjugate molecules (e.g., probe molecules) from the conjugate pad. For example, if the analyte of interest is an antibody, the positive test area includes immobilized antigen. If the analyte of interest is an antigen, the positive test area includes immobilized antibody. The labeled substance or conjugate includes a first binding component that is able to bind the analyte of interest and, in some examples, a second visualization component. Accordingly, when the sample (e.g., including the bounded target analyte) flows to a test zone (e.g., a reaction zone), the antibodies, analytes, or antigens of the test line bind to the bounded target analyte, thereby immobilizing the target analyte. In some test strips, the immobilized target analytes result in a visual output that identifies that the target analyte was present in the sample. Accordingly, a scanner or user can identify whether the target analyte (e.g., corresponding to a condition or disease) is present in the sample based on the color of the test zone.

"Target analyte", "analyte" or "analyte of interest" refers to the compound or the composition to be detected or measured from the sample, which has at least one epitope or binding site. The analyte can be any substance for which there exists a naturally occurring analyte-specific binding member or for which an analyte-specific binding member can be prepared. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), and/or metabolites of or antibodies to any of the above substances. The term "analyte" also includes any antigenic substances, haptens, antibodies, macromolecules, and/or combinations thereof.

"Label" refers to any substance which is capable of producing a signal that is detectable by visual and/or instrumental means. Various labels suitable for use in examples disclosed herein include labels that produce signals through chemical and/or physical means. Examples include enzymes and substrates, chromagens, fluorescent compounds, chemiluminescent compounds, colored or colorable organic polymer latex particles, liposomes, and/or other vesicles containing directly visible substances. In some examples, radioactive labels, colloidal metallic particles, and/or colloidal non-metallic particles are employed. In some examples, labels include colloidal gold and latex particles.

"Labeled substance" or "conjugate" refers to a substance that includes a detectable label attached to a specific binding member. The attachment may be covalent or non-covalent binding and may include nucleic acid hybridization. The label allows the labeled substance to produce a detectable signal that is directly or indirectly related to the amount of analyte in a test sample. The specific binding member component of the labeled substance is selected to bind directly or indirectly to the analyte.

"Specific binding member" refers to a member of a specific binding pair (e.g., two different molecules wherein one of the molecules specifically binds to the second molecule through chemical or physical means). If the specific binding member is an immunoreactant, it can be, for example, an antibody, analyte, antigen, hapten, or complex thereof, and if an antibody is used, it can be a monoclonal or polyclonal antibody, a recombinant protein or antibody, a chimeric antibody, a mixture(s), or fragment(s) thereof, as well as a mixture of an antibody and other specific binding members. Specific examples of specific binding members include biotin and avidin, an antibody and its corresponding antigen (both having no relation to a sample to be assayed), a single stranded nucleic acid and its complement, and the like.

A "test strip" or "LFA" can include one or more bibulous or non-bibulous materials. If a test strip includes more than one material, the one or more materials are preferably in fluid communication. One material of a test strip may be overlaid on another material of the test strip, such as for example, filter paper overlaid on nitrocellulose. Additionally or alternatively, a test strip may include a region including one or more materials (e.g., media) followed by a region including one or more different materials. In this case, the regions are in fluid communication and may or may not partially overlap one another. Suitable materials for test strips include, but are not limited to, materials derived from cellulose, such as filter paper, chromatographic paper, nitrocellulose, and cellulose acetate, as well as materials made of glass fibers, nylon, dacron, polyvinyl chloride (PVC), polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied urine sample, to ensure optimal test conditions.

The material or materials can be a single structure such as a sheet cut into strips or it can be several strips or particulate material bound to a support or solid surface such as found, for example, in thin-layer chromatography and may have an absorbent pad either as an integral part or in liquid contact. The material can also be a sheet having lanes thereon, capable of spotting to induce lane formation, wherein a separate assay can be conducted in each lane. The material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site. In the following discussion test strips will be described by way of illustration and not limitation.

The support for the test strip, where a support is desired or necessary, will normally be water insoluble, frequently non-porous and rigid but may be elastic, usually hydrophobic, and porous and usually will be of the same length and width as the strip but may be larger or smaller. The support material can be transparent, and, when a test device disclosed herein is assembled, a transparent support material can be on the side of the test strip that can be viewed by the user, such that the transparent support material forms a protective layer over the test strip where it may be exposed to the external environment, such as by an aperture in the front of a test device. A wide variety of non-mobilizable and non-mobilizable materials, both natural and synthetic, and combinations thereof, may be employed provided only that the support does not interfere with the capillary action of the material or materials, or non-specifically bind assay components, or interfere with the signal producing system. Illustrative polymers include polyethylene, polypropylene, poly (4-methylbutene), polystyrene, polymethacrylate, poly (ethylene terephthalate), nylon, poly (vinyl butyrate), glass, ceramics, metals, and the like. Elastic supports may be made of polyurethane, neoprene, latex, silicone rubber and the like. Throughout this description, LFAs are described with the understanding that description of the LFAs applies to other types of test strips.

In some conventional LFAs, the test results appear as faint color changes that result in an increase in user error when reading. For example, although an LFA may output a color corresponding to a positive result, if the color is faint and/or the lighting conditions are poor, a user may interpret the test as negative. Additionally, because some conventional LFAs rely on visual cues to determine a result, the test lines that correspond to a result need to be sufficient spaced and/or sufficiently limited to avoid confusion or reading errors. Examples disclosed herein generate an improved LFA that is machine readable to provide an objective and automated result generation through an algorithm that reduces and/or otherwise eliminates false positives and/or false negatives due to human error. Additionally, the use of an LFA that does not rely on visual cues allows for more test zones closer together without the risk of misreading a result.

Because resources may be limited in particular regions of the world, dedicated LFA readers may be too expensive for use in such regions. Accordingly, examples disclosed herein provide an improved LFA that can be read using a smartphone application, as opposed to a dedicated reader. Although there are some smartphone applications that may be capable of reading the result of an LFA-based test, such smartphone applications may output inaccurate results due to poor lighting conditions, LFAs with weak visual indicators, and/or poor quality sensors on smartphones.

Examples disclosed herein generate the improved LFA to address the conventional smartphone application errors and/or human errors that correspond to inaccurate results of the conventional LFA readers. Examples disclosed herein provide a signal corresponding to the test result (e.g., one or more analog current and/or voltage values corresponding to a test result, one or more digital current and/or voltage values corresponding to the test result, one or more logic values corresponding to a test result, etc.), which provide more accurate readings than analog systems. Examples disclosed herein correspond to a machine readable LFA device that does not rely on conventional visual indicators to determine the result of a fluid sample-based test (e.g., the LFA-based test). In examples disclosed herein, the improved LFA provides machine-readable results to a smartphone application. Thus, the results are objective and readable without human interpretation, and there is no operator subjectivity, which increases the accuracy of the results. There also is no need to design and include a read window on the LFA device. As disclosed further herein, the example LFA device do not need to house a battery (e.g., a device that stores energy). For example, the LFA device is batteryless, not connected to power by wire, and is powered by the electromagnetic field generated by a user device such as a reader. Furthermore, the accurate results can be readily transmitted to an external database and/or external server such as, for example, a remote database and/or server located at or otherwise associated with an electronic medical record (EMR), a government agency, a non-government agency (NGO), a doctor's office, a hospital, a hospital information system, a laboratory information management software (LIMS) system, a stock consumption monitor, a clinic, and/or other medical facility, a medical device manufacturer, a medical organization, a health information system, and/or other external entity. In this manner, large scale test results and be generated, collected, and integrated into other healthcare systems digitally to eliminate human-based transcription errors. The examples disclosed herein also enable self-testing including, for example, by non-medical personnel because untrained self-testers do not need knowledge on how to interpret the results. Self-testing may be incorporated into over-the-counter devices. Examples disclosed herein may be incorporated into disposable point-of-care devices.

Examples disclosed herein include an LFA device that includes a wireless chip to obtain data corresponding to whether an analyte is present in a sample based on an electrical signal generated on the LFA device and to transmit the data to a reader. The determination of the test result is based on a comparison of the electrical signal to one or more thresholds. The comparison can be done on the wireless chip of the LFA and/or at an external reader. In some examples, the wireless chip obtains an analog current and/or voltage values from electrodes placed in contact with the porous membrane of the LFA device and transmits the analog current and/or voltage values to the reader via an antenna. In this manner, the reader can compare the analog values to one or more threshold to determine if a test result is positive or negative. For example, if the current and/or voltage value(s) is above a threshold, the reader determines the test corresponding to the current and/or voltage value(s) is positive. Likewise, if the current and/or voltage value(s) is below the threshold, the reader determines the test corresponding to the current and/or voltage value(s) is negative. In some examples, the wireless chip obtains analog current and/or voltage values, converts the analog values to digital values, and transmits the digital values to the reader. In this manner, the reader can compare the digital value(s) to one or more threshold to determine a test result. In some examples, the wireless chip obtains the analog voltage and/or current values and compares the values (e.g., with or without converting to digital values) to one or more threshold to generate a logic value (e.g., high or low) corresponding to a positive or negative test and transmits the test results to the reader.

Examples disclosed herein include multiple techniques for generating an electrical signal on the LFA device indicative of the presence or absence of the analyte of interest. For example, to obtain the one or more electrical signals that correspond to one or more test results, examples disclosed herein may utilize a bioelectrochemical mechanism (e.g., a device that generates energy) at the test and/or control lines of the LFA device. As further described below, a bioelectrochemical mechanism includes a bioelectrochemical cell (e.g., a physical cell or structuring the porous membrane to act as the physical cell) that, when a target analyte is present, generates an electrical signal at the porous membrane. The bioelectrochemical cell may be known as or otherwise include a potentiometric cell, a concentration-cell, a fuel cell, a biofuel cell, etc. In some examples, the bioelectrochemical cell generates the electrical signal due to one or more bioelectrochemical reactions that occur on the porous membrane. The wireless chip of the LFA device can measure the electrical signal by sensing a current and/or a voltage drop between electrodes of the bioelectrochemical cell placed in contact with the porous membrane. In other examples, the LFA device may include an circuit completion mechanism at the test and/or control lines of a LFA device, to generate the electrical signal. As further described below, a circuit completion mechanism generates a short circuit at a test zone when a target analyze is present in a sample. For example, the circuit completion mechanism may amplify a substance (e.g., silver) around an immobilized molecule (e.g., gold) at a test zone when a target analyte is present. In this manner, the wireless chip can generate a voltage and measure whether current flows from one side of the test zone to another (e.g., when the short circuit is generated) to identify whether the target analyte is present.

In some examples of the bioelectrochemical cell disclosed herein, one half the bioelectrochemical cell is attached to a test zone (e.g., test line, test region, etc.) and/or control zone (control line) of the porous media (e.g., a membrane, a paper, and/or other compartment-free or compartmentless substrate) of the LFA. In some examples, the bioelectrochemical cell may be a piece of paper that has been impregnated with a solution of glucose and a redox-species (e.g., potassium ferricyanide $K_3[Fe(CN)_6]^{3-}$, or ferrocene or a ferrocene derivative) and dried. Additionally, examples disclosed herein label (e.g., attach, couple, etc.) an enzyme (e.g., glucose oxidase (GOx)) to antibodies analytes, and/or antigens on the conjugate pad. In this manner, if the antibodies analytes, and/or antigens coupled to GOx attach to a target analyte, the immobilized antibodies, analytes, and/or antigens corresponding to the target analyte at the test zone attaches and immobilizes the GOx. Because one half of the bioelectrochemical cell is attached to the test zone, the GOx reacts with the solution of the bioelectrochemical cell to oxidize the glucose of the bioelectrochemical cell as shown in the below chemical reaction Processes 1-3, where (Ox) and (Red) refer to the reduced or oxidized state of the enzyme, respectively.

$$\text{Glucose+GOx (Ox)} \Rightarrow \text{Gluconolactone+GOx (Red)} \quad \text{(Process 1)}$$

$$\text{GOx (Red)}+O_2 \Rightarrow \text{GOx (Ox)}+H_2O_2 \quad \text{(Process 2)}$$

$$\text{Gluconolactone}+H_2O \Rightarrow \text{Gluconic Acid} \quad \text{(Process 3)}$$

Additionally, the below Processes 4-5 illustrate chemical reactions, where cofactor flavin adenine dinucleotide (FAD) and $FADH_2$ refer to the oxidized or reduced state of the enzymes active center, respectively.

$$\text{GOx}(FADH_2)+O_2 \Rightarrow \text{GOx(FAD)}+H_2O_2 \quad \text{(Process 4)}$$

$$\text{GOx(FAD)+Glucose} \Rightarrow \text{GOx}(FADH_2)\text{+Gluconolactone} \quad \text{(Process 5)}$$

Although examples disclosed herein refer to GOx as the enzyme used to generate a product (e.g., hydrogen peroxide ($H_2O_2$)) that corresponds to current flow and/or release/movement of electrons, examples disclosed herein may implemented using additional and/or alternative enzymes. Examples disclosed herein may utilize amino acid oxidase, Nicotinamide adenine dinucleotide phosphate (NADPH) oxidase, alcohol oxidase, galactose oxidase, and/or any other oxidase as an enzyme used to generate a product (e.g., hydrogen peroxide) that facilitates a release and/or movement of electrons. In some examples, based on the enzyme used, molecules other than glucose are included to facilitate the reaction to generate hydrogen peroxide.

In some examples, an enzymatic reaction with a natural mediator (electron acceptor) (e.g., oxygen) can be used for a bioelectrochemical cell. In such an example, glucose oxidizing to gluconolactone and $FADH_2$ oxidizing to FAD, thereby resulting in a product (e.g., $H_2O_2$ (hydrogen peroxide)). Additionally or alternatively, glucose can oxidize and reduce oxygen in the presence of glucose oxidase to cause $C_6H_{12}O_6$ and oxygen ($O_2$) to react and generate $C_6H_{10}O_6$ and $H_2O_2$ (e.g., hydrogen peroxide). In some examples, the electrodes may be made of a metal (e.g., copper, titanium, brass, silver, platinum, etc.) graphite, or a screen printed carbon electrodes doped with ferrocyanide. In this manner, the product (e.g., $H_2O_2$) is reduced and oxidation of the metal or ferrocyanide of the electrode occurs by release of electrons. In later case ferrocyanide $[Fe(CN)_6]^{4-}$ reacts to $[Fe(CN)_6]^{3-}$. Released electrons can be measured by a processor (e.g., using a current and/or voltage measurement). Copper surface normally oxidized by air to $Cu_2O$ (Cu(I)). $Cu_2O$ is oxidized to CuO (Cu(II)) by reduction of $H_2O_2$.

Because the product (e.g., hydrogen peroxide) is generated at the test line and/or control line but not immobilized at the test line and/or control line, the product may start to flow toward a wicking pad of the LFA device. Accordingly, some examples disclosed herein may include a mechanism to arrest (e.g., slow or stop) the flow to maintain the product or portions of the product in the test zone at or near the test and/or control line until the test is read. The mechanism to arrest flow may be used in any disclosed example. Some examples disclosed herein slow the flow by shearing, pinching, and/or cutting (e.g., partially or fully) the porous membrane to arrest the flow. Such examples may include a mechanical device that the user can control (e.g., move, slide, pivot, twist, rotate, etc.) to cut the porous membrane. Some examples disclosed herein apply a substance (e.g., chemical substance, glue, gel, etc.) that is more viscous than the buffer to slow and/or stop the flow. In some examples, the electrodes may be set in place after/during the application of the mechanism to arrest flow to allow the product (e.g., hydrogen peroxide) to react with the electrode(s) after the flow has stopped or has been slowed to generate a strong electrical signal (e.g., corresponding to the electron flow caused by the reaction).

In other examples, alternative reactions may be implemented with a bioelectrochemical cell. For example, an amperometric redox-reaction without enzymes can be used for a bioelectrochemical cell. For example, an amperometric signal of an LFA can be measured without the GOx enzyme because the gold of the AuNP may act as a catalyzer (e.g., where the GOx in the conjugate is replated with AUNP). In such examples, thiosulfate may be used to improve the signal as shown below in Processes 6-8. In the below Process 11, thiosulfate, ferricyanide, and KBr or KCl react and the AuNP will catalyze reduction to the ferrocyanide to create an electronic signal. The KBr or KCl may be included in the buffer and/or may be dried in a portion of the porous membrane and resuspended with a buffer.

$$\text{(Oxidation) } 2S_2O_3^{2-} \Rightarrow S_4O_6^{2-} + 2e^- \quad \text{(Process 6)}$$

$$\text{(Reduction) } [Fe(CN)_6]^{3-} + e^- \Rightarrow [Fe(CN)_6]^{4-} \quad \text{(Process 7)}$$

$$2[Fe(CN)_6]^{3-} + 2S_2O_3^{2-} \Rightarrow 2[Fe(CN)_6]^{4-} + S_4O_6^{2-} \quad \text{(Process 8)}$$

Alternatively, the below Processes 9-11 illustrate alternative chemical reactions for GOx-glucose oxidation. As shown in the previous processes, oxygen can re-activate or re-oxidize GOx to its active form. Although Processes 9-11 are described in conjunction with ferricyanide, the Processes 9-11 may be used with other substances in their oxidized form (e.g., quinones, ferrocenes, osmium complexes, etc.). The quinones, ferrocenes, osmium complexes, etc. may be included in the buffer and/or may be dried in a portion of the porous membrane and resuspended with a buffer.

$$\text{Glucose} + \text{GOx(Ox)} \Rightarrow \text{Gluconolactone} + \text{GOx(Red)} \quad \text{(Process 9)}$$

$$\text{GOx(Red)} + 2[Fe(CN)]^{3-} \Rightarrow \text{GOx(Ox)} + 2[Fe(CN)]^{4-} \quad \text{(Process 10)}$$

$$\text{Gluconolactone} + H_2O \Rightarrow \text{Gluconic Acid} \quad \text{(Process 11)}$$

Processes 4 and 11 result in a decrease in the pH level of the solution (e.g., to acidic regime in case of a low buffering system), which corresponds to an electromotive force with respect to an electrode placed next to a test line of an LFA, where a GOx reaction does not occur. A change of the pH level will occur in low concentrated buffer solutions and results in a measurable Nernst voltage and/or current.

Within a redox-cycle of GOx, an electron can be transferred to reduce $[Fe(CN)_6]^{3-}$ to $[Fe(CN)_6]^{4-}$ at one half of the bioelectrochemical cell. The ferricyanide molecule acts as an electron mediator and can finally diffuse to the electrode. The concentration difference of an electrode at the upper portion of a cell and an electrode at the bottom portion of the cell creates a cell voltage described by the Nernst equation $$E = 0.059\ \text{V} + \log\frac{[Fe(CN)_6]^{3-}}{[Fe(CN)_6]^{4-}} \text{ and/or } E = 0.059\ \text{V} + \log\frac{[H_3O^+]_{cell\_bottom}}{[H_3O^+]_{cell\_top}}.$$

Accordingly, the porous media in conjunction with the cell and/or the electrode generate an electrical signal (e.g., a voltage or current) when a target analyte is present in a sample. Examples disclosed herein measure a voltage and/or current from a cell (e.g., from one half to the other half) corresponding to current through the potentiometric cell to determine whether or not the test is positive (e.g., the corresponding target analyte is present in a sample) or negative (e.g., the corresponding target analyte is not present in a sample), thereby eliminating the need for a visual indicator. There may be other combinations of elements and/or reduction agents other than the examples listed above that may be additionally or alternatively used when implementing a bioelectrochemical cell. An LFA that leverages a reaction that results in detection of ions in a solution based on electric current or charges in electric current (e.g., an amperometric measurement) is herein referred to as an amperometric-based LFA. An LFA that leverages a detection of an electric potential difference between two electrodes (e.g., a potentiometric measurement resulting from a redox reaction) is herein referred to as a potentiometric-based LFA.

In some examples disclose herein, the media (e.g., membrane, paper, and/or substrate) of the lateral flow immunoassay device can act as a bioelectrochemical cell. For example, instead of using a paper dried with glucose and a redox species to act as a bioelectrochemical cell. A liquid assay buffer may be applied to the lateral flow immunoassay device that includes glucose and a redox species. In some examples, the buffer can dilute the sample and include the glucose and a redox species to facilitate the reaction that results in a current or voltage. In such examples, the membrane of the lateral flow immunoassay device acts as the salt-bridge. In this manner, if the immobilized antibodies analytes, and/or antigens corresponding to the target analyte at the test zone attaches immobilize the GOx, the GOx will react with the glucose and redox species of the assay buffer to diffuse electrons to a zone of the media outside of the test zone, thereby creating a voltage and/or current. Accordingly, the bioelectrochemical cell is based on the target zone and a zone outside the target zone. Thus, a first electrode can be placed at the test zone and a second electrode can be placed at a zone outside of the test zone and a voltage and/or current can be measured between the two test zones to determine if the target analyte is present. As used herein, a bioelectrochemical cell is a cell that converts chemical energy of a fuel and an agent (e.g., an oxidizing agent) into electricity through a pair of redox reactions. A bioelectrochemical cell could be a biofuel cell (e.g., a fuel cell that uses enzymes as a catalyst to oxidize its fuel), a concentration cell (e.g., an electrolytic cell including two half-cells with the same electrodes that creates a voltage and/or current when the two half-cells have different concentrations (e.g., GOx Glucose reaction at one electrode and no reaction at other electrode)), a galvanic cell (e.g., including two different metals immersed in electrolytes connected by a salt bridge or porous media), and/or any other cell that converts chemical energy into electricity.

As disclosed above, in some examples, the LFA device may use a circuit completion mechanism at the test and/or control lines of a LFA device, to generate or measure an electrical signal corresponding to a test result. For example, the machine readable LFA device has a test zone that acts like an electrical switch. In such examples, the conjugate pad includes gold nanoparticles labeled with antibodies analytes, and/or antigens that correspond to a target analyte. In this manner, if a sample includes the target analytes, the target analytes attach to the gold labelled antibodies, analytes, and/or antigens and immobilize at a test zone by corresponding immobilized antigens, analytes, and/or antibodies. An autocatalytic silver enhancement (e.g., silver ion and reducing agent, such as hydroquinone, aminophenols, ascorbic acid) is applied to the test zone so that the silver reacts with the gold and amplify in size. When the silver amplifies beyond a certain size, the amplified silver attached to each gold nanoparticle on the test zone contact with one another, thereby creating a connection, increasing conductivity, reduced resistance, and/or short circuit between the electrodes. Examples disclosed herein can apply an electrical connection to each side of a test zone and apply a voltage to one side of the electrical connections. If the target analyte is present, the silver amplifies to create the connection, increased conductivity, reduced resistance, and/or short circuit and the application of voltage results in current flowing from one electrical connection to the other. Accordingly, examples disclosed herein determine that the target analyte is present in a sample (e.g., corresponding to a positive test result) by measuring a signal (e.g., the current flow and/or the resistance between the electrical connections to the test line (e.g., the resistance of a short circuit is low and the resistance of an open circuit is high (infinite))). If the measured signal has a current above a current threshold or a corresponding resistance below a resistance threshold, examples disclosed herein flag the test as positive for the corresponding target analyte and if the measured signal has a current below the current threshold or a corresponding resistance above the resistance threshold, examples disclosed herein flag the test result as negative for the corresponding target analyte, thereby eliminating the need for a visual indicator.

Alternatively, the silver amplification reaction (reduction of silver by oxidation of reducing agent releases electron $e^-$ and a proton $H^+$ which recombines with $H_2O$ to $H_3O^+$) creates $H_3O^+$ ions which alter the pH value of a low buffered reaction solution. One of the bioelectrochemical cells where the silver amplification takes place at the upper part of the cell creates a voltage which is described by the Nernst equation $$E = 0.059\ \text{V} + \log\frac{[H_3O^+]_{cell\_1}}{[H_3O^+]_{cell\_2}},$$

where $cell_2$ and $cell_1$ ($cell_2$=top cell, $cell_1$=bottom cell) refer to the concentrations of $H_3O^+$ ions in the specific cells. The voltage and/or current of the cell can be measured by the wireless chip.

Because the LFA device may correspond to one or more specific durations of time that a user should take a particular action (e.g., a duration of time to apply the sample and/or a buffer, a duration of time to obtain results after applying a sample, a duration of time to scan the LFA device with a reader, a duration of time to move a mechanical piece of the LFA device, etc.), examples disclosed herein including mechanisms and processes to track time and/or guide a user to perform one or more steps. For example, after a sample and/or buffer is applied to an LFA, the user may need to wait for a first duration of time before obtaining the results. Examples disclosed herein may include a timer at the LFA device and/or at the reader to track the duration(s) of time to guide the user through the testing process. In some examples, the timer is powered by the current and/or voltage generated by the bioelectrochemical cell. In some examples, the LFA device may transmit the timing information to the LFA reader and the LFA reader may display and/or otherwise indicate one or more durations of time to the user. In some examples, the LFA reader may track durations of time based on confirmations from the user and guide the user as to when to perform particular tasks to ensure that a task is not performed too early or too late (e.g., reading a result too early or too late, scanning the LFA too early or too late, adjusting the LFA device too early or too late, etc.). By providing a reader to guide a user through the testing product, LFA devices can be operated by the user with less training and/or may be performed by a user with less education level. Additionally, the reader can be implemented by the patient for self-testing by following the guide presented on the reader.

FIG. 1A is an example environment 100 including an example machine readable LFA generator 102 to generate an example machine readable LFA chip, strip, or LFA device 104 (illustrated in an overhead view). The example machine readable LFA device 104 includes an example sample pad 106, an example conjugate release pad 108, an example porous media 109, an example test area 110, example bioelectrochemical cells 111*a-n*, an example wicking pad 112, an example inlet 113, an example wireless chip 114, and an example antenna 115. The environment 100 of FIG. 1A further includes an example user device or reader 116 to determine the test results (e.g., diagnostic test results) of a sample being applied to the example machine readable LFA device 104. The example reader 116 includes an example machine readable LFA reader application 117, an example antenna 118, and an example user interface 120. Although the example of FIG. 1A determines test results based on the bioelectrochemical cells 111*a-n*, FIG. 1A may be described in conjunction with other techniques for determining test results based on an electrical signal, as further disclosed herein.

Figure 3A:
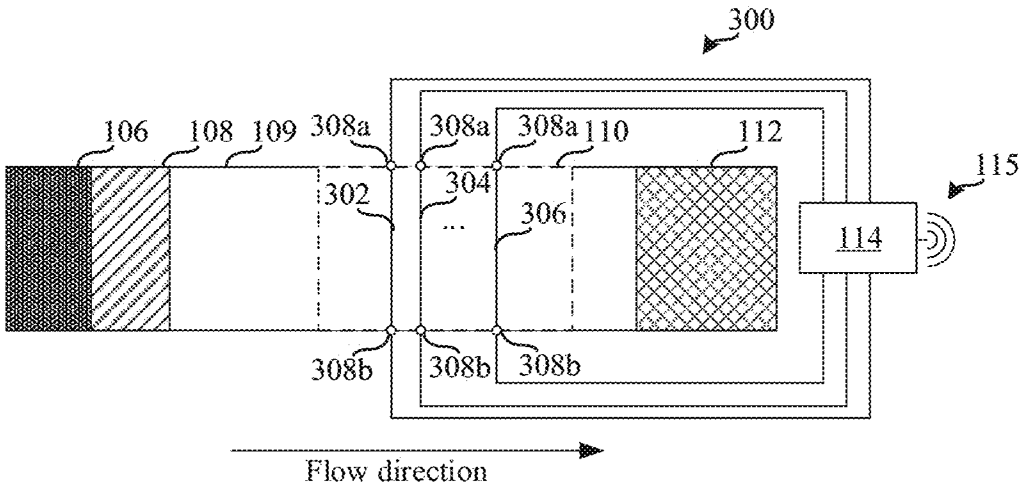
FIG. 3A illustrates an alternative example machine readable lateral flow immunoassay that may be generated by the example machine readable lateral flow immunoassay generator of FIG. 1A.

The example machine readable LFA generator 102 of FIG. 1A generates the example machine readable LFA device 104 (and/or the example machine readable LFA device 300 of FIG. 3A). For example, the machine readable LFA generator 102 generates the machine readable LFA device 104 to include the example sample pad 106, the example conjugate release pad 108, the example porous media 109, the example test area 110, the example bioelectrochemical cells 111*a-n*, the example wicking pad 112, the example inlet 113, the example wireless chip 114, the example antenna 115, and/or wires or etches included in a housing structure (not shown). The number of test, types of test (e.g., pregnancy, Ebola, HIV, influenza, covid, cancer, sexually transmitted diseases (STDs), etc.), number of control zones, types of control zones (e.g., positive control, negative control, etc.), and/or type of machine readable LFA is based on instructions from a user and/or manufacture. For example, if a user wants the example machine readable LFA device 104 to include a single test for pregnancy, the machine readable LFA generator 102 generates the example conjugate region to include antibodies, analytes, and/or antigens corresponding to a target analyte that corresponds to pregnancy, the antibodies, analytes, and/or antigens labelled with a particular molecule (e.g., gold nanoparticles, GOx, etc.). In such an example, the machine readable LFA generator 102 generates the test area 110 to include immobilized antibodies, analytes, and/or antigens to bind or otherwise attach to the target analytes and a bioelectrochemical cell (e.g., paper impregnated with an enzyme substrate (e.g. glucose) and/or a reducing agent (e.g. hydroquinone, aminophenol, vitamin C (e.g., ascorbic acid included in Vitamin C), etc.), and/or an electron mediator or a redox-species (e.g. potassium ferricyanide, ferrocene, oxygen, a ferrocene derivative, etc.) including a first half to attach to the test area 110. Additionally, the example machine readable LFA generator 102 generates, or otherwise attaches, the wireless chip 114 to attach to the bioelectrochemical cell to determine whether a sample (e.g., a biological sample) is positive or negative for the target analytes corresponding to pregnancy. The example machine readable LFA generator 102 is further disclosed in conjunction with FIG. 4.

The example machine readable LFA device 104 of FIG. 1A is a bioelectrochemical cell-based LFA (e.g., a concentrations cell with Nernst voltage sensing) that includes the example bioelectrochemical cells 111*a-n*. However, the machine readable LFA device 104 may be alternative devices that can obtain data related to a test result on the LFA 104. For example, as further disclosed below in conjunction with FIG. 3A, the example machine readable LFA device 104 could alternatively be a circuit completion-based LFA device (e.g., an electrical short circuit through a test line with low resistance). In some examples, the example machine readable LFA device 104 is a non-visual indicating biosensor device. For example, the LFA device 104 may not output a visual indication to a user (e.g., because no gold nanoparticles are present on the device) and/or the visual indication is not visible to a user (e.g., because the housing covers the porous media where the visual indications may be implemented). In some examples, the LFA device 104 is a non-visual indicating circuit completion device. In some examples, the LFA device 104 is a visual indicating circuit completion device and/or biosensor device that provides a visual indication of the results and is capable of transmitting the results wirelessly to a reader. The LAF device 104 may be a point-of-care device and/or a rapid diagnostic device containing an application-specific integrated circuit (e.g., the example wireless chip 114).

The example machine readable LFA device 104 of FIG. 1A is a device that includes the sample pad 106 (e.g., a sample pad, a sample region, a sample area, a sample zone, etc.). For example, the LFA device 104 may be a porous membrane device, a porous media device, a fluid transporting media device, a test strip device, a lateral flow test strip device, and/or any fluid sample device. The sample pad 106 is structured to act as a sponge to hold a sample of fluid applied to the sample pad 106. In some examples, the sample pad 106 includes buffer components (e.g., salts, surfactants, etc.) to ensure that target analytes that may be in the sample are capable of binding with components of the conjugate release pad 108. When the sample pad 106 is soaked, the fluid held in the sample pad 106 flows to the conjugate release pad 108. The conjugate pad 108 includes a labeled substance or conjugate configured to bind a target analyte. For example, the conjugate release pad 108 includes conjugates or probes (e.g., antibodies specific to one or more target analyte) labeled detectable labels, tags, linkers, antibodies, analytes, antigens, GOx, gold nanoparticles, etc. The target analyte is a component that corresponds to a particular condition or disease. Accordingly, presence of the target analyte in the sample corresponds to presence of the corresponding condition and/or disease in the patient who provided the sample. If the sample includes the one or more of the target analytes, the conjugates and/or probes labelled with the GOx, gold nanoparticles, etc., attach to the corresponding target analytes. The sample (e.g., including the probes if corresponding target analytes are present in the sample) continues to flow through the example porous media 109 of the machine readable LFA device 104 toward the wicking pad 112.

While the sample flows across the media 109 of FIG. 1A, the sample flows across the test area 110. The media 109 may be a porous membrane, a nitrocellulose membrane, a paper, and/or other substrate including a compartment-free substrate, etc. that propagates the flow of the biological sample and/or liquid buffer. The test area 110 includes test zones (e.g., test lines, test area, test region, etc.) and/or control zones (e.g., control lines, control area, control region, etc.). The test zones include specific immobilized antibodies, analytes, or antigens that react with the corresponding target analytes attached with the probes and/or conjugates. Accordingly, when the target analyte corresponding to a particular test zone is present in the sample, the GOx and/or gold nanoparticles immobilize at the particular test zone. In some examples, the test zones of the LFA 104 corresponds to different conditions or diseases, known as multiplexing. Multiplexing includes structuring multiple test zones or test lines to detect multiple marks (e.g., multiple types of antibodies/antigens/analytes) in one sample. Multiplexing has applications, for example, in a single diagnostic test that could test for multiple types of venereal diseases. In some examples, the test area 110 includes control zones that immobilize specific, and/or excess, conjugates flowing past the control zones. The control zones correspond to targets which have been dried to the porous media 109 to signify that the test is ready to be read (e.g., when the test is complete).

The test area 110 of FIG. 1A further includes the example bioelectrochemical cells 111*a-n* (e.g., concentration cells). FIG. 1A illustrates a portion of the bioelectrochemical cells 111*a-n*. Other portions are illustrated in FIGS. 1B-2E and/or 2I-2K. In some examples, the potentiometric cells 111*a-n* are pieces of paper or other substrate impregnated with an enzyme substrate (e.g. glucose) and/or a reducing agent (e.g. hydroquinone, aminophenol, ascorbic acid included in vitamin C, etc.), and/or an electron mediator or a redox-species (e.g. potassium ferricyanide, ferrocene, oxygen, a ferrocene derivatives, etc.). However, the bioelectrochemical cells 111*a-n* can be any type of bioelectrochemical cell, as described above in conjunction with the above Processes 1-11. When GOx (which oxidizes glucose) or gold nanoparticles (silver nitrate reduction (e.g., vitamin C and/or another reducing agent) via autocatalysis) attaches to the test zones and/or control zones, the corresponding bioelectrochemical cells 111*a-n* are activated by generation of a voltage according to the Nernst equation, which can be read out via the wireless chip 114. Accordingly, the wireless chip 114 uses example bioelectrochemical cells 111*a-n* to perform a bioelectrochemical measurement, where the wireless chip 114 passively measures the potential between two different parts of the biofuel cells 111*a-n* using two electrodes. In some examples, the bioelectrochemical cells 111*a-n* are fluidically coupled (e.g., attached) to the test and/or control zones during manufacturing. In some examples, the bioelectrochemical cells 111*a-n* are separate from the test and/or control zones during manufacturing and the example LFA device 104 includes a mechanical device to automatically and/or manually press the bioelectrochemical cell into contact (e.g., fluidically contact) with the test and/or control zones when a test is to be performed (e.g., automatically when a sample is applied to the LFA 104 and/or manually via a user interference to press the bioelectrochemical cell into contact with the zones).

The test area 110 of FIG. 1A further includes the example wicking pad 112. The example wicking pad 112 of FIG. 1A is an absorbent material that wicks the liquid through the LFA. In some examples, the wicking pad 112 includes cellulose filters. The wicking pad 112 prevents backflow of the liquid. Also, in some examples, the wicking pad 112 acts as a waste container.

The test area 110 further includes the inlet 113 of FIG. 1A. The example inlet 113 of FIG. 1A is structured to allow water or another buffer solution applied to the sample pad 106 to flow to the wicking pad 112. In some examples, the water and/or buffer is enclosed in a holding device (e.g., a frangible enclosure such as a bag) and the user presses and/or moves a component of the LFA device 104 to cause the holding device to release the buffer (e.g., by breaking the bag). In some examples, the sample pad 106 may be more than one sample pads (e.g., one for the sample and another for the water/buffer and/or further reagents). When the water and/or buffer flows past the bioelectrochemical cells 111_a-n_, the water and/or buffer resuspends the dried reagents to cause the current to flow if the test and/or control zone has attached to GOx and/or gold nanoparticles (e.g., based on the mixing of the conjugate with the enzyme substrate, the reducing agent, and/or the electron mediator of the bioelectrochemical cells 111_a-n_). A center area (e.g., the constricted area in FIG. 2A) between a first portion (e.g., the top portion in FIG. 2A) and a second portion (e.g., the bottom portion in FIG. 2A) of the bioelectrochemical cells 111_a-n_ acts as a salt-bridge against diffusion induced homogenization of a concentration gradient, thereby causing electrons lost in the first portion of the bioelectrochemical cells 111_a-n_ (e.g., due to the reactions that occur when the target analyte and corresponding conjugate is suspended in the test zone or control zone) to flow toward the second portion of the bioelectrochemical cells 111_a-n_, corresponding to a measurable voltage drop and/or current from the first portion of the bioelectrochemical cells 111_a-n_ to the second portion of the bioelectrochemical cells 111_a-n_. Additionally or alternatively, the paper/membrane type could reduce diffusion.

The example machine readable LFA device 104 further includes the example wireless chip 114. The wireless chip 114 is a near field communication (NFC) chip. Accordingly, the wireless chip 114 can obtain power and/or communicate with the reader 116 via NFC communication protocols. Alternatively, the example wireless chip 114 may be a radio frequency identification (RFID) chip or any other type of wireless chip. The wireless chip 114 includes pins coupled to connectors (e.g., wires, etches, etc.) that couple to electrodes (e.g., directly or via a front-end device, as further described below). The electrodes connect to the two ends of each bioelectrochemical cell 111_a-n_ and/or on different sections of the porous membrane 109. In this manner, if voltage and/or current is generated by the bioelectrochemical cell 111_a-n_, a voltage drop and/or current between the two electrodes (e.g., connected to the opposite sites of the bioelectrochemical cell or placed in different locations on the porous membrane 109) will be higher than a threshold. In some examples, the generated voltage and/or current can be used to power the wireless chip 114 (e.g., to provide power for storing the results of the test at the wireless chip 114). The example wireless chip 114 includes hardware, software, and/or firmware capable of measuring a current, an electromotoric force, or the voltage drop and/or current to determine if a target analyte is present in a sample. The wireless chip 114 may include an ASIC to encode manufacturing and/or identification information. The example wireless chip 114 is powered by the example antenna 115. When the example reader 116 generates a magnetic field within a threshold distance to the example antenna 115, a current is generated at the antenna 115 and the corresponding energy is used to power the wireless chip 114. Once powered, the wireless chip 114 can transmit identification information (e.g., device identifier, test identifier, serial number, product code, etc.) to the example reader 116 and/or may transmit measurements corresponding to test results (e.g., analog and/or digital values corresponding to voltage and/or current measurements taken at the LFA device 104). In some examples, the communication between the wireless chip 114 and the reader 116 is encrypted using an encryption technique known by both the wireless chip 114 and the reader 116. In some examples, the wireless chip 114 may flag each test zone and/or control zone as positive or negative based on the measured current, electromotoric force, and/or voltage drop, store the results corresponding to the flag(s), and/or use the antenna 115 to transmit the results. Additionally, the example wireless chip 114 may transmit identification information corresponding to an LFA identifier, identifiers for the test and/or control zones, etc., with the results. In some examples, the wireless chip 114 is coupled to a circuit completion based LFA. Although the example of FIG. 1A includes the example wireless chip 114 as part of the example LFA 104, the wireless chip may be integrated in an external device. In such examples, the LFA 104 may include a component (e.g., an interface) that allows the electrodes of the LFA 104 to connect to the wireless chip 114. In this manner, design of the LFA 104 can be simplified to reduce the size and/or cost of the LFA 104 and multiple LFAs can be connected to the wireless device 114 to transmit test results to the example reader 116. Operation of the wireless chip 114 in conjunction with a circuit completion based LFA is further disclosed below in conjunction with FIG. 3A. The example wireless chip 114 is further disclosed below in conjunction with FIG. 5.

The example reader 116 of FIG. 1A is a smartphone that includes the machine readable LFA reader application 117, the example antenna 118, and the example user interface 120. Alternatively, the example reader 116 may be a tablet, a personal digital assistant, a laptop, a standalone LFA reader device, and/or any other processing device that includes, or is otherwise in communication with, the example machine readable LFA reader application 117, the example antenna 118, and/or the example user interface 120. The example machine readable LFA reader application 117 is an application that can be installed, downloaded, and/or coded within the example reader 116. In some examples, the example machine readable LFA reader application 117 can be supplied via a near field communication tag or Bluetooth device.

In some examples, the reader 116 can be split into multiple readers. In such examples, a first reader 116 obtains the information from the LFA 104 and guides the user through the process with the LFA 104, and a second reader 116 obtains the test results from the LFA 104. For example, in a hospital, a hospital information system, a LIMS system, a stock consumption monitor, a clinic, a testing site, etc., the first reader may guide a first user to use a first LFA reader to get samples, once the samples are taken, the first reader may communicate with the second reader to send the LFA device information and initiate the timer at the second reader for the when the test is ready. In this manner, the first user can provide the LFA device to the second user and the second user can scan the LFA devices when ready using the second reader.

The example machine readable LFA reader application 117 of FIG. 1A instructs components of the reader 116 to generate an electromagnetic signal at various points in time to (a) obtain identification information from the LFA device 104 at a first time, (b) obtain the identification information from the LFA device 104 a second time prior to obtaining the results to verify that the correct device is being read, and (c) obtain the results (e.g., one or more digital voltages and/or currents corresponding to the results) from the LFA device 104. The example LFA reader application 117 causes the electromagnetic field to be generated a second time to verify the identification information to ensure that the user is reading the test from the correct LFA device (e.g., when reading multiple tests concurrently). The example machine readable LFA reader application 117 identifies the results of an LFA-based test by interacting with the wireless chip 114 (e.g., receiving a wireless signal identifying the results of a test). For example, the machine readable LFA reader application 117 controls the components of the reader 116 to obtain identification information corresponding to the machine readable LFA device 104 and/or test results via a NFC, RFID, etc. signal transmitted from the wireless chip 114. In some examples, the LFA reader application 117 determines information based on the obtained identification information. For example, the LFA reader application 117 can determine if the test has already been read, the type of test that is being performed, an algorithm for identifying and/or categorizing the results of the test, whether the test has expired or recalled, etc. The algorithms (e.g., corresponding to how and when to read one or more electrical signals from a particular LFA device) may be stored locally at the reader 116 and/or may be configured, reconfigured, updated, etc. remotely (e.g., via a patch, an update, remote instructions, etc.). Once the test results are obtained (e.g., the samples from the LFA device 104), the machine readable LFA reader application 117 determines if the test is ready (e.g., based on the flags of corresponding to the control zones) and, if ready, determines the results of the test based on a corresponding algorithm (e.g., using voltage and/or current samples from the test lines) and displays the results using the example user interface 120, stores the results in a local database, and/or transmits the results to a monitoring entity for monitoring and/or statistical analysis. In this manner, the manufacturer or other party can process the results, perform diagnostics, and/or identify if a particular LFA device may be counterfeited (e.g., if more than a threshold number of results corresponding to the same identification information has been determined). In some examples, the LFA reader application 117 transmits raw data. In some examples, the LFA reader application 117 obtains (e.g., from the wireless chip 114) and/or determines (e.g., based on identification information from the wireless chip 114) various other contextual information including lot number, expiration date, expiry date, test information, signal quality information, chain of custody, etc. Additionally or alternatively, in some examples, the LFA reader application 117 transmits processed data or data resulting from one or more levels of analysis. The example machine readable LFA reader application 117 is further disclosed below in conjunction with FIG. 6.

The example antenna 118 of the example reader 116 of FIG. 1A wirelessly powers and/or communicates with the example wireless chip 114 (e.g., via the example antenna 115). For example, based on instructions from the example machine readable LFA reader application 117, the antenna 118 emits a magnetic field to power the example wireless chip 114 and receives wireless information (e.g., identifiers, test results, etc.) from the example wireless chip 114.

Figure 1B:
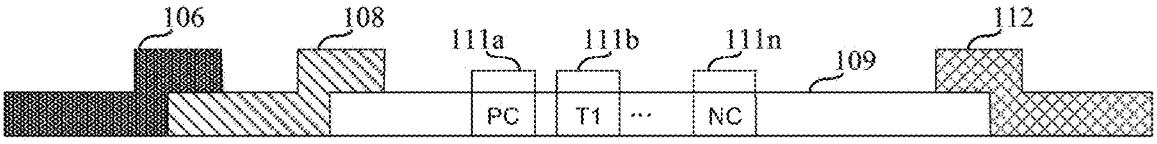
FIG. 1B is a side view of the example machine readable lateral flow immunoassay of FIG. 1A.

FIG. 1B is a side view of the LFA components of the LFA device 104 of FIG. 1A. FIG. 1B includes the example sample pad 106, the example conjugate pad 108, the example porous media 109, portion(s) of the example bioelectrochemical cells 111*a*-111*n*, and the example waste pad 112 of FIG. 1A. The example bioelectrochemical cells 111*a-n* are connected to the example wireless chip 114 of FIG. 1A via electrodes, as described above in conjunction with FIG. 1A.

Figure 2A:
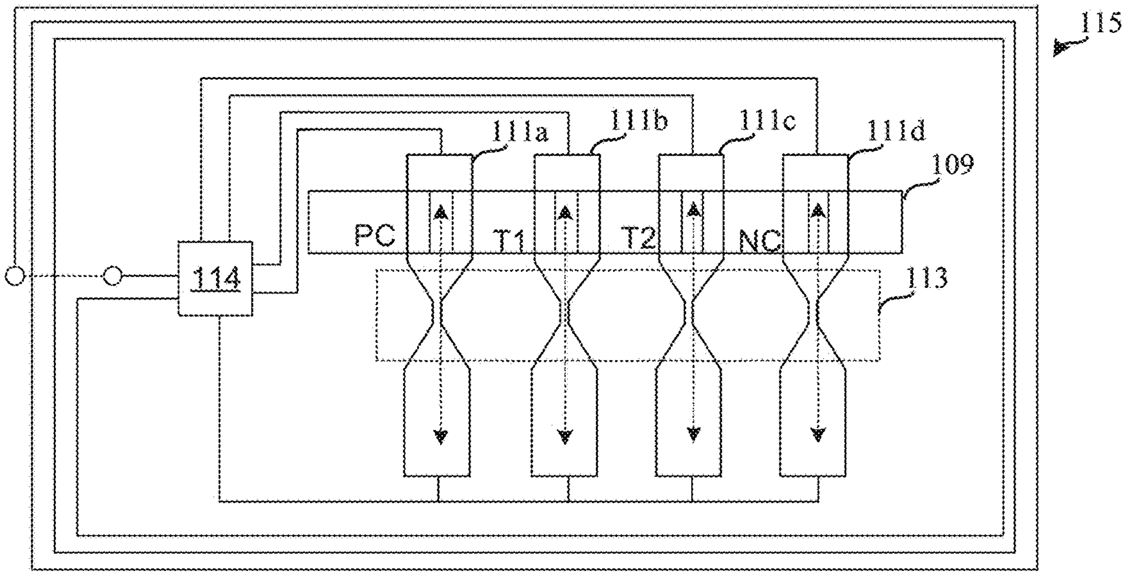
FIG. 2A illustrates an example implementation of part the machine readable lateral flow immunoassay of FIG. 1A.

FIG. 2A illustrates an example implementation of parts of the machine readable LFA device 104 of FIG. 1A when implementing the example bioelectrochemical cells 111*a-n* of FIG. 1A to generate an electrical signal corresponding to a test analyze by an enzymatic reaction. The example of FIG. 2A includes the example porous media 109, example bioelectrochemical cells 111*a-d* (e.g., corresponding to the bioelectrochemical cells 111*a-n* of FIG. 1A), the example inlet 113, the example wireless chip 114, and the example antenna 115 of FIG. 1A. Although the example porous media 109 has two control lines, two test lines, and four bioelectrochemical cells 111*a-d*, the porous media 109 may have any number of test lines, control lines, and/or bioelectrochemical cells. Additionally or alternatively, other techniques may be used to obtain an electrical signal corresponding to a test result (e.g., a circuit completion technique, utilizing the porous membrane 109 as the bioelectrochemical cell, etc.), as further described below.

The example porous media 109 of FIG. 2A is structured with two test lines (e.g., T1 and T2) and two control lines (e.g., positive control (PC) and negative control (NC)). The negative control line includes immobilized antibodies and/or antigens to couple to corresponding target analytes that couple to the immobilized antibodies when a sample is applied to the sample pad 106. The negative control line is included to verify that the current generated by the attached bioelectrochemical cell 111*d* is strong enough for a valid test measurement. For a test to be valid, the amount of voltage and/or current across the bioelectrochemical cell 111*d* over the negative control line should be lower than a threshold.

The positive control line includes immobilized antibodies, analytes, and/or antigens that couple to specific, and/or excess, conjugates labelled with GOx and/or gold nanoparticles and/or probes labelled with GOx and/or gold nanoparticles flowing from the conjugate pad 108 toward the wicking pad 112. When a sample flows toward the wicking pad 112, the positive control line is the last section to attach to the conjugates and/or probes, resulting in a voltage and/or current generation by the bioelectrochemical cell 111*a*. In this manner, the reader 116 knows if the test is ready when the result of a voltage and/or current measurement of the bioelectrochemical cell 111*a* results in positive (e.g., more than a threshold amount of voltage and/or current). The example test lines T1 and T2 each have immobilized antibodies, analytes, and/or antigens that correspond to different target analytes. Accordingly, if the target analyte for T1 is present in a sample, the target analyte (which is attached to a conjugate antibody, analyte, and/or antigen labeled with GOx and/or silver nitrate) immobilizes at the T1 line.

The example bioelectrochemical cells 111*a-d* of FIG. 2A are pieces of paper that have been impregnated with a redox-species (e.g., (i) potassium ferricyanide and (ii) (a) glucose or (b) ascorbic acid) and dried. In some examples, the bioelectrochemical cells 111*a-d* initially not attached to the porous media 109 and the housing includes a mechanical device to automatically and/or manually press the bioelectrochemical cell into contact with the porous media 109 for testing. In other examples, the bioelectrochemical cells 111*a-d* are initially attached to the porous media 109. Although the bottom halves of the bioelectrochemical cells 111*a-d* are coupled to the wireless chip 114 via a single pin, the bottom halves of the bioelectrochemical cells 111*a-d* may be coupled to the wireless chip 114 via four separate pins.

The example inlet 113 of FIG. 2A allows water or a buffer solution to resuspend dried reagents of the bioelectrochemical cells for testing. Accordingly, before, during, and/or after a sample has added to the sample pad 106, a user applies the water and/or buffer solution to the sample pad 106 and/or a separate sample pad and the water and/or buffer solution flows through the inlet and resuspends the dried reagents of the bioelectrochemical cells 111*a-d*. In this manner, the middle section of the bioelectrochemical cells 111*a-d* acts as a salt-bridge against diffusion induced homogenization of concentration gradient. This allows the GOx (if immobilized on the test or control line) to oxidize the glucose of the corresponding bioelectrochemical cell 111*a-d*. Alternatively, this may allow the silver nitrate to oxidize the ascorbic acid of the corresponding bioelectrochemical cell 111*a-d* to allow the reducing agent (e.g., the ascorbic acid) to reduce silver nitrate by releasing ($H_3O^+$). If one half-cell of one or more of the bioelectrochemical cells 111*a-d* is oxidized within a redox-cycle of GOx, an electron can be transferred to reduce $[Fe(CN)_6]^{3-}$ to $[Fe(CN)_6]^{4-}$ at one-half of the bioelectrochemical cell. The ferricyanide molecule acts as an electron mediator and can finally diffuse to the electrode. The concentration difference of the upper and bottom cell creates a cell voltage described by the Nernst equation $$E = 0.059\ \mathrm{V} + \log\frac{[H_3O^+][Fe(CN)_6]^{3-}}{[H_3O^+][Fe(CN)_6]^{4-}}.$$

In some examples, the flow of the electrons, the current, the voltage, an electromotoric force, and/or a corresponding resistance can be measured by the example wireless chip 114.

The example antenna 115 of FIG. 2A is structured around the other components of the example machine readable LFA device 104. The connections between the bioelectrochemical cells 111*a-d*, and/or the wireless chip 114, the antenna 115 may be via wires or etches.

Figure 2B:
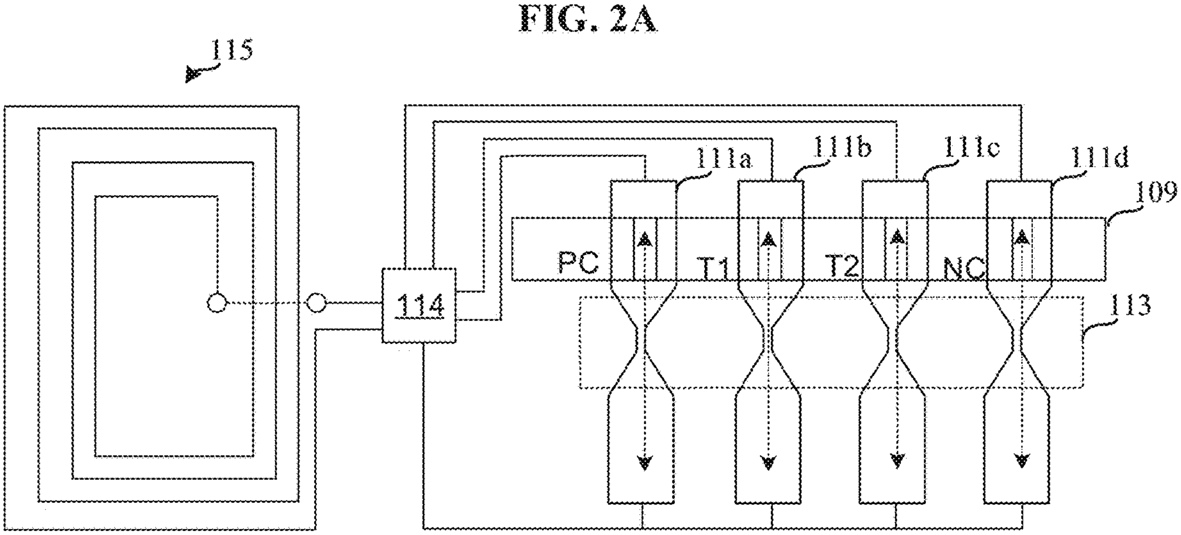
FIG. 2B illustrates an alternative example implementation of part of the machine readable lateral flow immunoassay of FIG. 1A.

FIG. 2B illustrates an alternative implementation of the example antenna 115 of FIG. 2A in the LFA device 104 of FIG. 1A. In the example of FIG. 2B, the antenna is structured in a dedicated space (as opposed to around the components of the machine readable LFA device 104). Additionally or alternatively, the example antenna 115 may be structured in a different configuration.

Figure 2C:
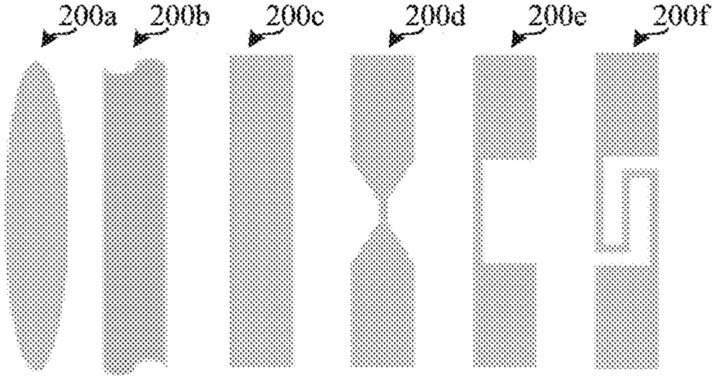
FIG. 2C illustrates example designs for any one of the potentiometric and/or bioelectrochemical cells of FIGS. 1A, 1B, 2A, and/or 2B.
Figure 2D:
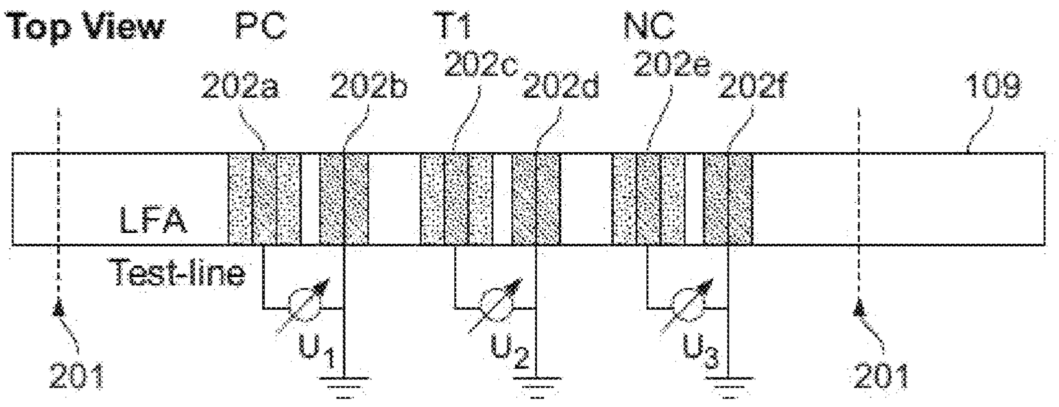
FIG. 2D illustrates a top view of an alternative example implementation of the machine readable lateral flow immunoassay of FIG. 1A.

FIG. 2C illustrates example implementations 200*a*-200*f* of one or more of the bioelectrochemical cells 111*a-n* of FIGS. 1A, 1B, 2A, and/or 2B in the LFA device 104 of FIG. 1A. Although FIG. 2C illustrates 6 different implementations 200*a*-200*f*, there may be other implementations of the bioelectrochemical cells 111*a-n*. One or more of the bioelectrochemical cells 111*a-n* may be implemented as a combination of or a topological variation of one or more of the example implementations 200*a*-200*f* For example, the implementations 200*f* may include any number of meanders between a first part and a second part of the implementations 200*f* Alternatively, the porous membrane 109 may act as the bioelectrochemical cell, as further described below in conjunction with FIG. 2D FIG. 2D illustrates an alternative example implementation of a top view of the porous media 109 of the machine readable lateral flow immunoassay 104 of FIG. 1A to generate an electrical signal corresponding to a test analyze by an enzymatic reaction. As illustrated in FIG. 2D, the porous media 109 includes a positive control zone (PC), a test zone (T1), and a negative control zone (NC). Additionally or alternatively, the porous media 109 may include any number and/or type of control zones and/or test zones. The example porous media 109 of FIG. 2D includes example membrane compressions or cuts 201, example electrodes 202*a*-202*f* corresponding to the different zones. Although the example electrodes 202*a-f* of FIG. 2D have different widths, the example electrodes 202*a-f* can be the same width and/or be structured to be any width. The width of the electrodes 202*a-f* may be based on the geometry of the porous membrane 109, the size of the salt bridge in between the working electrode (e.g., electrode 202*a*) and reference electrode (e.g., electrode 202*b*), overlap with specific test zone and out reference areas, etc. In some examples, the electrodes 202*a*, 202*c*, 202*e* are wider than the electrodes 102*b*, 102*d*, 102*f* (e.g., reference electrodes) and the electrodes 202*a*, 202*c*, 202*e* are wider than the test-bands in order to allow most flexible positioning tolerance for assembly and during manufacturing/printing of test-bands. Spacing between working-electrode to counter-electrode pairs [electrode 202*a*, reference electrode 202*b*], [electrode 202*c*, reference electrode 202*d*], [electrode 202*e*, reference electrode 202*f*] are as small as possible, (e.g., 10 nanometers (nm) to 5 millimeters (mm), but could be as small as 1 nm). The example electrodes 202*a*-202*f* may be silver carbon electrodes, copper electrodes, graphite carbon electrodes, titanium electrodes, brass electrodes, platinum and palladium electrodes, screen printed carbon electrodes doped with ferrocyanide or any other oxidizable material or electron donator, and/or any other type of electrode. In some examples, the electrodes 202*a*, 202*c*, 202*e* are copper electrodes and the reference electrodes are carbon electrodes. By having a pair of electrodes (e.g., a working electrode and a reference electrode) for a single test line and/or control line, a salt bridge can be created on the porous membrane 104 between the pair of electrodes with a low amount of impedance. In this manner, a voltage and/or current between the pair of electrodes can be read without using an external power source to facilitate the generation of the voltage and/or current. In some examples, the electrodes 202*a*-202*f* are not engaged with the porous media 109 until it is time to read a result. Accordingly, one or more mechanical devices may be used to keep the electrodes 202*a*-202*f* disengaged from (e.g., not in contact with) the porous media 109 until it is time to read the result. An example of one or more mechanical devices to cause the electrodes 202*a*-202*f* to engage and/or disengage with the porous media 109 is further disclosed below in conjunction with FIGS. 2N-2R.

In the example of FIG. 2D, the porous media 109 itself acts as the salt-bridge of a biofuel cell. A biofuel cell uses an additional enzyme (e.g., reductase, such as laccase) at a counter electrode (e.g., cathode). In such an example, the laccase reduces Oxygen ($O_2$) with $4e^-+4H^+$ to 2 $H_2O$ from reaction at the anode. The bioelectrochemical (e.g., biofuel) cells 111*a-d* of FIGS. 2A and/or 2B are impregnated with glucose and a redox species and generate a voltage and/or current (e.g., after the buffer resuspends the dried agents of the biofuel cells 111*a-d*) when a target analyte reacts with the glucose of the biofuel cell in conjunction with the redox species acting as the electron mediator. In the example of FIG. 2D, the chromatography paper (e.g., impregnated paper of the above-described biofuel cells 111*a-d*) is not included, and glucose and a redox agent is included in the liquid assay buffer. In this manner, when the liquid assay buffer including the glucose and the redox agent is applied to the sample pad 106, the liquid assay buffer saturates the porous media 109. In this manner, if the target analyte is present in a sample, the corresponding conjugates/probes labelled with GOx/gold nanoparticles will become immobilized at the corresponding test zone. Because the porous media 109 is saturated with glucose and a redox agent after the liquid assay buffer is applied, the GOx will react with (e.g., oxidize) the glucose on the test zone while the redox agent acts as an electron mediator to reduce $[Fe(CN)_6]^{3-}$ to $[Fe(CN)_6]^{4-}$ at the corresponding test zone. This result corresponds to a measurable voltage drop and/or current between the test zone and non-test zones of the porous media 109, which can be measured by the example wireless chip 114 via the example electrodes 202*a-f*. Thus, the example of FIG. 2D is a bioelectrochemical cell that is integrated into the LFA.

As described above, in some examples, an enzymatic reaction can occur with a natural mediator (e.g., oxygen) for the bioelectrochemical cell 111*a-d*. In such an example, glucose oxidizing to gluconolactone and $FADH_2$ oxidizing to FAD, thereby resulting in $H_2O_2$. Additionally or alternatively, glucose can oxidize and reduce oxygen in the presence of glucose oxidase to cause $C_6H_{12}O_6$ and oxygen ($O_2$) to react and generate $C_6H_{10}O_6$ and a product (e.g., $H_2O_2$ (hydrogen peroxide)). In such examples, the electrodes may be made of a metal (e.g., copper) or a screen printed carbon electrodes doped with ferrocyanide. In this manner, the $H_2O_2$ is reduced and oxidation of the metal or ferrocyanide of the electrode occurs by release of electrons. In later case ferrocyanide $[Fe(CN)_6]^{4-}$ reacts to $[Fe(CN)_6]^{3-}$. Released electrons can be measured by a sensor (e.g., using a current and/or voltage measurement) and processed by a processor (e.g., locally at the wireless chip 114 and/or at the reader 116) to determine a test result. Copper surface is normally oxidized by air to $Cu_2O$ (Cu(I)). $Cu_2O$ is oxidized to CuO (Cu(II)) by reduction of $H_2O_2$.

As described above, the intermediate reactant product (e.g., hydrogen peroxide) is produced by the enzyme glucose oxidase on the control and/or test line in the porous membrane 109 of FIG. 2D, respectively. In some examples, the glucose from the buffer may react with glucose oxidase on the LFA (e.g., outside the control line or test line) to produce small amounts of the product (e.g., hydrogen peroxide) on test lines where glucose oxidase is not mobilized (e.g., when the target analyte is not present in the sample). However, the concentration of the product on such areas is too low to generate sufficient electrons with electrodes on target lines when the target analyte is not present in the sample. Accordingly, in such examples, the small amount of the product will not generate false positive test results. The product (e.g., hydrogen peroxide) is diluted with the surrounding acetate buffer after the product is produced. Accordingly, without stopping the flow, the product migrates towards the wicking pad 112 and is not able to react with the electrodes 202*a*-202*f* entirely or sufficiently, which may result in no current signal or a decreased current signal. Additionally, without a stop of the flow, the product (e.g., hydrogen peroxide) produced from a first test line may flow toward a second test line or control line. In this manner, the product (e.g., hydrogen peroxide) corresponding to the first test line may be detected at the second test line or the control line as opposed to being detected at the first test line, which leads to inaccurate results.

In addition, the electrochemical measurement is based on diffusion processes between the electrodes 202*a-f*. Using an intact flow, convection is an additional factor along with the diffusion that affects the current result of the biochemical reaction. Thus, after the product (e.g., hydrogen peroxide) that can react with the electrode to cause current flow is produced at the control and/or test lines of the porous media 109, the product (e.g., hydrogen peroxide) is diluted with the surrounding buffer (e.g., acetate buffer). In this manner, if the electrodes 202*a-f* come into contact with the porous media 109 after the product has flowed to the wicking pad 112, there may not be sufficient product to react with the metal in the electrodes 202*a-f* to generate an electrical signal (e.g., via releasing of electrons). Accordingly, examples disclosed herein may arrest (e.g., slow, stop, etc.) the flow (e.g., fully or partially) to prevent and/or slow the product from migrating away from a test zone and/or control zone. In some examples, a mechanical device may be used to arrest the flow by cutting (e.g., fully or partially) the example porous media 109 at the example membrane cuts 201, thereby stopping the product from flowing toward the example wicking pad 112. Additionally or alternatively, flow may be arrested by applying a substance (e.g., glue, gel, chemical, etc.) to the porous membrane 109, activating a substance on the porous membrane 109, pinching the porous membrane 109, etc. In this manner, the product (e.g., hydrogen peroxide) will remain at the corresponding test and/or control line to react with the metal of the electrodes 202*a-f*. Although the example of FIG. 2D includes two membrane cuts 201 (e.g., before the first test line/control line and after the last test line/control line), there may be membrane cuts between the different test/control lines and/or the membrane cut before the first test line/control line may be removed. An example of one or more mechanical devices to cut the porous media 109 to stop, impede, or otherwise resist flow is further described below in conjunction with FIGS. 2L-2R.

Additionally or alternatively, a mechanical device can apply compression on the porous media 109 to create barriers (e.g., along the lines shown at the membrane cuts 201) that act as a barrier to stop the flow of the product (e.g., hydrogen peroxide) from flowing toward the wicking pad 112. Additionally or alternatively, a chemical substance (e.g., a glue, a gel, an oil, etc.) may be added on or included on and/or in the porous membrane (e.g., along the lines shown at the membrane cuts 201) that acts as a barrier to stop the flow of the product toward the wicking pad 112. Additionally or alternatively, any mechanism (e.g., mechanical, electrical, chemical, etc.) may be used to arrest flow to prevent the product (e.g., hydrogen peroxide) from flowing away from the test zone and/or control zone.

Also, as disclosed herein, in alternative examples, an amperometric redox-reaction without enzymes can be used for a bioelectrochemical cell 111*a-d*. For example, an amperometric signal of the LFA device 104 can be measured without the GOx enzyme because the gold of the AuNP may act as a catalyzer. In such examples, thiosulfate may be used to improve the signal as shown above in Processes 6-8. Additionally, as shown in the above Process 8, thiosulfate, ferricyanide, and KBr or KCl react and the AuNP will catalyze reduction to the ferrocyanide to create an electronic signal.

For example, in FIG. 2D, the electrode 202*c* is in contact with the T1 test zone and the electrode 202*d* is in contact with the non-test zone (e.g., the porous media outside of the PC zone, the T1 zone, and the NC zone). In such an example, if the target analyte corresponding to T1 is present in a sample, when the sample is applied to the sample pad 106, the sample will flow into the conjugate pad 108 and bind with conjugates and/or probes labelled with GOx, gold nanoparticles, and/or other label(s) and continue to flow through the porous media 109 and into the waste pad 112. Because the target analyte is present in the sample, the target analyte attached to the conjugate/probe labelled with the GOx/gold nanoparticles will be immobilized at the test zone Ti. Accordingly, after the porous media 109 is saturated with the liquid buffer assay (e.g., a threshold time after the liquid buffer assay including the glucose and redox species is applied to the sample pad 106), the GOx/gold nanoparticles at the test zone T1 will oxidize the glucose at the test zone T1 to generate a voltage drop (illustrated as U2 in FIG. 2D) and/or current between the test zone T1 and the area next to the test zone where the electrode 202*d* is located. The example wireless chip 114 measures the voltage drop and/or current from the electrode 202*c* to the electrode 202*d* and determines that the target analyte is present when the voltage drop and/or current is above a threshold.

Figure 2E:
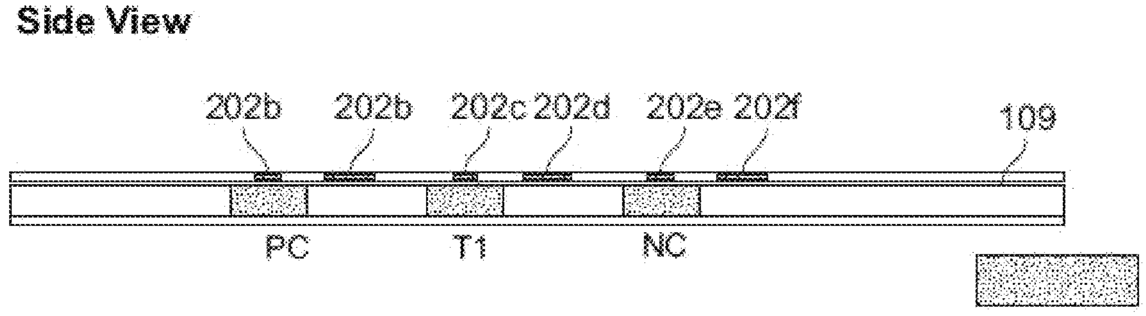
FIG. 2E illustrates a side view of the machine readable lateral flow immunoassay of FIG. 2D.
Figure 2F:
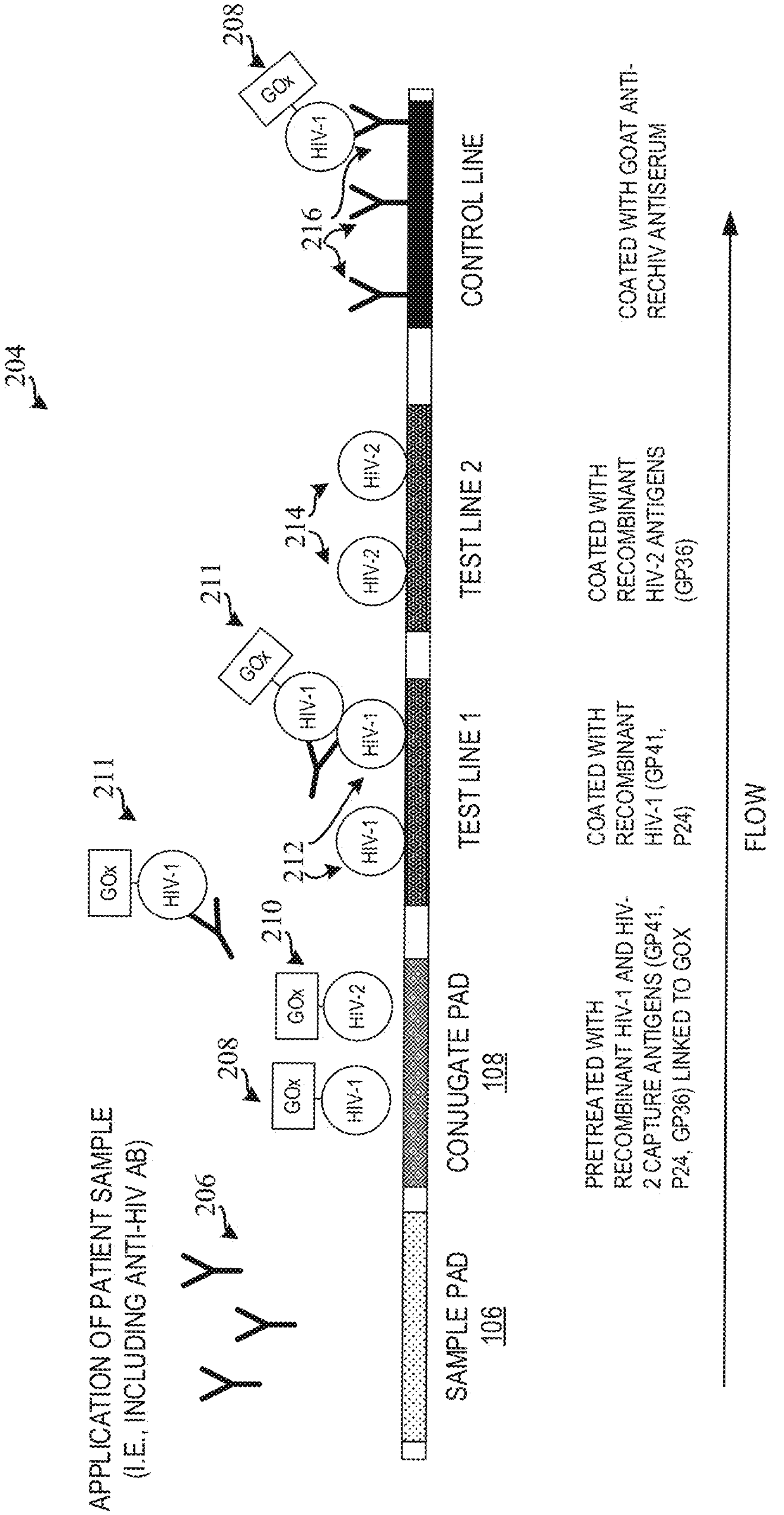
FIG. 2F illustrates example conjugates that may attach to an immobilized antigen and/or antibody on a test line of the machine readable lateral flow immunoassay of FIGS. 2D-2E.
Figure 2G:
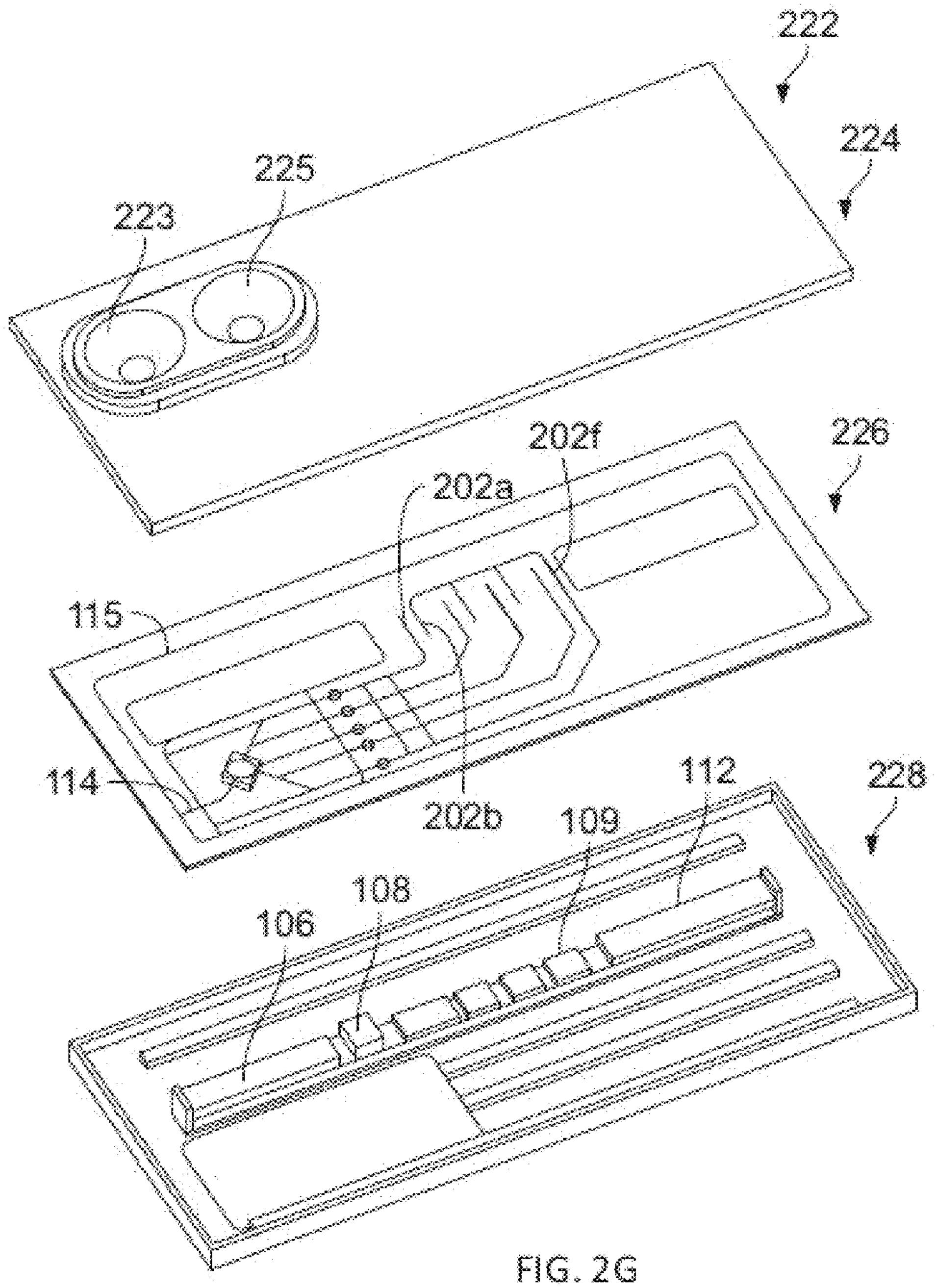
FIG. 2G illustrates an exploded view of the example lateral flow immunoassay of FIGS. 2D-2E in an example housing.

In operation, when the example of FIG. 2G is implemented in the LFA device 104 of FIG. 1A, a user or a technician applies a sample (e.g., 25 microliters of urine, blood, etc.) to the example sample pad 106. After the application of the sample, the user or a technician applies the biofuel based buffer (e.g., 6 drops of the liquid assay buffer with glucose and a redox agent) to the sample pad 106 and/or a dedicated buffer pad. Once applied, the user waits a threshold amount of time (e.g., 15 minutes) needed for the fuel cell of the porous media 109 to active. In other examples, the threshold amount of time may be 20 minutes or other values. In some examples, the threshold amount of time is tracked using a software/application-based timer or a timer that is powered by the voltage and/or current generated on the porous media 109. After the threshold duration of time, the user and/or the technician uses the reader 116 to interact with the LFA device to obtain the diagnostic test result (e.g., by generating an electromagnetic field) and within a duration of time (e.g., 1 minute) the wireless chip 114 of the LFA device 104 transmits the results to the reader 116 using the antenna 115. In some examples, the duration of time within which to read the diagnostic test result may be other value such as, for example, less than a minute or more than one or more minutes (e.g., 2 minutes, 3 minutes, or more). In some examples, the reader 116 instructs the user to take an action to arrest flow on the LFA device 114. In such examples, the reader 116 may instruct the user to take the action after within a second duration of time (e.g., 5 minutes) after the threshold amount of time (e.g., the 15 minutes). In some examples, the reader 116 may instruct the user to scan the LFA device 104 to confirm that the correct LFA device has been selected to shear prior to the second duration of time (e.g., the 5 minutes). The amount of time to that the reader 116 needs to power the wireless chip 114 to measure the electrical signal and transmit the measurement signal may be 1-3 seconds. In some examples, the reader 116 instructs the user to confirm that the action to arrest flow has been taken. Thereafter, the reader 116 starts a clock, timer, and/or countdown of the duration of time (e.g., the 1 minute) in which the diagnostic test is to be read. In some examples, the reader 116 provides a presentation on the user interface 120 indicative of the times and durations disclosed herein.

FIG. 2E illustrates a side view of the porous media 109 of the machine readable lateral flow immunoassay of FIG. 2D. In the example of FIG. 2E, the layer with the electrodes 202*a-f* in direct contact with the porous media 109. In some examples, the electrodes are incorporated in a non-conductive layer, and the non-conductive layer including the electrodes 202*a-f* is placed (e.g., during manufacturing) in contact with the porous media so that the electrodes 202*a-f* align as shown in FIG. 2D. In some examples, the electrodes 202*a-f* are each placed (e.g., during manufacturing) in contact with the porous media 109 to align as shown in FIG. 2D. In some examples, the electrodes 202*a-f* are not in contact with the porous membrane 109 until when the device is ready to be read, as further described below in conjunction with FIGS. 2L-2R.

FIG. 2F illustrates example conjugates that may attach to an immobilized antigen, analyte, and/or antibody on a test zone on the porous media 109 of the machine readable lateral flow immunoassay of FIGS. 2A-2E for an example HIV-test. FIG. 2F illustrates an example implementation 204. FIG. 2F further includes an HIV-1 target analyte 206, recombinant HIV-1 capture antigens 208, an HIV-2 capture antigen 210, an HIV-1 antibody, an HIV-1 antigen and glucose oxidase complex 211, recombinant immobilized HIV-1 antigens 212, recombinant immobilized HIV-2 antigens 214, and an antiserum 216.

During a test, a user and/or patient applies the patient biological sample and/or the buffer solution via the sample pad 106. In the example of FIG. 2F, the sample includes the example HIV-1 target analytes 206. The biological sample and/or buffer flows toward the example wicking pad 112 of FIGS. 1A and 1B. The example conjugate pad 108 is pretreated with the example recombinant HIV-1 capture antigens 208 (e.g., gp41 and p24) and the example HIV-2 capture antigens 210 (e.g., gp 36), which are linked to (e.g., attached to, tagged with, etc.) glucose oxidase. Because the biological sample includes the example target analyte 206 in FIG. 2F, the example target analyte 206 attaches to the example HIV-1 capture antigen 208 and glucose (e.g., corresponding to a formation of the example HIV-1 antibody, HIV-1 antigen and glucose oxidase complex 211), which is transported toward the wicking pad 112. The test line 1 is coated with the example recombinant immobilized HIV-1 antigens 212 (e.g., gp41 and p24), and the test line 2 is coated with the example recombinant immobilized HIV-2 antigens 214 (e.g., gp36). In case of a positive patient sample with HIV-1 antibodies 206, the antibody-antigen-glucose oxidase complex 211 binds to the immobilized recombinant HIV-1 antigen 212 on test line 1. However, because the biological sample does not include a HIV-2 target analyte, nothing binds to the test line 2. As described above, the antigen-antibody complex 211, which is linked to an enzyme (e.g., glucose oxidase) produces a product (e.g., hydrogen peroxide) on the test line 1 when the enzyme reacts with the buffer (e.g., glucose). The control line of FIG. 2F includes the example antiserum 216 (e.g., goat anti-recHIV antiserum), which binds to the example recombinant HIV-1 antigens 208.

FIG. 2G illustrates the example lateral flow immunoassay of FIGS. 2D-2E in an example housing 222. The example housing 222 houses the example sample pad 106, the example conjugate pad 108, the example porous media 109, the example waste pad 112, the example wireless chip 114, and the example antenna 115 of FIGS. 1A-2C. The example housing 222 further houses the example electrodes 202*a-f* of FIGS. 2D-2E. The example housing 222 includes example openings 223, 225 and example layers 224, 226, 228.

The top layer 224 of the example housing 222 of FIG. 2G includes the example openings 223, 225 to allow a user and/or technician to apply the sample and/or the liquid buffer. In some examples, the sample would be supplied through the opening 225, while the liquid buffer is supplied in the opening 223, which is located closer to the edge of the housing 222. This allows the buffer to wash the sample from behind as the direction of the lateral flow is from left to right in the examiner shown in FIG. 2G. Alternatively, the housing 222 may include one opening for both the sample and the liquid buffer. In some examples, the opening 223, 225 include caps to protect against evaporation (e.g., of the sample and/or the liquid buffer). Additionally or alternatively, the housing 222 may include a physical structure (e.g., a foam pad) on the underside of the top and/or or middle layer 224, 226 to apply even pressure to the porous media 109 (e.g., via user interaction with the housing 222). In this manner, the sample and/or the liquid buffer spreads evenly throughout the porous media 109. The second/middle layer 226 includes the wireless chip 114, the antenna 115 and the electrodes 202*a-f*. In some examples, the bottom of the top layer 224 includes pads to push the electrodes into contact with the porous media 109 for more complete connection between the electrodes 202*a-f* and the sections of the porous media 109.

In some examples, the middle layer 226 may further include additional electrodes for risk mitigation against reading the LFA in the bottom layer 228 too early and/or too late. For example, the example middle layer 226 may include an electrode (e.g., an anode) to be in contact with the waste pad 112 and/or an electrode (e.g., a cathode) in the waste pad to be in contact with the waste pad 112. The waste pad 122 may be impregnated ascorbic acid, which reacts with the molecules in the waste pad 122, when saturated as a test is performed, to generate a voltage, a current, and/or electromotoric force (e.g., due to different pH levels that the electrode is in contact with). In this manner, the wireless chip 114 can read the voltage and/or current differential between the electrodes in the waste pad 112 to determine if the LFA-based test is ready and/or the user has waited too long to receive an accurate result. For example, before the test is ready to be read, the anode electrode will not measure a voltage, a current, and/or electromotoric force because the dried citric acid has not been resuspended by the buffer, which indicates that the test is not ready to be read. When the test is ready to be read, the anode electrode measures a voltage, a current, and/or electromotoric force because the dried citric acid has been resuspended by the buffer, which indicates that the test is ready to be read. Additionally, when the reading of the test is too late, the resuspended citric acid diffuses to the cathode area which results in a cancelling of the electromotoric force, which indicates that the test time was overdue and that there is no longer a consistent flow throughout the device to output an accurate result. (e.g., the test can no longer be read). The bottom layer 228 of the housing 222 includes the LFA materials.

Figure 2H:
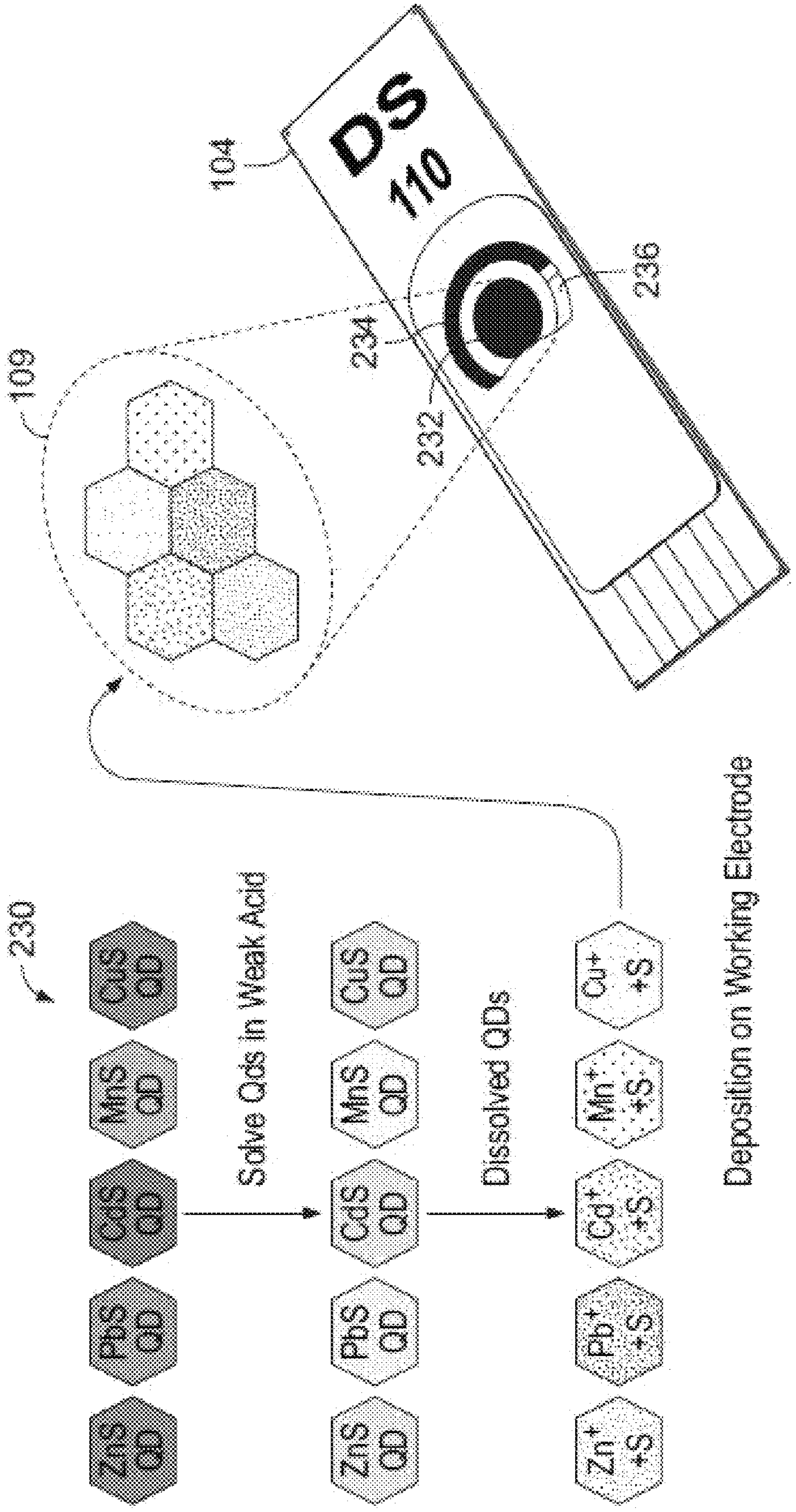
FIG. 2H illustrates an alternative example machine readable lateral flow immunoassay including quantum dots.

FIG. 2H illustrates an alternative example implementation of the machine readable lateral flow immunoassay 104 of FIG. 1A. As illustrated in FIG. 2H, the machine readable lateral flow immunoassay 104 includes the porous media 109 of FIG. 1 and example quantum dots 230 positioned on an example working electrode 232. The example lateral flow immunoassay 104 further includes an example working electrode 232, an example counter electrode 234 and an example reference electrode 236. The example electrodes 232, 234, 236 may be silver carbon electrodes, copper electrodes, graphite carbon electrodes, titanium electrodes, brass electrodes, platinum and palladium electrodes, screen printed carbon electrodes doped with ferrocyanide, and/or any other type of electrode or combinations of electrodes. The machine readable lateral flow immunoassay 104 of FIG. 2H may be used in conjunction with the bioelectrochemical cells described above.

The example quantum dots 230 of FIG. 2H operate as a conjugate on the example LFA 104. There may be different quantum dots (e.g., zinc sulfide, lead sulfide, magnesium sulfide, copper sulfide, cadmium sulfide, etc.) corresponding to a process control, a negative control, and/or one or more target analytes. During manufacturing, the example machine readable LFA generator 102 can solve the quantum dots 230 in weak acid or suitable solvent and to generate dissolved quantum dots that are added to a conjugate pad of the LFA 104. In this manner, when a sample is applied to the LFA 104, the target analyte corresponding to a particular quantum dot attaches to the quantum dot. When the quantum dots attached to the target analyte flow toward the test zone of the porous media, the quantum dots become immobilized by antigens, analytes, and/or antibodies at a test area that correspond to the one or more target analytes.

The example working electrode 232 of FIG. 2 is in contact with the porous media of the LFA 104. Accordingly, the working electrode 232 is in contact with the test area and any immobilized quantum dots (e.g., when the target analyte is present). To determine if the target analyte is present, the wireless chip 114 or another device may perform a stripping voltammetry process. To set up the stripping voltammetry process, the wireless chip 114, or other voltage supply, applies a voltage to the working electrode 232 for a particular amount of time (e.g., 60-180 seconds) to deposit (e.g., coat) the immobilized quantum dots onto the working electrode 232. After the deposition of the quantum dots to the working electrode 232, the wireless chip 114 can perform a stripping voltammetry process for a duration of time (e.g., 60-240 seconds). The stripping voltammetry includes varying the voltage potential between the counter electrode 234 and the reference electrode 236, which results in a change in current and/or voltage if the quantum dots are deposited onto the working electrode 232. The wireless chip 114 determines that the target analyte is present when a change in current and/or voltage is measured above a threshold amount.

Figure 2I:
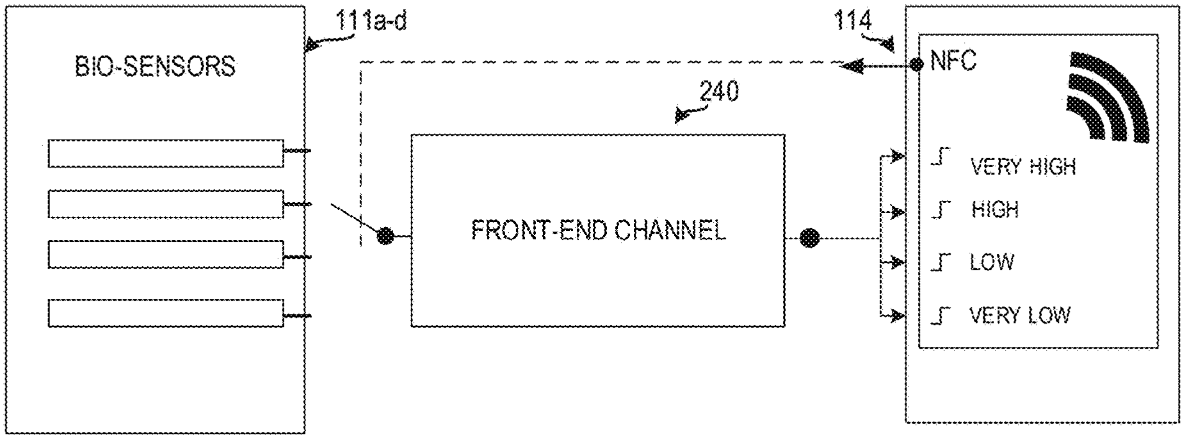
FIGS. 2I-2K illustrate different implementations of front end channels that may be used in the machine readable lateral flow immunoassay of FIGS. 1-2H.
Figure 2J:
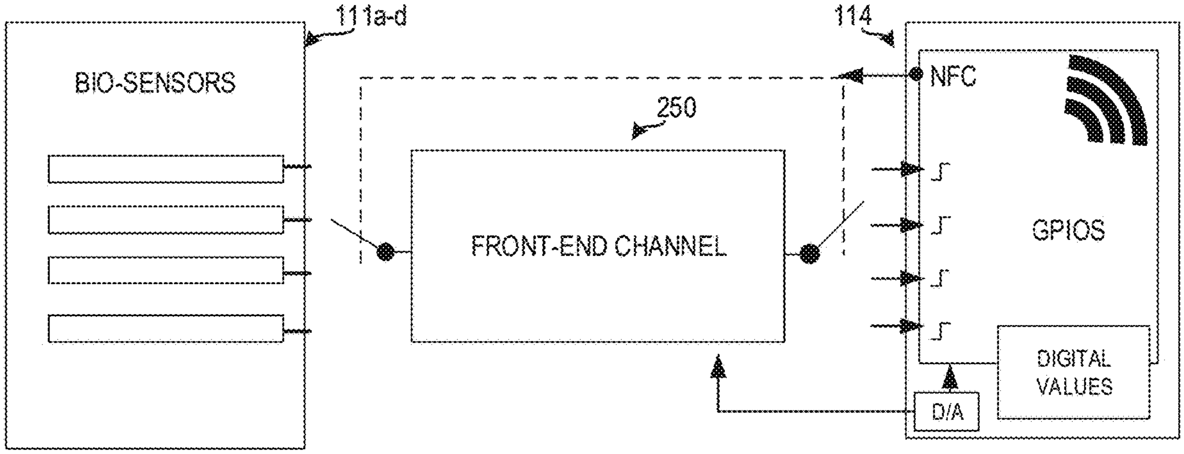
Figure 2K:
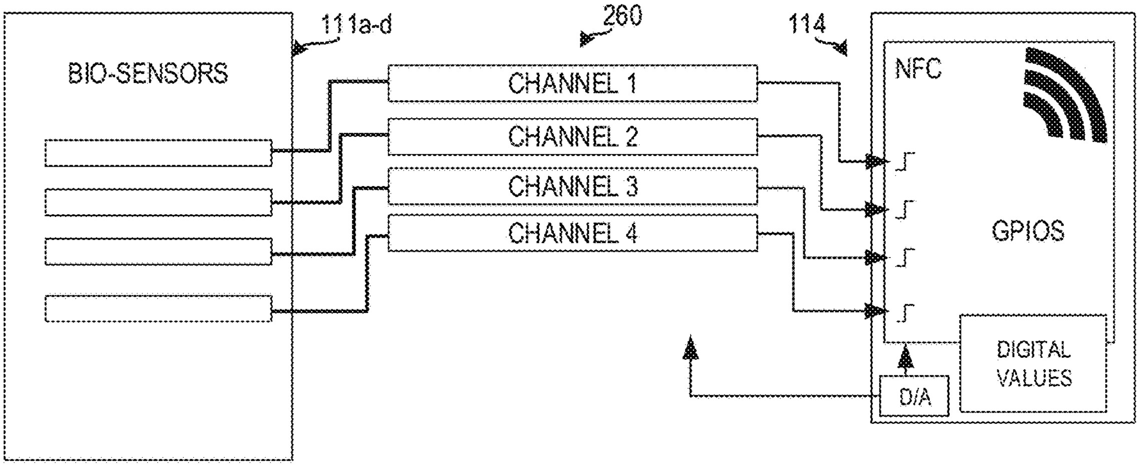

FIGS. 2I-2K illustrate example front end channels 240, 250, 260 that interface between the example bioelectrochemical cells 111*a-d* of FIGS. 1A, 1B, 2A, and/or 2B and the wireless chip 114 of FIGS. 1A, 2A, and/or 2B. Additionally or alternatively, the example front ends 240, 250, 260 may interface between the electrodes 202*a-f*, 234, 236 of FIGS. 2D, 2E, and/or 2H and the wireless chip 114. Although, the example front ends 240, 250, 260 may be implemented as a component outside of the wireless chip 114, the front ends 240, 250, 260 may be implemented in the wireless chip 114 and/or as part of another device. If the example wireless chip 114 is implemented in a standalone device (e.g., separate from the LFA 104), the example front ends 240, 250, 260 could be implemented in the LFA 104 and/or in the device that includes the wireless chip 114.

The example front end channel 240 of FIG. 21 acts as an electronic multiplexer, a group of MOSFETs and/or any other electronic circuit to transmit the signal received from each of the bioelectrochemical cells 111*a-d* to four inputs of the wireless chip 114. The example wireless chip 114 outputs a control signal to the example front end 240 to control which bioelectrochemical cell signal is to be processed at different points in time. Although the wireless chip 114 of FIG. 21 includes four inputs (e.g., very high, high, low, and very low), the wireless chip 114 can include any number of inputs corresponding to any number of levels. The four inputs of the wireless chip 114 compares the magnitude of the obtained signal to a preset threshold to identify the amount of voltage or current measured. For example, if the output of the bioelectrochemical cells 111*a-d* is a voltage (e.g., for a potentiometric sensor), the first input may compare the magnitude of the obtained voltage to 80 mV, the second input may compare the magnitude of the obtained voltage to 60 mV, the third input may compare the magnitude of the obtained voltage to 40 mV, and the fourth input may compare the magnitude of the obtained voltage to 20 mV. In this manner, if the front end 240 outputs a 70 mV signal from the first bioelectrochemical cell 111*a*, the wireless chip 114 will determine that the obtained signal is high (e.g., above 60 mV) but not very high (e.g., above 80 mV) based on the comparisons. The wireless chip 114 may transmit the determined output strength (e.g., very high, high, low, or very low) for each measurement to the example LFA reader application 117. In this manner, the results can be further analyzed to identify patterns, identify the accuracy of a test, and/or for device monitoring purposes (e.g., at the reader 116 and/or at another external device, database, server, or datacenter).

The example front end channel 250 of FIG. 2J is an alternative implementation that acts as a multiplexer and/or a demultiplexer to transmit the signal received (e.g., accessed, obtained, etc.) from each of the bioelectrochemical cells 111*a-d* to a corresponding input of the wireless chip 114. For example, the front end-channel 250 ensures that the first bioelectrochemical cells 111*a* is output to the first input, the second bioelectrochemical cells 111*b* is output to the second input, etc. For example, the front-end channel 250 may be implemented with a multiplexer and a demultiplexer, with the select lines of the multiplexer and demultiplexer coupled together to ensure that the first output of the bioelectrochemical cell 111*a* is transmitted to the first input of the wireless chip 114, the second output of the bioelectrochemical cell 111*b* is transmitted to the second input of the wireless chip 114, etc. The example wireless chip 114 outputs one or more control signals to the example front end 240 to control which bioelectrochemical cell signal is to be processed at different points in time. In some examples, the front-end channel 250 may include a multiplexer controlled to sample/measure respective ones of the electrodes at different points in time and each measurement is passed to a single comparator or analog-to-digital converter of the wireless chip 114. In this manner, all the results can be obtained using a single component on the wireless chip 114. In some examples, the front end 250 is controlled to take multiple measurements of each test line and multiple measurements of each control line. For example, the front end 250 is controlled to take multiple measurements of the test lines control lines where the wireless chip 114 transmits multiple results to the reader 116 and/or implements statistical preprocessing of the multiple measurements before sending data to the reader 116. Although the wireless chip 114 of FIG. 2J includes four inputs (e.g., for the four bioelectrochemical cells 111*a*-111*d*), the wireless chip 114 can include any number of inputs corresponding to any number of cells, controls, and/or electrodes. In the example of FIG. 2J, the inputs of the wireless chip 114 determine the amount of current and/or voltage (e.g., as digital values) corresponding to the first bioelectrochemical cell 111*a*-111*d*. The wireless chip 114 may transmit the determined output strength for each measurement to the example LFA reader application 117.

The example front end channel 260 of FIG. 2K is an alternative implementation that corresponds to direct channels between each of the bioelectrochemical cells 111*a-d* to a corresponding input of the wireless chip 114. For example, the first output of the bioelectrochemical cell 111*a* is directly coupled to the first input of the wireless chip 114 via a first channel, the second output of the bioelectrochemical cell 111*b* is directly coupled to the second input of the wireless chip 114 via a second channel, etc. Although the wireless chip 114 of FIG. 2K includes four inputs (e.g., for the four bioelectrochemical cells 111*a*-111*d*), the wireless chip 114 can include any number of inputs corresponding to any number of cells, controls, and/or electrodes. In the example of FIG. 2K, the inputs of the wireless chip 114 determine the amount of current and/or voltage (e.g., as digital values) corresponding to the first bioelectrochemical cell 111*a*-111*d*. The wireless chip 114 may transmit the determined output strength for each measurement to the example LFA reader application 117.

Although the example wireless chips 114 of FIGS. 2I, 2J, 2K include a comparator to compare the magnitude of the obtained voltage and/or current to a threshold and transmit a result corresponding to the comparison, the example wireless chips 114 may include an analog-to-digital converter to convert the analog voltage and/or current readings to a digital value and transmit the digital value to the example reader 116. In this manner, the example reader 116 can compare the digital value to one or more thresholds to determine the results. In some examples, the wireless chip 114 may obtain multiple voltage and/or current measurements (e.g., voltage samples, current samples, etc.) for each test line and control line, convert the measurements to digital values, and transmit all the digital values to the example reader 116. In some examples, the wireless chip 114 may perform preprocessing of the values (e.g., statistical analysis such as determining mean, median, mode, standard deviation, etc. of multiple measurements) and transmit one or more value(s) representative of the multiple measurements to the reader 116.

FIGS. 2L-2O illustrate examples to arrest (e.g., stop and/or slow) the flow of liquid (e.g., including generated products such as hydrogen peroxide) toward a wicking or waste pad. As described herein, the flow can be arrested to allow an amount generated product (e.g., hydrogen peroxide) to accumulate or otherwise be present at a test line to react with an electrode in contact with the test line to generate a measurable electrical signal. In some examples, the electrodes may be moved into contact with the test line to react after the flow has been arrested. In some examples, the electrodes are moved into contact with the test line as the flow arresting mechanisms are deployed or activated. FIGS. 2L-2O include portions of the LFA device 104 in a flow position (e.g., FIGS. 2L and 2N) and in a read position (e.g., FIGS. 2M and 2O). In the flow position of the LFA device 104, the chemical mixing and reactions as disclosed herein occur and the elements and/or products flow along the porous media 109 of, for example, FIG. 1A. In the read position, the electrodes 202*a-f* of FIG. 2D are applied to the porous media 109 to begin the reading phase for the diagnostic test. The example of FIGS. 2L-O includes an example switch 278, one or more example flow arrestors 280, and an example electrode board or chip 282.

Figure 2L:
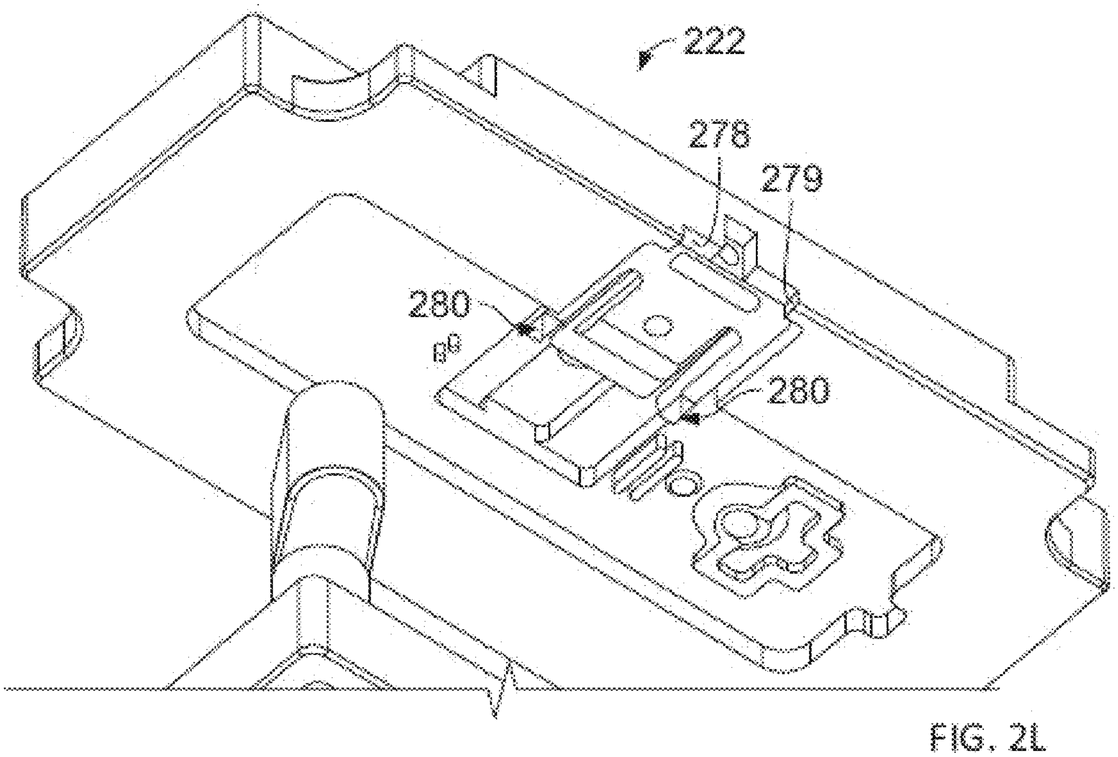
FIG. 2L illustrates a bottom view of a housing for the machine readable lateral flow immunoassay of FIGS. 1-2H including an example housing lid and an example switch in a first position.
Figure 2M:
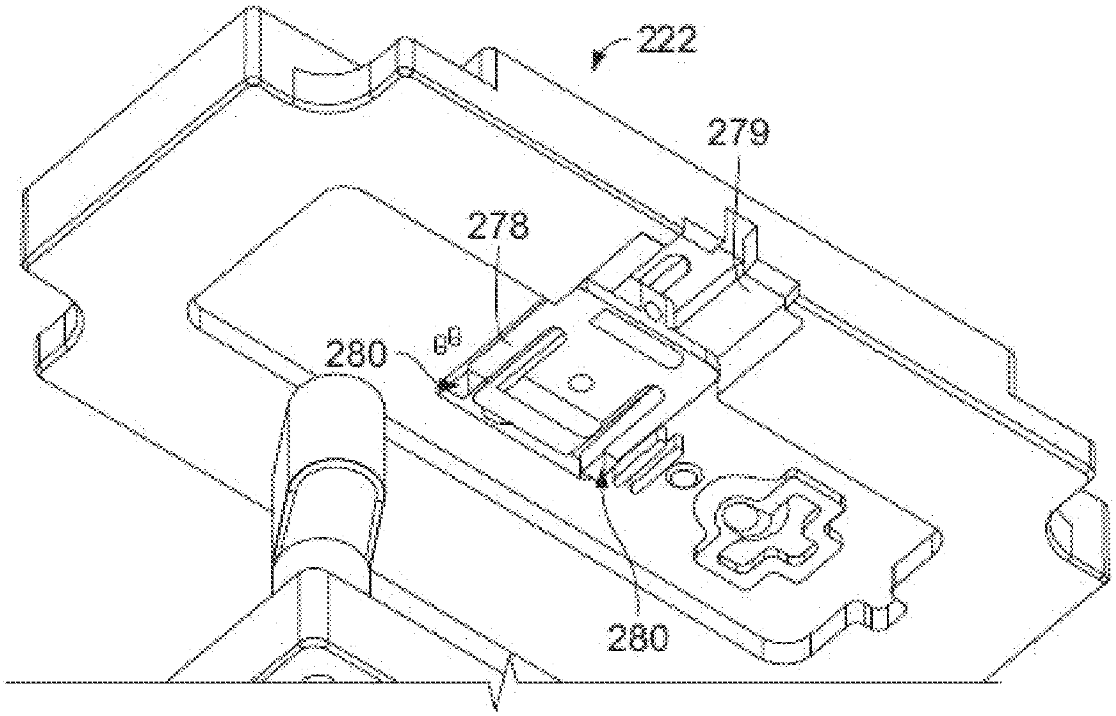
FIG. 2M illustrates a bottom view of the housing for the machine readable lateral flow immunoassay of FIG. 2L with the example switch in a second position.
Figure 2N:
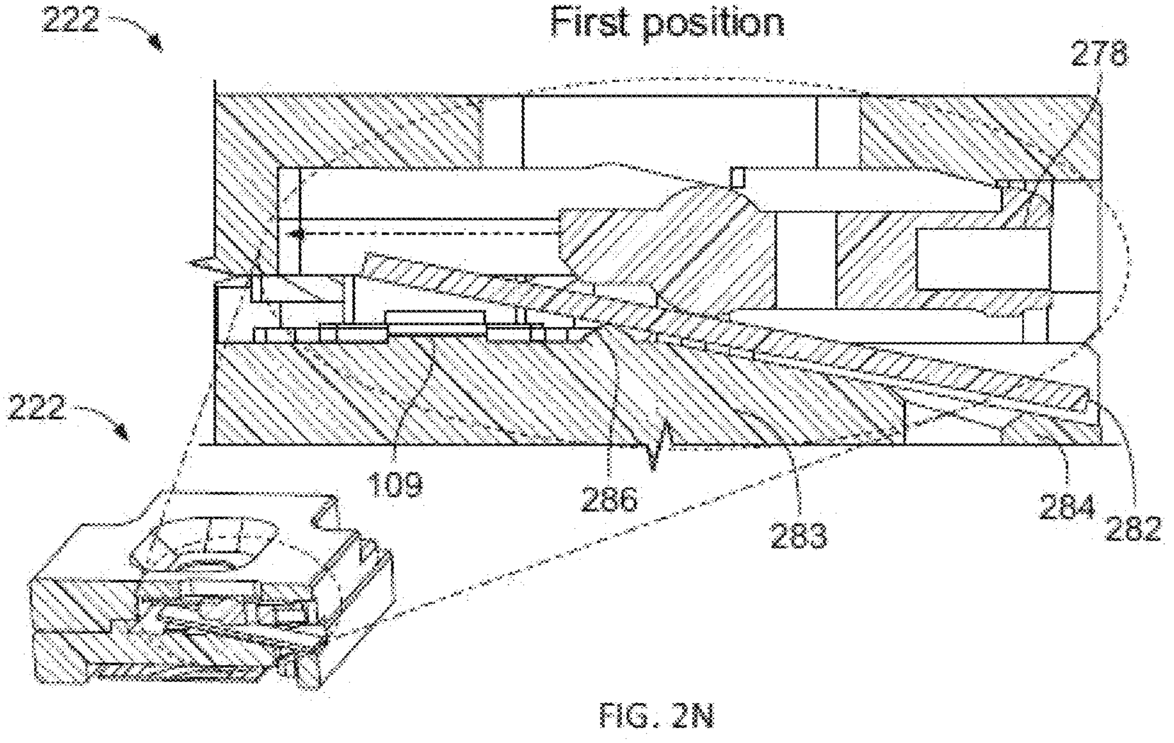
FIG. 2N illustrates a cross-sectional view the housing of the machine readable lateral flow immunoassay of FIG. 2L with the switch in the first position and an example electrodes board in a first position.
Figure 2O:
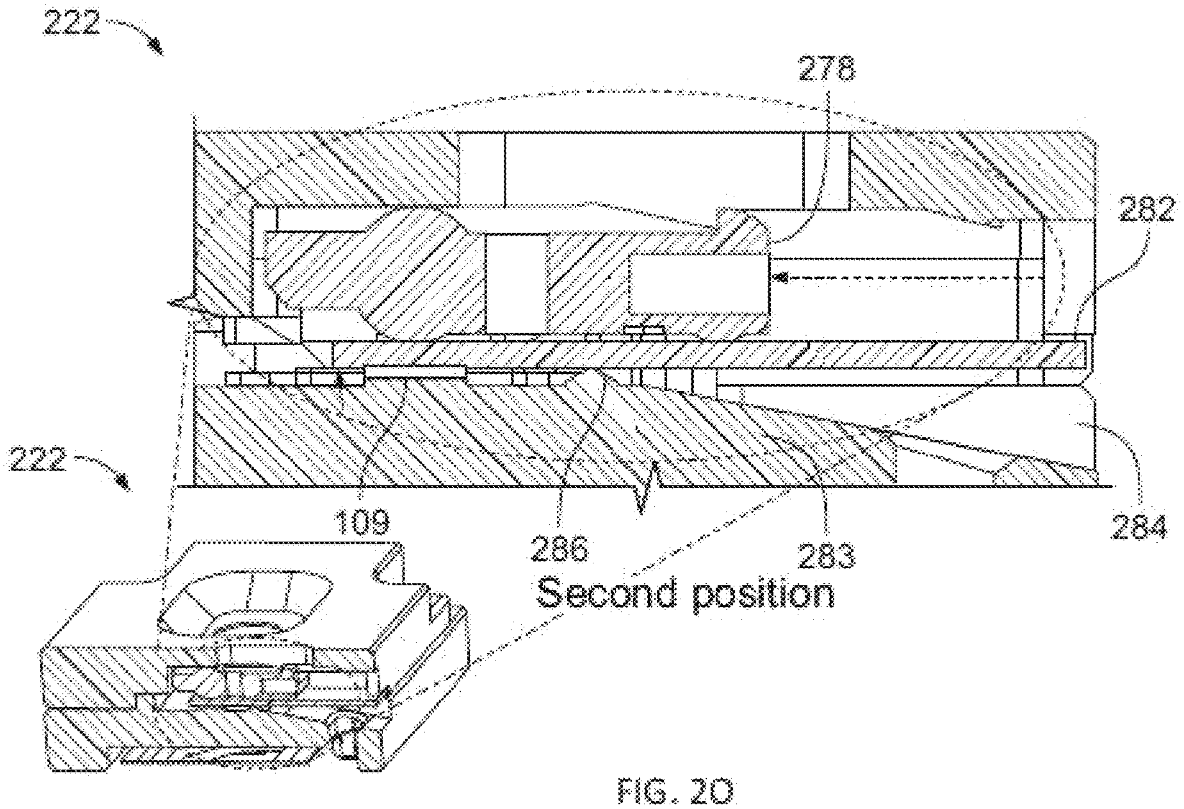
FIG. 2O illustrates a cross-sectional view of the housing of the machine readable lateral flow immunoassay of FIG. 2L with the switch in the second position and the example electrodes board of FIG. 2N in a second position.

The example switch 278 of FIGS. 2L-O is a component or device that moves between a first position (e.g., the flow position illustrated in FIGS. 2L and 2N) and a second position (e.g., the read position illustrated in FIGS. 2M and 2O). In some examples, the switch 278 slides within a groove or track 279 in the housing 222 of the LFA device 104. In some examples, the switch 278 slides, translates, or otherwise moves within the LFA device 104 between the first position and the second position. For example, the switch 278 may be depressed downward to make contact with the porous media 109.

The switch 278 includes the example positionable flow arrestors 280 that can be positioned to slice, cut, shear, and/or compress the example porous media 109 (e.g., corresponding to the example membrane cuts 201 of FIG. 2D) when the switch 278 moves from the first position to the second position. In some examples, the flow arrestors 280 include one or more blades to cut (e.g., partially or fully) the porous media 109. In some examples, to partially cut the porous media 109, the blades cut partially into the depth of the porous media. In some examples, a portion of the depth of the porous media 109 (e.g., a lower portion) is left uncut. In some examples, the flow arrestors 280 include one or more ridges to compress into the porous media 109. In some examples, the flow is arrested by the application of a chemical substance (e.g., a glue, a gel, an oil, etc.) to the porous media 109 at one or more of the locations where the flow arrestors 280 contact the porous media 109. In some examples, the chemical substance may be structured to release at a duration of time after the liquid sample or buffer has been applied (e.g., when the chemical substance is wetted by the liquid sample or buffer) that corresponds to when the flow should be arrested to prevent the product (e.g., hydrogen peroxide) from flowing away from the test and/or control zones.

In the illustrated example there are two flow arrestors 280. In some examples, there are other numbers of flow arrestors 280 such as, for example, one, three, etc. In some examples, when there is one flow arrestor, the flow arrestor is positioned to compress, cut or, shear the porous media 109 between where the electrode(s) 202*a*-202*f* contact the porous media 109 and the wicking pad 112 to isolate the wicking pad 112 and prevent the product (e.g., hydrogen peroxide) from further wicking through the porous media 109. In some examples, the second flow arrestor 280 may be used to prevent the flow of liquid back toward the conjugate pad 108.

The switch 278 is initially placed in the first position (e.g., away from the porous media 109). When a sample is applied to the LFA device 104, the sample flows across the porous media 109, as described herein. If the target analyte is present in the sample, a chemical reaction occurs that results in a product (e.g., hydrogen peroxide) being released at a target zone. A duration of time after the sample is applied, the reader 116 may instruct (e.g., order, prompt, etc.) a user to move the switch 278 from the first position to the second position (e.g., over the porous media 109), thereby causing the example flow arrestors 280 to cut, shear, and/or compress (e.g., pinch) the porous media 109 to stop or reduce the flow of the mixture including any mobilized products(e.g., hydrogen peroxide) that correspond to electron flow when present. In some examples, the switch 278 may release a substance (e.g., oil, glue, gel, etc.) along the lines corresponding to the membrane cuts 201 on the porous membrane 109 to act as a barrier to stop the flow of the product (e.g., hydrogen peroxide) that results in a current flow. In some examples, the substance may be structured to release at a duration of time after the liquid sample or buffer has been applied (e.g., when the liquid sample or buffer wets the substance) that corresponds to when the flow should be arrested to prevent the product (e.g., hydrogen peroxide) from flowing away from the test and/or control zones. The product remains in the area of the porous media 109 between the flow arrestors 280. In this manner, the product (e.g., hydrogen peroxide) can react with the metal of the electrode(s) 202*a*-202*f* that are present in this area of the porous media 109. The reaction of the product with the electrodes 202*a*-202*f* generates an electrical signal (e.g., by releasing electrons) that can be read by the example wireless chip 114 to determine that the target analyte is present in the sample. In some examples, if the electrode is in contact with the porous membrane 109 as the product (e.g., hydrogen peroxide) is being generated, the flow of electrons may be lower and/or inconsistent, which may correspond in a false negative or false positive test result. Accordingly, the electrode may be put into place (e.g., in contact with the porous membrane 109) after a duration of time to allow the product (e.g., hydrogen peroxide) to be generated. For example, because the switch 278 causes the example electrodes 202*a*-202*f* to come into contact after the glucose oxidase and the glucose have had sufficient time to react to generate the product hydrogen peroxide, the amount of product will be sufficient to react with the electrode(s) 202*a*-202*f* after flow has been stopped to generate an electrical signal strong enough to measure without the need of an external power source. In other words, an external power source is not needed to provide a potential to facilitate reading electrical signals from the reaction at the electrodes because allowing the electrodes to come into contact with the porous membrane 109 at the right time will generate a sufficiently strong signal without the need of external power. Having the electrodes in contact with the porous membrane 104 while the test glucose and glucose oxidase react causes a smaller electrical signal, which is more difficult to sense. In some examples, the switch 278 may be structured to lock into the two preset positions (e.g., the flow position and the read position). In this manner, the user is less likely to accidently move the switch 278 and/or is more likely to perform a full sheer when instructed by the reader 116. For example, the switch 278 may include a mechanism to hold the switch into the flow position and/or the read position until a threshold amount of force is applied, or until the switch 278 is adjust out of the lock position. In some examples, a clicking noise is made when the switch 278 is moved out from the flow position and/or when the switch 278 is moved into the read position to provide an audio indication to the user that the switch 278 has moved positions and/or the movement of the switch is complete.

The example electrode board 282 of FIG. 2L is a circuit board that includes the electrodes 202*a*-202*f* of FIG. 2D. In the first position of the switch 278, the electrode board 282 is placed on an angle with respect to the porous media 109 and/or the switch 278. The LFA device 1045 includes an example LFA support 283 in the housing 222. The support 283 includes an angled slot 284 to house the electrode board 282 at the angle relative to the horizontal of the porous media 109 when the LFA device is in the flow position. In this manner, the electrodes 202*a*-*f* on the example electrode board 282 are not in contact with the porous media 109. When the user moves the switch 278 to the second position, the angle of the electrode board 282 changes due to the movement of the switch component 278 and a ridge or fulcrum 286 of the LFA support 283. For example, the movement of the switch 278 pushes the electrode board 282 and rotates the electrode board 282 about the fulcrum 286 toward the porous media 109 until the electrode board 282 is in contact with the porous media 109 (e.g., in the second position or the read position). In the second position, the electrode board 282 is parallel to and/or in contact with the porous media 109 and/or the switch 278. In this manner, the electrodes 202*a*-202*f* are present in the area of the porous media 109 between the flow arrestors 280 and can react with a product that can react with the electrodes to generate electrons, and the wireless chip 114 can measure the current and/or voltage difference corresponding to the electrons to determine if a target analyte is present in the sample. If the electrode board 282 is not in contact with the porous membrane 109 while the reader 116 attempts to read a result, there will be no indication from the electrodes corresponding to the control zones or lines. Accordingly, if the user fails to move the switch 278 to the read position, the electrodes 202*a*-202*f* will not be in contact with the porous membrane 109 and if the reader 116 attempts to read the result an error will be output to the user. In some examples, the electrode board 282 is pivotable. In such examples, the user can move and/or pivot a switch which causes the example electrode board 282 to pivot into place (e.g., in contact with the porous membrane) while arresting flow on the porous membrane 282 (e.g., using the example flow arrestors 280).

In some examples, instead of or in addition to the example flow arrestors 280 implemented on the example switch 278, one or more of the flow arrestors 280 may be implemented in the electrode board 282. In this manner, when the electrode board 282 is moved toward the porous media 109, the flow arrestors 280 of the electrode board 282 can compress, cut, and/or shear the porous media 109 to stop or reduce flow of the mixture toward the wicking pad 112. In the second position, the example switch 278 holds the electrode board 282 in place to ensure that the electrodes 202*a*-202*f* remain in contact with the porous media 109. In some examples, the ridge or fulcrum 286 helps secure the electrode board 282 in a first or second position.

In some examples, the electrode board 282 is incorporated with the switch 278. For example, a face of the switch 278 that opposes the porous media 109 in the second or read position may include the electrode board 282 such that the electrodes 202*a*-202*f* are pressed into and/or otherwise contact the porous media 109 when the switch 278 is moved into the second position. In some examples the electrode board 282 may be positioned on the switch laterally offset from the flow arrestors 280 so the flow arrestors 280 contact the porous media 109 to arrest flow before the electrode board 282 makes contact with the porous media 109. In other examples, the electrode board 282 and flow arrestors 280 are aligned on the switch 278.

Although the example switch 278 compresses, cuts, and/or shears the porous media 109 and the electrode board 282 in contact with the porous media 109 in response to a slide motion from a user, the example switch 278 may be structured to compress, cut, and/or shear the porous media 109 and/or move the electrode board 282 in contact with the porous media 109 in other manners including, for example, automatically, via a push motion, and/or any other user and/or processor control.

Figure 2P:
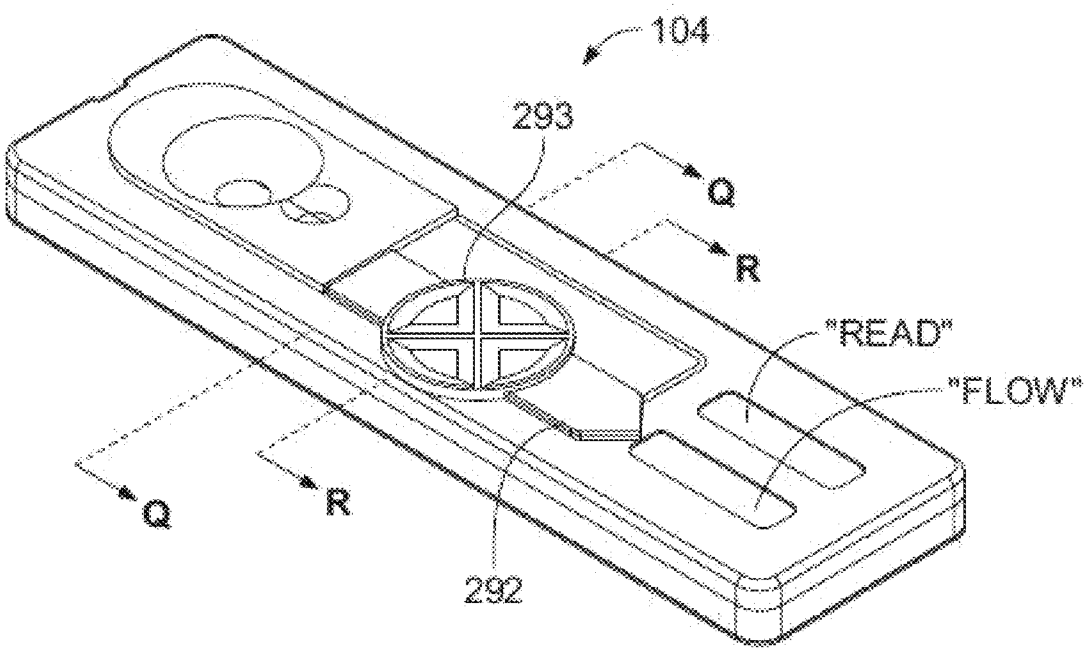
FIG. 2P illustrates a perspective view of a housing of the machine readable lateral flow immunoassay of FIGS. 1-2H with an alternative example switch.
Figure 2Q:
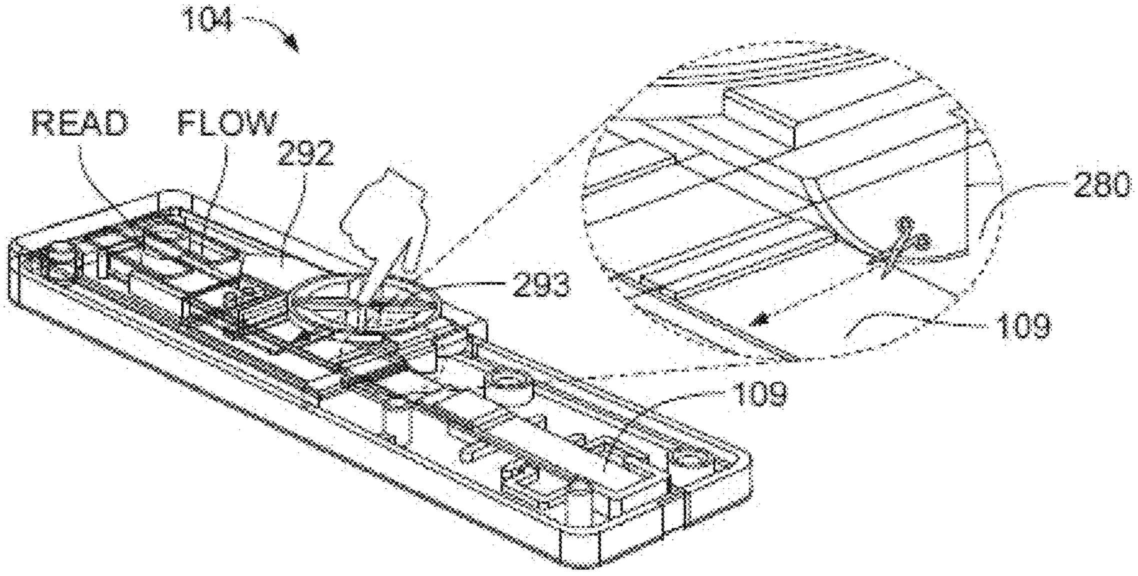
FIG. 2Q is a partial cross-sectional view taken along the Q-Q line of FIG. 2P, illustrating an interior view of the housing of the machine readable lateral flow immunoassay of FIG. 2P with the example switch in a first position.
Figure 2R:
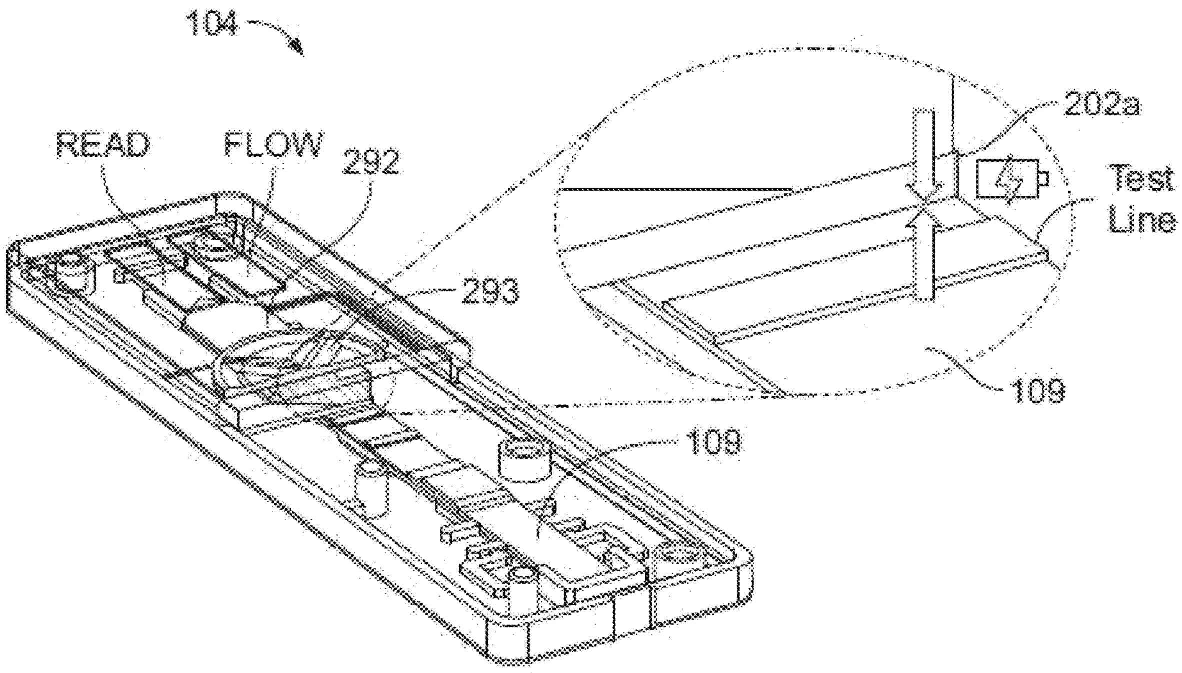
FIG. 2R is a partial cross-sectional view taken along the R-R line of FIG. 2P, illustrating an interior view of the housing of the machine readable lateral flow immunoassay of FIG. 2P with the example switch in a second position.

FIG. 2P illustrates a perspective view of the LFA device 104 with an alternative example switch 292. FIG. 2Q is a partial cross-sectional view of the LFA device taken along the Q-Q line of FIG. 2P. In FIG. 2Q, the LFA device 104 has been rotated 180 degrees compared FIG. 2P, one portion of the top plate is shown in phantom lines and the other portion removed at the Q-Q line, which shows the interior of the LFA device 104. FIG. 2R is a partial cross-sectional view of the LFA device taken along the R-R line of FIG. 2P. The LFA device 104 is orientated in FIG. 2R similar to FIG. 2Q. The switch 292 includes an example grip or actuator 293. The actuator 293 enables a user to move the switch 292 between the first position (e.g., flow position) and the second position (e.g., read position). The example switch 292 also includes the flow arrestors 280 as disclosed above. In the illustrated example, the flow arrestors 280 are coupled to or positioned on the opposite side of the switch 292 than the actuator 293.

FIG. 2Q shows the example switch 292 in the first position (e.g., the flow position), with the flow arrestors 280 positioned away from the porous media 109. In this position, the example electrode 202*a* is not in contact with the test line of the porous media 109. When the test is ready to be read, a user pushes, translates, slides, or otherwise moves the actuator 293 which moves the switch 292 to the read position (e.g., over the porous media 109). In this position, the flow arrestors 280 compress, cut, and/or shear the porous media 109 to reduce or stop flow along the porous media 109. In this manner, any product (e.g., hydrogen peroxide) generated along the porous media 109 in the area between where the flow arrestors 280 contact the porous media 109 remains in this area and near or at the correspond test and/or control lines. Additionally, moving the switch 292 causes the electrode 202*a* to come into contact with the test line of the porous media 109. In this manner, the product (e.g., hydrogen peroxide) at the test line can react with the electrode 202*a* to cause measurable release of electrons corresponding to a positive test result. In the examples of FIGS. 2P-R, the user moves the actuator 293 with a slide motion to operate the switch 292 and the flow arrestors 280. In other examples, other actuation may be used including automatic motions, pushing, squeezing, and/or any other user and/or processor control.

In some examples, the LFA device 104 and/or housing 222 of FIG. 2G, 2L-2R may include a compartment that houses a holding device (e.g., a bag) that holds liquid (e.g., a second liquid buffer). The holding device may be located near the porous media 109. In such an example, a mechanical device (e.g., the switch 278, one or more of the flow arrestors 280, the electrode board 282, the switch 292, and/or another device) may be used to break the holding device, and/or otherwise cause the holding device to release the liquid included in the holding device. In this manner, the liquid can re-buffer the porous media 109 to change the buffer conditions to optimal and/or improved conditions for antigen couplings to provide a more reliable and/or effective electronic readout. The fluid (e.g., second liquid buffer different than the liquid buffer applied to the sample pad of the LFA) that is stored in the holding device may be a different than the liquid buffer applied after the sample is applied. For example, the second liquid buffer that is stored in the holding device includes antibodies and/or antigens that help to facilitate the glucose and glucose oxidase reaction to optimize and/or improve the electrochemical read out (e.g., the current and/or voltage output when a target analyte is present). Additionally or alternatively, the LFA reader 116 may instruct (e.g., order, prompt, etc.) the user to add the additional buffer to the LFA device to increase the reliability and/or effectiveness of the electronic readout.

FIG. 3A illustrates an alternative example machine readable LFA device 300 that may be generated by the example LFA generator 102 and/or read by the example machine readable LFA reader application 117 of the reader 116. The example LFA device 300 implements the circuit completion techniques for determining a test result based on an electrical signal. The example machine readable LFA device 300 is a circuit completion LFA including the example sample pad 106, the example conjugate pad 108, the example porous media 109, the example test area 110, the example wicking pad 112, the example wireless chip 114, and the example antenna 115 of FIG. 1A. The example machine readable LFA device 300 further includes example test/control lines 302, 304, 306, first example electrodes 308*a*, and second example electrodes 308*b*.

In the example machine readable LFA device 300 of FIG. 3A, the example conjugate pad 108 includes conjugates and/or probes (e.g., antigens and/or antibodies) labelled with gold nanoparticles. The conjugates and/or probes correspond to target analytes that correspond to one or more condition(s) or disease(s). In this manner, when the sample is applied to the sample pad 106, if the sample includes a target analyte the corresponding conjugate labelled in gold binds to the target analyte and flows toward the wicking pad 112.

The test zone(s) and/or control zone(s) 302, 304, 306 of FIG. 3A extend from one side of the porous media 109 to the other side of the porous media 109. The test zone(s) and/or control zone(s) 302, 304, 306 include immobilized antigens and/or antibodies that correspond to the one or more target analytes. In this manner, if the target analyte is present in the sample, the target analyte (bonded to the conjugate labeled with gold) binds to the corresponding test and/or control lines 302, 304. Once the sample has been applied, a user applies a wash including autocatalytic silver components (e.g., a solution including silver ion and reducing agent, such as hydroquinone, aminophenols, ascorbic acid) to the sample pad 106 or another sample pad. In some examples, the sample pad 106 (or another pad or inlet) may include the silver nitrate and the reducing agent may be located in a separate paper/membrane which can be attached to the LFA media after development (e.g., via a mechanical structure that isolates the two membranes but is capable of attaching the two membranes with user interference (e.g., the user and/or automated structure applying force to the mechanical structure to press the two membranes into contact)).

As the wash flows toward the wicking pad 112 of FIG. 3A, the silver binds to the immobilized gold thereby amplifying the size of immobilized metal at the test and/or control lines 302, 304. If the silver is amplified enough, the silver molecules attached to each immobilized gold nanoparticle come into contact, creating a short (e.g., like closing an electrical switch and acting as a resistive element, such as a resistor). In this manner, a voltage can be applied to the example electrodes 308*a* at one end of the test and/or control lines 302, 304, 306 and then if the target analyte is present, silver amplification creates a short with some resistance to the second electrodes 308*b* on the other end of the test and/or control lines 302, 304, 306, thereby allowing current to flow from the electrode 308*a* to the electrode 308*b* through the silver amplified gold nanoparticles that act like a conduction enhancer (e.g., a small resistor). The example wireless chip 114 measures the current, voltage, electromotoric force, and/or resistance to determine whether the target analyte is present (e.g., if more than a threshold current or less than a threshold resistance is sensed between the electrodes 308*a*, 308*b*). The example wireless chip 114 may test each of the lines 302, 304, 306 in series or in parallel. In example illustration of the silver amplification process is further disclosed below in conjunction with FIG. 3B.

Figure 3B:
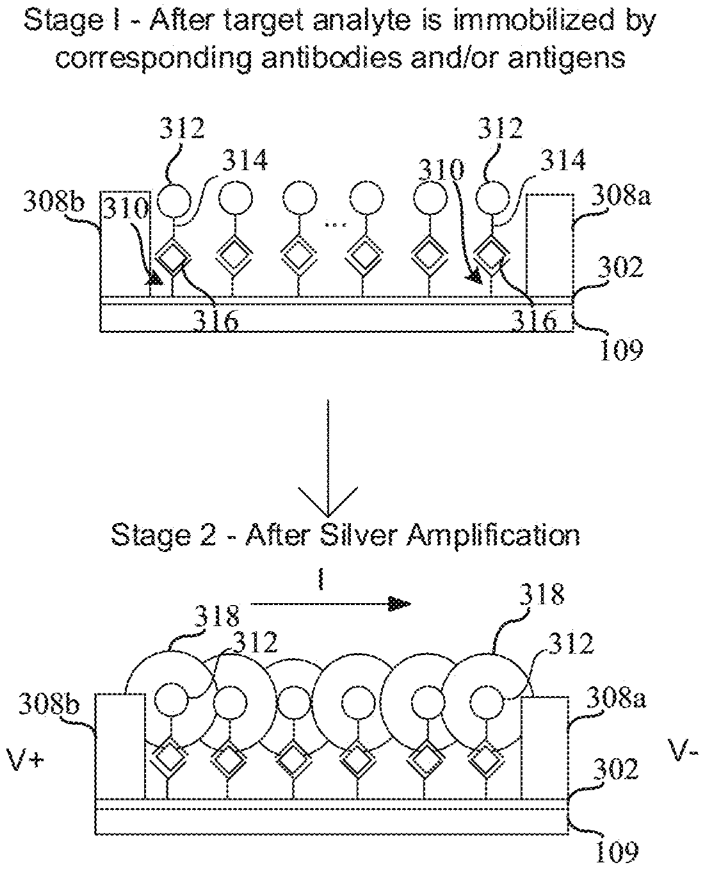
FIG. 3B illustrates an example circuit completion and silver amplification process that may occur in the example machine readable lateral flow immunoassay of FIG. 3A.

FIG. 3B illustrates an example circuit completion process of the example machine readable LFA device 300 of FIG. 3A in conjunction with a target analyte attached to the example test line 302 of FIG. 3A. The example of FIG. 3A includes the example porous media 109, the example test line 302, and the example electrodes 308*a*, 308*b* of FIG. 3A. The example of FIG. 3B further includes example immobilized antibodies/antigens 310, example gold nanoparticles 312, example conjugate antibodies/antigens 314, example target analytes 316, and example amplified silver 318. Alternatively, the example of 3B may be described in conjunction with any of the lines 302, 304, 306 of FIG. 3A.

At Stage 1, the example immobilized antibodies 310 of the example test line 302 have attached to the example target analytes 316. As shown in FIG. 3B, the target analytes 316 are attached to the example conjugate antibodies and/or antigens 314 which are labelled with the gold nanoparticles 312. However, the gold nanoparticles 312 are too small to come into contact with one another. Accordingly, if a voltage is applied to the one of the electrodes 308*a*, 308*b*, no current flows (e.g., acting as an open switch). Accordingly, a wash with silver ion solution is applied to the porous media 109. The silver in the wash amplifies (e.g., accumulates via an autocatalytic reaction) at the gold nanoparticles 312 as shown in Stage 2. When a sufficient amount of silver has amplified (e.g., through reduction of silver using a reducing agent (e.g., an autocatalytic reaction)), a short is created from the electrode 308*a* to the electrode 308*b* (e.g., acting as a closed switch with some resistance). In this manner, when the wireless chip 114 applies a positive voltage to the electrode 308*b*, current flows (e.g., via the touching silver) to the example electrode 308*a*. The example wireless chip 114 senses the current to determine that the target analyte 316 is present in the sample.

Figure 4:
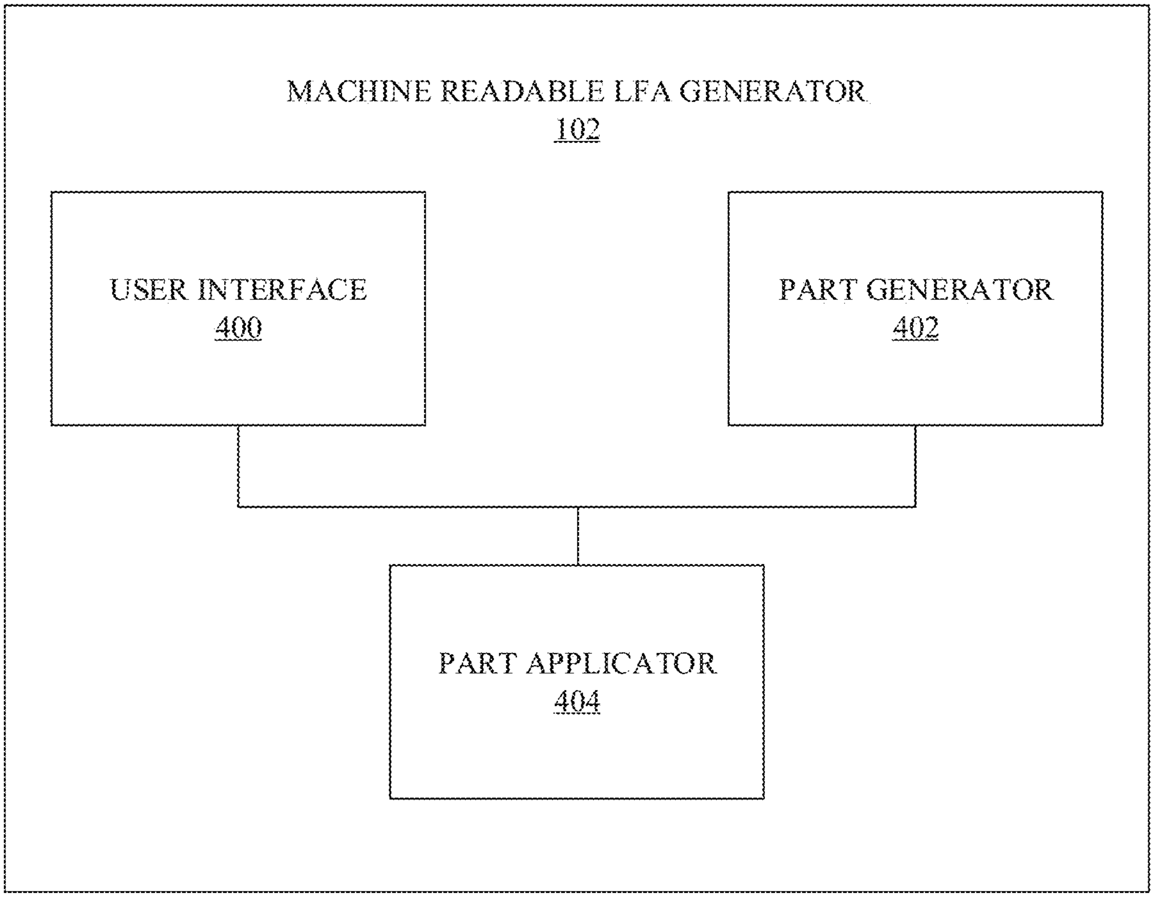
FIG. 4 is block diagram of an implementation of the machine readable lateral flow immunoassay generator of FIG. 1A.

FIG. 4 is block diagram of an example implementation of the machine readable LFA generator 102 of FIG. 1A. The example machine readable LFA generator 102 includes an example user interface 400, an example part generator 402, and an example part applicator 404.

The example user interface 400 of FIG. 4 interfaces with a user and/or manufacturer to obtain instructions regarding how to structure the machine readable LFA device 104, 300. For example, the user interface 400 may receive (e.g., access, obtain, etc.) instructions regarding which type of machine readable LFA device to generate, how many test zones (e.g., for a multiplexing LFA design) and/or test types the LFA device 104, 300 is to perform, and/or how many control zones and/or types to include in the LFA device 104, 300.

The example part generator 402 of FIG. 4 generates and/or obtains the parts of the example LFA device 104, 300. For example, the part generator 402 may generate and/or obtain samples pad 106, the conjugate pad 108, the porous media 109, the antibodies, antigens, and/or molecules to apply to the LFA device 104, 300, the wicking pad 112, the wireless chip 114, the antenna 115, the connections, the housing, and/or the bioelectrochemical cells 111*a-n* from storage. To generate a bioelectrochemical cell, the example part generator 403 may be impregnated with an enzyme substrate (e.g. glucose) and/or a reducing agent (e.g. hydroquinone, aminophenol, ascorbic acid (e.g., vitamin C), etc.), and/or an electron mediator or a redox-species (e.g. potassium ferricyanide, ferrocene, oxygen, a ferrocene derivative, etc.) to a piece of paper or other substrate and let the paper dry such as, for example, via air drying.

The example part applicator 404 of FIG. 4 applies the obtained and/or generated parts to generate the example machine readable LFA device 104, 300 of FIGS. 1A, 1B, 2A, 2B, 2D, 2E, 2H, 2L-2R, and/or 3A based on the user and/or manufacturing instructions. For example, the part applicator 404 may apply antigens and/or antibodies attached to GOx, silver nitrate, reducing agent and/or gold to the obtained and/or generated conjugate pad 108. For a gold nanoparticle amplification approach, silver nitrate may be added in a second pad with glucose (e.g., fuel and/or enzyme substrates) or a reducing agent can be impregnated in the cell paper/media. Additionally, the part applicator 404 structures the parts of the machine readable LFA device 104, 300, applies the antigens and/or antibodies corresponding to the number of tests, types of test, number of controls and/or types of controls into the test and/or control zones of the test area 110 on the porous media 109.

Figure 5:
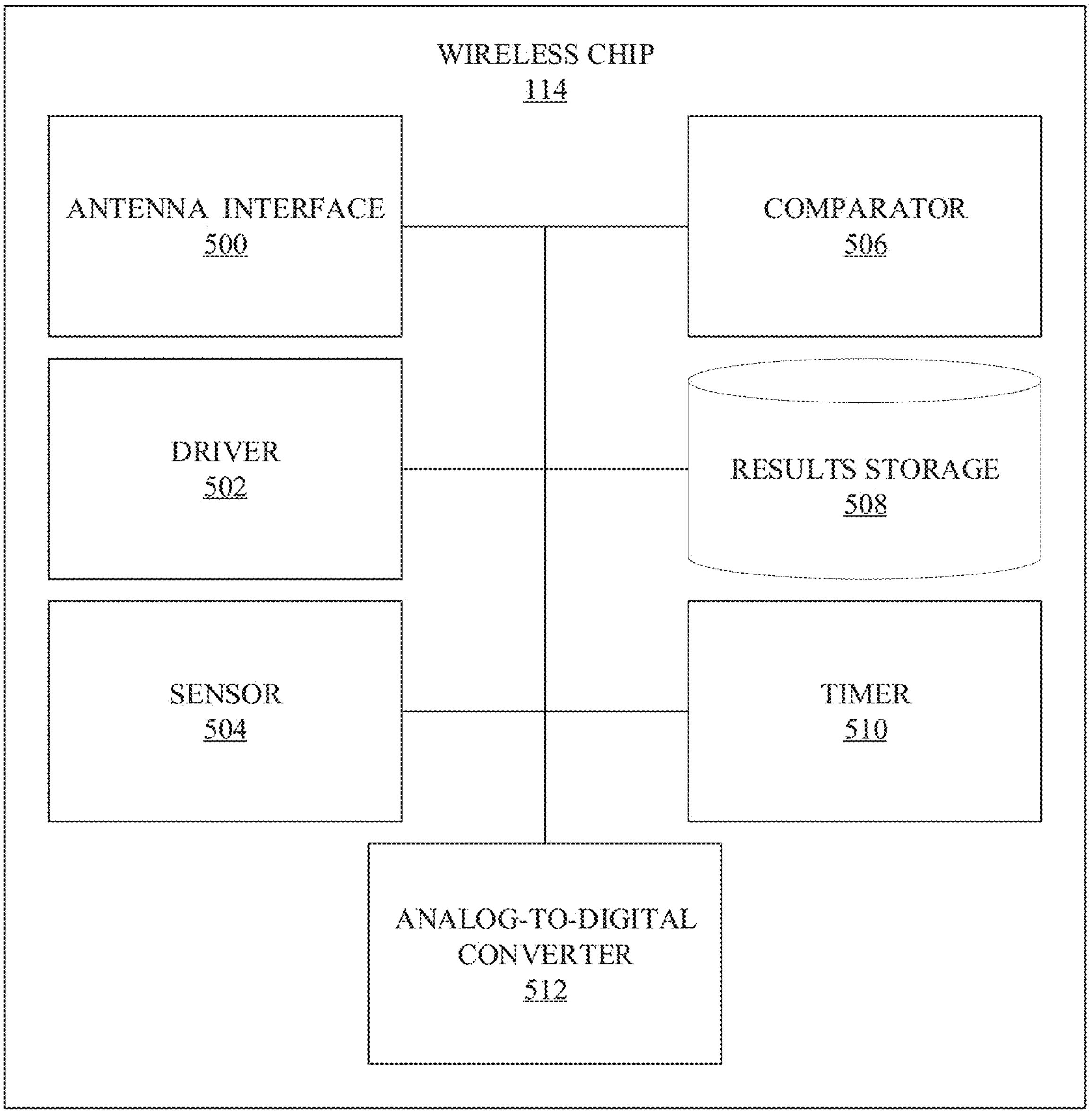
FIG. 5 is block diagram of an implementation of the wireless chip on the machine readable lateral immunoassay of FIGS. 1A, 1B, 2A, 2B, 2I-2K and/or 3A.

FIG. 5 is block diagram of an example implementation of the wireless chip 114 of FIGS. 1A, 2A, 2B, 2G, 2I-2K and/or 3A. The example wireless chip 114 includes an example antenna interface 500, an example driver 502, an example sensor 504, an example comparator 506, an example results storage 508, an example timer 510, and an example analog-to-digital converter 512.

The example antenna interface 500 of FIG. 5 interfaces with the example antenna 115. For example, when a magnetic field is within a threshold range of the antenna 115, the antenna 115 generates a current from a magnetic field that is used to power the example wireless chip 114. Thus, in some examples, the LFA device 104 does not include a storage cell (e.g., a battery that stores energy) that does not use an external supply of one or more reactants to generate a voltage. Thus, the example LFA device 104 is batteryless. For example, the LFA may be powered by an electromagnetic signal obtained at the antenna 115 (e.g., which generates a voltage based on the electromagnetic signal caused be an external device or reader) or one or more of the bioelectrochemical cell 111*a-d* (e.g., which generates a voltage based on a chemical reaction caused by the oxidation at a test zone caused by a target analyte attached to an antigen or antibody labelled with GOx and/or gold nanoparticles). In some examples, the wireless chip 114 may include a battery to power the wireless chip 114. Additionally, once the results are obtained (e.g., a flag or logic value for the one or more tests and/or controls), the antenna interface 500 might interface with the antenna 115 to transmit the results (e.g., the flags) and/or any identification information (e.g., an LFA identifier) to the example reader 116.

The example driver 502 of FIG. 5 is a voltage driver that outputs a voltage to electrodes 308*a* of FIG. 3A. As disclosed above, the wireless chip 114 outputs a voltage to determine whether the test zone has generated a short representative of a positive result for a test analyte due to circuit completion (e.g., silver amplification). Accordingly, the example driver 502 outputs the voltage to the top electrodes 308*a* (e.g., in series or in parallel) to see if the sensor 504 can measure a current and/or can measure a small resistance at the corresponding bottom electrode 308*b*, thereby corresponding to a short and a positive result. In some examples, the driver 502 controls the front-end channel 250, 260 to toggle between electrodes.

The example sensor 504 of FIG. 5 may be a voltage sensor, a current sensor, an electromotoric force sensor, or a resistance sensor. For example, for the fuel-based LFA device 104 of FIGS. 1A, 2A, 2B, 2D, 2E, 2G, 2H, and/or 2L-2R, the example sensor 504 is a voltage and/or current sensor that measures the voltage drop across and/or current between one or more of the bioelectrochemical cells 111*a-n* by sensing the voltage drop and/or current from a first pin that is coupled to a top part of the bioelectrochemical cell and a second pin that is coupled to a bottom part of the bioelectrochemical cell. In another example, for the circuit completion LFA device 300 of FIG. 3A, the example sensor 504 is a current sensor that measures the amount of current through the test lines 302, 304 and/or control zone 306 by sensing the current from a first pin coupled to the first electrode 308*a* to a second pin coupled to the corresponding second electrode 308*b*. In another example, the example sensor 504 is an electromotoric force sensor that measures an electromotoric force between the first electrode 308*a* and the second electrode 308*b* and/or measures and electromotoric force between the first pin coupled to the first part of the bioelectrochemical cell and the second pin coupled to the second part of the bioelectrochemical cell. If the example sensor 504 is a resistance sensor, the sensor 504 that measures an amount or resistance from the first pin coupled to the first electrode 308*a* to the second pin coupled to the corresponding second electrode 308*b*.

The example comparator 506 of FIG. 5 compares the sensed resistance, current, and/or voltage of each test zone and/or control zone to a threshold amount of resistance, voltage and/or current. The example comparator 506 may be a software-based comparator (e.g., to compare a digital and/or analog voltage and/or current value to a threshold), a firmware-based comparator, and/or a hardware-based comparator (e.g., input the digital and/or analog voltage and/or current to a first input, a threshold voltage and/or current to the second input and output a logic value corresponding to whether the first input is higher or lower than the second input). For example, if the sensor 504 determined the voltage drop across a first bioelectrochemical cell (e.g., the bioelectrochemical cell 111*a*), the example comparator 506 compares the voltage to a threshold (e.g., 50 mV). If the comparator 506 determines that the voltage is above the threshold, the comparator 506 outputs a first logic value (e.g., '1') and/or otherwise flags the result as a positive result for the corresponding target analyte and/or control zone. If the example comparator 506 determines that the voltage is below the threshold, the comparator 506 outputs a second logic value (e.g., '0') and/or otherwise flags the result as a negative result for the corresponding target analyte and/or control zone.

The example results storage 508 of FIG. 5 stores the results (e.g., the flags and/or logic values corresponding to the test zones and/or control zones). Additionally, the results storage 508 may store an identifier (e.g., a device identifier, identifiers of the number and/or type of tests and/or controls used in the machine readable LFA device 104, 300, etc.). In this manner, the antenna interface 500 may include the identifier with the results when transmitting the results to the reader 116.

As disclosed herein, results of the test are to be read at specific times and/or within specific time windows to permit the chemical reactions disclosed herein. Thus, in some examples, wireless chip 114 include the timer 510. The example timer 510 of FIG. 5 tracks an amount of time since one or more of the bioelectrochemical cells 111*a-n* have been activated (e.g., generating a voltage). For example, the bioelectrochemical cells 111*a-n* may apply the generated voltage of an LFA-based test to the example wireless chip 114 to power the wireless chip 114 when a test is being performed. Once powered with the voltage generated by one or more of the bioelectrochemical cells 111*a-n*, the timer 510 may initiate a wait timer to help identify when the LFA test is ready to be read. For example, the comparator 506 may compare the wait time to an assay time (e.g., a threshold corresponding to when the LFA test is ready to be read). In this manner, if the reader 116 attempts to read the LFA 104 before the LFA 104 is ready, the wireless chip 114 may transmit the timing information to the example reader 116, so that the reader 116 can determine that the test is not ready and/or determine when the test will be ready to be read.

The example analog-to-digital converter 512 of FIG. 5 converts obtained (e.g., sensed) analog voltage and/or current values from the sensor 504 into digital voltage and/or current values. In this manner, the example antenna interface 500 can transmit the digital values to the example reader 116.

Figure 6:
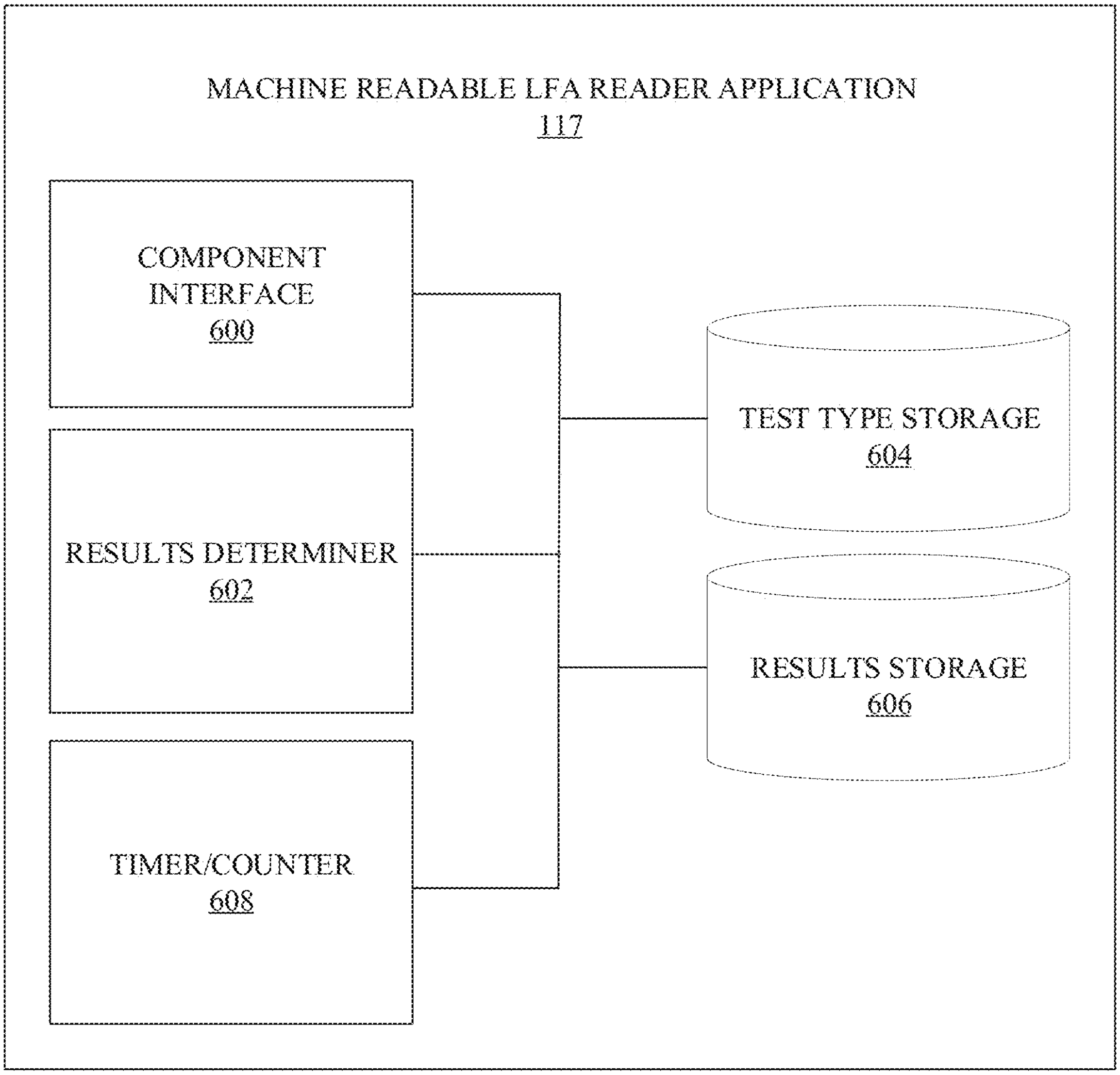
FIG. 6 is block diagram of an implementation of the machine readable lateral flow immunoassay reader application of FIG. 1A.

FIG. 6 is block diagram of an example implementation of the machine readable LFA reader application 117 of FIG. 1A to read the LFA device of FIGS. 1A, 1B, 2A, 2B, 2D, 2E, 2G, 2H, 2L-2R, and/or 3A. The example machine readable LFA reader application 117 includes an example component interface 600, an example results determiner 602, an example test type storage 604, an example results storage 606, and an example timer/counter 608.

The example component interface 600 of FIG. 6 interfaces with the other components of the example reader 116. For example, the component interface 600 may transmit prompts, text, and/or images to the example user interface 120 to display to a user. Additionally, the example component interface 600 receives (e.g., accesses, obtains, etc.) data entered by the user via the user interface 120. For example, if the user enters the identification information, patient information, demographic information, etc. into the user interface 120, the example component interface 600 obtains the entered information from the user interface 120. Additionally, the example component interface 600 interfaces with the antenna 118 to control the antenna 118 to output a magnetic field capable of wirelessly powering the example wireless chip 114 via the example antenna 115 and wirelessly receive (e.g., access, obtain, detects, etc.) data (e.g., test results, identifiers, etc.) from the example wireless chip 114. In some examples, the component interface 600 interfaces with a camera to obtain the identification information via a picture and/or scan of the LFA device 104 (e.g., a QR code, a bar code, etc.) In some examples, the component interface 600 interfaces with a transmitter (e.g., corresponding to the example antenna 118 and/or another transmission device) of the reader 116 to transmit results of an LFA-based test reading to an entity that monitors the results. For example, the component interface 600 and transmitter may send the results over a network to an external or remote location for inclusion in an ERM and/or otherwise to a medical facility, governmental agency, NGO, etc. The results may include which tests/controls are positive, which tests/controls are negative, identification information of the LFA device or the test and/or control used, and/or contextual or supplementary information obtained from the reader 116 and/or a user (e.g., timestamp, location data from a global positioning system sensor on the reader 116, patient information and/or demographics, lot number, expiration date, expiry date, test information, signal quality information, chain of custody, operator information, etc.). In this manner, if the entity that monitors the results determines that more than a threshold number of percent of a particular LFA device has been used, the LFA device can be flagged as possibly being counterfeit and subsequent actions can be taken to prevent further counterfeiting and/or reliance on test results from a counterfeit device. If a network connection is not available after a test is performed, the component interface 600 may transmit the results after receiving an indication that a network connection is available.

The example results determiner 602 of FIG. 6 determines whether the test is ready and/or the results of the test based on the obtained results and/or identification information. For example, if the identification information is not known, the example results determiner 602 obtains identification information from the wireless chip 114. Additionally or alternatively, the example results determine 602 may obtain the identification information by scanning a QR code on the LFA device 104 using a camera or instructing a user manually enter a code on the LFA device 104. The results determiner 602 can then access the number of tests, types of test, numbers of controls, and/or types of control used on the LFA device 104, 300 from the test type storage 604 (e.g., which stores identification information in conjunction with corresponding the number of tests, types of test, numbers of controls, and/or types of control used on the LFA device 104, 300) based on the identification information (e.g., a device identifier, a test and/or control structure identifier, etc.).

In some examples, the results determiner 602 authenticates an LFA device 104 based on the obtained identification information. For example, if the communication between the LFA device 104 and the wireless chip 114 is encrypted and the wireless chip 114 does not know the encryption protocol, the LFA device 104 will not be able to read the identification information. In this scenario, the results determiner 602 determines that the LFA device 104 is invalid or unauthorized.

Once the results determiner 602 determines which flags and/or binary values correspond to each test and/or control, the example results determiner 602 determines if the test is ready by comparing the result of the control to the result corresponding to a complete test. For example, if the machine readable LFA device 104, 300 has a positive control zone, then the test is ready to be read when the positive control zone corresponds to a positive test result. If the example results determiner 602 determines that the value and/or flag corresponding to the positive control zone is not positive, the results determiner 602 determines that the test is not ready to be read, and the example component interface 600 outputs an error message or other informative message to the user via the user interface 120.

If the results determiner 602 of FIG. 6 determines that the test is ready to be read, the results determiner 602 determines which tests resulted in positive and/or negative results based on the corresponding values and/or flags in the received results. The example results determiner 602 instructs the component interface 600 to display the results to a user via the example user interface 120. Additionally, the results determiner 602 may store the results in the example results storage 606. The results determiner 602 may store the results in conjunction with the received identification information and/or any contextual or supplementary information (e.g., patient information, a timestamp, demographics, location information, lot number, expiration date, expiry date, test information, signal quality information, chain of custody, operator information, etc.).

The example test type storage 604 of FIG. 6 stores information corresponding to number(s) and/or type(s) of tests and number(s) and/or type(s) of controls in conjunction with identification information (e.g., device identification, test structure identification, etc.). In this manner, when identification information of the example LFA device 104, 300 is obtained, the example results determiner 602 can identify how the results correspond to different controls and/or tests.

The example results storage 606 of FIG. 6 stores the results of an LFA test (e.g., which tests presented positive results, negative results, or indeterminate results, and/or any corresponding information) in conjunction with any identification information (e.g., a data matric code, test identifiers, etc.). In some examples, a user can enter patient information via the user interface 120. In such examples, some or all of the patient information may be added to the result information (e.g., the results storage 606 stores a record of the test result in conjunction with the patient information). Additionally or alternatively, the example component interface 600 may gather contextual information when the test is performed that may be stored in the example results storage 606 in conjunction with the results (e.g., location information, time of day information, etc.).

The example timer/counter 608 of FIG. 6 tracks one or more durations of time (e.g., time periods) to determine if a test should be tagged as invalid or potentially invalid. For example, a test may be invalid when the user performs an action after the defined durations of time. For example, after the user has verified that a sample and/or buffer has been applied, the example timer/counter 608 tracks a first duration of time corresponding to when the test will be ready to be read. Additionally, the timer/counter 608 may track a second duration of time corresponding to when the user is to rescan the LFA device 104 to verify that it is the correct LFA device to be read. Additionally, the timer/counter 608 may track a third duration of time corresponding to when the user is to stop the flow. The duration(s) of time may be based on testing algorithm that corresponds to the type of test and/or type of LFA device. In some examples, the timer/counter 608 outputs the timing windows (e.g., a clock and/or countdown corresponding to the one or more time periods) to the user via the user interface 120.

While an example manner of implementing the example machine readable LFA generator 102 of FIG. 1A is illustrated in FIG. 4, an example manner of implementing the example wireless chip 114 of FIGS. 1A, 2A, 2B, 2G, 2I-2K and/or 3A is illustrated in FIG. 5, and an example manner of implementing the example machine readable LFA reader application 117 of FIG. 1A is illustrated in FIG. 6, one or more of the elements, processes and/or devices illustrated in FIGS. 4-6 may be combined, divided, re-arranged, omitted, eliminated and/or implemented in any other way. Further, the example user interface 400, the example part generator 402, the example part applicator 404, the example antenna interface 500, the example driver 502, the example sensor 504, the example comparator 506, the example results storage 508, the example component interface 600, the example results determiner 602, the example test type storage 604, the example results storage 606, and/or, more generally, the example machine readable LFA generator 102, the example wireless chip 114, and/or the example machine readable LFA reader application 117 of FIGS. 4-6 may be implemented by hardware, software, firmware and/or any combination of hardware, software and/or firmware. Thus, for example, any of the example user interface 400, the example part generator 402, the example part applicator 404, the example antenna interface 500, the example driver 502, the example sensor 504, the example comparator 506, the example results storage 508, the example component interface 600, the example results determiner 602, the example test type storage 604, the example results storage 606, and/or, more generally, the example machine readable LFA generator 102, the example wireless chip 114, and/or the example machine readable LFA reader application 117 of FIGS. 4-6 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device (s) (FPLD(s)). When reading any of the apparatus or system claims of this patent to cover a purely software and/or firmware implementation, at least one of the example user interface 400, the example part generator 402, the example part applicator 404, the example antenna interface 500, the example driver 502, the example sensor 504, the example comparator 506, the example results storage 508, the example component interface 600, the example results determiner 602, the example test type storage 604, the example results storage 606, and/or, more generally, the example machine readable LFA generator 102, the example wireless chip 114, and/or the example machine readable LFA reader application 117 of FIGS. 4-6 is/are hereby expressly defined to include a non-transitory computer readable storage device or storage disk such as a memory, a digital versatile disk (DVD), a compact disk (CD), a Blu-ray disk, etc. including the software and/or firmware. Further still, the example machine readable LFA generator 102 of FIG. 4, the example wireless chip 114 of FIG. 5, and the example machine readable LFA reader application 117 of FIG. 6 may include one or more elements, processes and/or devices in addition to, or instead of, those illustrated in FIGS. 4-6, and/or may include more than one of any or all of the illustrated elements, processes, and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Flowcharts representative of example hardware logic, machine readable instructions, hardware implemented state machines, and/or any combination thereof for implementing the machine readable LFA generator 102, the example wireless chip 114, and/or the machine readable LFA reader application 117 of FIGS. 4-6 are shown in FIGS. 7-11B. The machine readable instructions may be one or more executable programs or portion(s) of an executable program for execution by a computer processor such as the processors 1212, 1312, 1412 shown in the example processor platforms 1200, 1300, 1410 discussed below in connection with FIGS. 12, 13 and/or 14. The programs may be embodied in software stored on a non-transitory computer readable storage medium such as a CD-ROM, a floppy disk, a hard drive, a DVD, a Blu-ray disk, or a memory associated with the processors 1212, 1312, 1412 but the entire programs and/or parts thereof could alternatively be executed by a device other than the processors 1212, 1312, 1412 and/or embodied in firmware or dedicated hardware. Further, although the example programs are described with reference to the flowcharts illustrated in FIGS. 7-11B many other methods of implementing the example machine readable LFA generator 102, the example wireless chip 114, and/or the example machine readable LFA reader application 117 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

The machine readable instructions described herein may be stored in one or more of a compressed format, an encrypted format, a fragmented format, a compiled format, an executable format, a packaged format, etc. Machine readable instructions as described herein may be stored as data (e.g., portions of instructions, code, representations of code, etc.) that may be utilized to create, manufacture, and/or produce machine executable instructions. For example, the machine readable instructions may be fragmented and stored on one or more storage devices and/or computing devices (e.g., servers). The machine readable instructions may require one or more of installation, modification, adaptation, updating, combining, supplementing, configuring, decryption, decompression, unpacking, distribution, reassignment, compilation, etc. in order to make them directly readable, interpretable, and/or executable by a computing device and/or other machine. For example, the machine readable instructions may be stored in multiple parts, which are individually compressed, encrypted, and stored on separate computing devices, wherein the parts when decrypted, decompressed, and combined form a set of executable instructions that implement a program such as that described herein.

In another example, the machine readable instructions may be stored in a state in which they may be read by a computer, but require addition of a library (e.g., a dynamic link library (DLL)), a software development kit (SDK), an application programming interface (API), etc. in order to execute the instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, the disclosed machine readable instructions and/or corresponding program(s) are intended to encompass such machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example processes of FIGS. 7-11B may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

Figure 7:
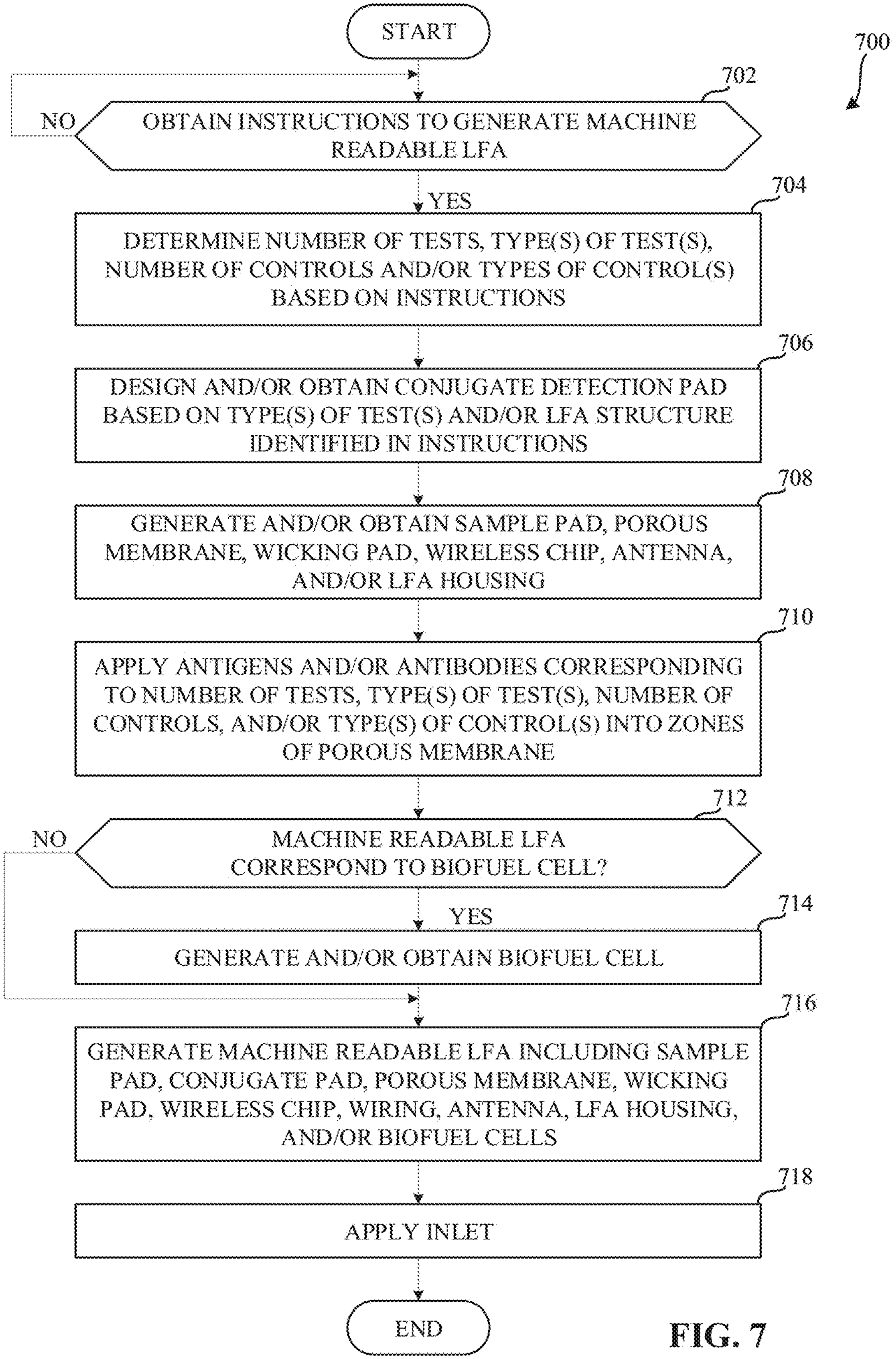
FIG. 7 illustrates a flowchart representative of machine readable instructions which may be executed to implement the machine readable lateral flow immunoassay generator of FIGS. 1A and/or 4.

FIG. 7 illustrates an example flowchart representative of machine readable instructions 700 that may be executed to implement the example machine readable LFA generator 102 of FIG. 4 to generate one of the example machine readable LFA devices 104, 300 of FIGS. 1A, 1B, 2A, 2B, 2D, 2E, 2H, 2L-2R, and/or 3A. Although the instructions 700 of FIG. 7 are described in conjunction with one of the example machine readable LFA device 104, 300 of FIGS. 1A, 1B, 2A, 2B, 2D, 2E, 2H, 2L-2R, and/or 3A, the example instructions 700 may be described and/or implemented in conjunction with any type LFA device of any structure.

At block 702, the example user interface 400 determines if instructions were obtained to generate the machine readable LFA device 104, 300. If the example user interface 400 determines that instructions have not been obtained (block 702: NO), control returns to block 702 until instructions are obtained. If the example user interface 400 determines that instructions have been obtained (block 702: YES), the example part generator 402 determines the number of tests, type(s) of test(s), number of control zones, and/or types of control zone(s) based on the user instructions (block 704). For example, the user may provide instructions to generate the LFA device 104, 300 to include three test zones corresponding to three target analytes and one positive control zone.

At block 706, the example part generator 402 designs and/or obtains a conjugate pad based on the type(s) of test(s) and/or the LFA structure identified in the instructions. For example, the part generator 402 may generate (and/or obtain from storage) a conjugate pad including antibodies and/or antigens that attach to target analytes that correspond to the type(s) of test(s) identified in the instructions. For the bioelectrochemical cell LFA device 104, the antigens and/or antibodies are attached to either GOx or gold nanoparticles (e.g., depending on how the bioelectrochemical cells 111*a*-*n* are structured). For the circuit completion LFA device 300, the antigens and/or antibodies are attached to gold nanoparticles.

At block 708, the example part generator 402 generates and/or obtains the example sample pad 106, the example porous media 109, the example wicking pad 112, the example wireless chip 114, the example antenna 115, and/or LFA housing. At block 710, the example part applicator 404 applies (e.g., immobilizes) antigens and/or antibodies corresponding to the target analytes and/or access target analytes to test zones and/or control zones in the test area 110 of the porous media 109. At block 712, the example part generator 402 determines if the instructions correspond to the LFA being the bioelectrochemical cell LFA device 104 (e.g., as opposed to the circuit completion LFA device 300). If the part generator 402 determines that the LFA does not correspond to the bioelectrochemical cell LFA device 104 (block 712: NO), control continues to block 716. If the part generator 402 determines that the LFA corresponds to the bioelectrochemical cell LFA device 104 (block 712: YES), the example part generator 402 generates and/or obtains a bioelectrochemical cell (block 714). The example part generator 402 generates the bioelectrochemical cell by impregnating a piece of paper or other substance with an enzyme substrate (e.g. glucose) and/or a reducing agent (e.g. hydroquinone, aminophenol, vitamin C, other ascorbic acids, etc.), and/or an electron mediator or a redox-species (e.g. potassium ferricyanide, ferrocene, a ferrocene derivative, etc.). Once impregnated, the example part generator 402 lets the bioelectrochemical cell dry before applying to the LFA device 104.

At block 716, the example part applicator 404 generates (e.g., assembles and/or applies) one of the machine readable LFAs 104, 300 including the sample pad 106, the example conjugate pad 108, the example porous media 109, the example wicking pad 112, the example wireless chip 114, the example antenna 115, wiring or etching (e.g., to connect the wireless chip 114 to the test zones and/or cells), the electrodes 202*a*-*f*, the switch 278, the flow arrestors 280, the electrode board 282, the actuator 293, and/or LFA housing. At block 718, the example part applicator 404 applies the example inlet 113 (e.g., by cutting away a portion of the LFA device 104, 300). In some examples, an inlet may not be included. For example, for the circuit completion LFA device 300, the silver amplification material may be applied to the example sample pad 106 to flow through the example lines 302, 304, 306.

Figure 8A:
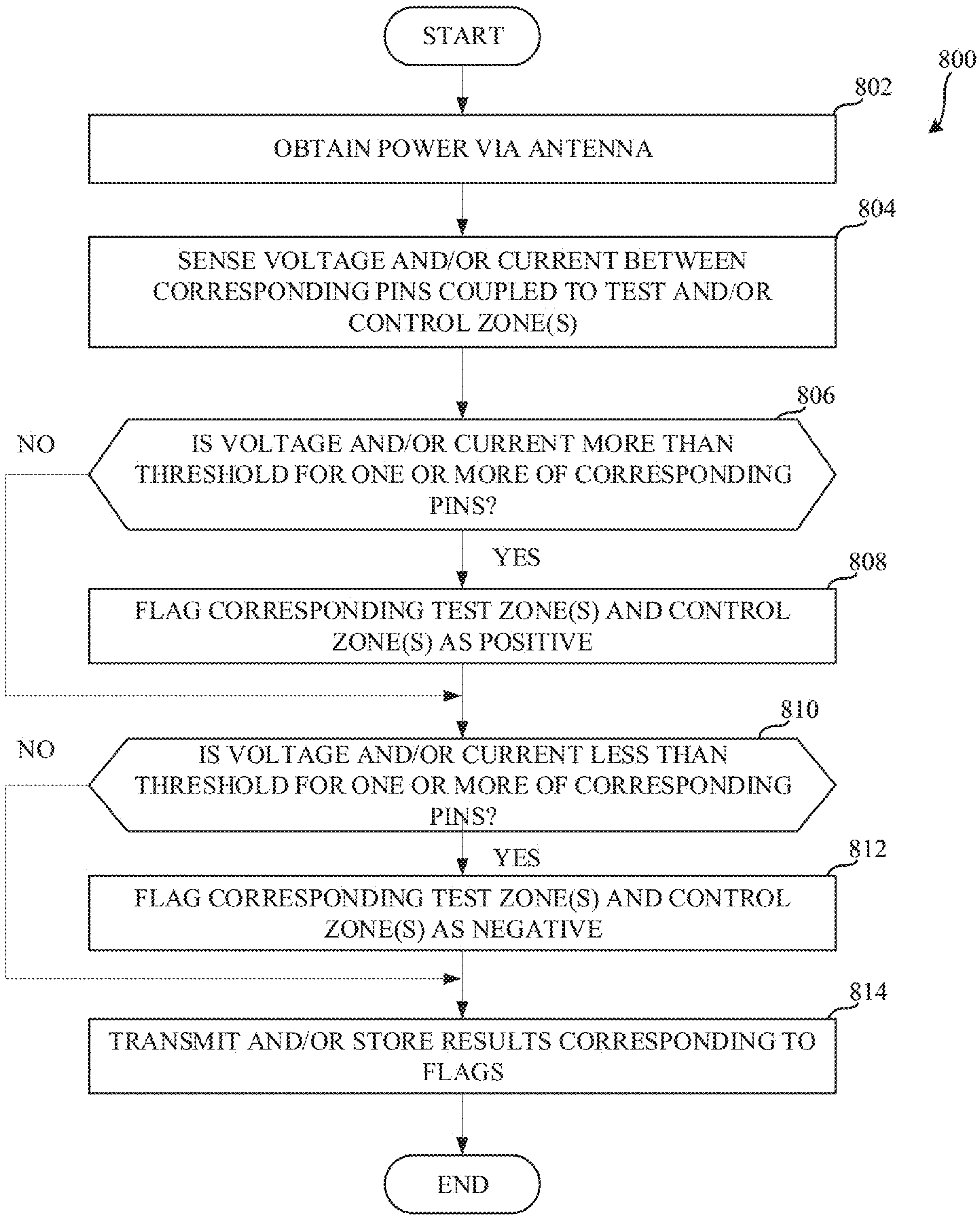
FIGS. 8A-10 illustrate flowcharts representative of machine readable instructions which may be executed to implement the wireless chip of FIGS. 1A, 2A, 2B, 2I-2K, 3A, and/or 5.

FIG. 8A illustrates an example flowchart representative of machine readable instructions 800 that may be executed to implement the example wireless chip 114 of FIG. 5 to determine the results of a test from the example bioelectrochemical cell LFA device 104 of FIGS. 1A, 1B, 2A, 2B, 2D, 2E, 2G, 2H, and/or 2L-2R. Although the instructions 800 of FIG. 8A are described in conjunction with one of the example machine readable LFA device 104 of FIGS. 1A, 1B, 2A, 2B, 2D, 2E, 2G, 2H, and/or 2L-2R. The example instructions 800 may be described and/or implemented in conjunction with any type LFA device of any structure. The example instructions 800 may be described and/or implemented in conjunction with any type LFA device of any structure including, for example, the LFA device of FIGS. 3A and 3B.

At block 802, the example antenna interface 500 obtains power via the antenna 115. For example, the example reader 116 generates a local electromagnetic field that induces a current in the example antenna 115 to power the example wireless chip 114. At block 804, the example sensor 504 senses the voltage drop and/or current flow between corresponding pins coupled to the test and/or control zones via the example electrodes 308*a*, 308*b*. The example sensor 504 may sense the voltage drop and/or current flow of each zone in series or in parallel.

At block 806, the example comparator 506 determines if the voltage drop and/or current flow is more than a threshold for one or more corresponding pins. For example, the comparator 506 may determine if the sensed voltage drop and/or current flow of each test and/or control is more than 50 mV. In some examples, the comparator 506 determines if the voltage drop and/or current flow is more than multiple different thresholds. In this manner, the comparator 506 can determine how much the sensed voltage drop and/or current flow was, as described above in conjunction with FIG. 2A-2K. If the example comparator 506 determines that the voltage drop and/or current flow is not more than a threshold for one or more corresponding pins (block 806: NO), control continues to block 810. If the example comparator 506 determines that the voltage drop and/or current flow is more than a threshold for one or more corresponding pins (block 806: YES), the example comparator 506 flags (e.g., marks or outputs a logic value) the corresponding test zone(s) and/or control zone(s) as corresponding to a positive result (block 808). The example results storage 508 stores the flag(s) in conjunction with corresponding zone(s), as further disclosed below at block 814.

At block 810, the example comparator 506 determines if the voltage drop and/or current flow is less than a threshold for one or more corresponding pins. For example, the comparator 506 may determine if the sensed voltage drop and/or current flow of each test and/or control is less than 50 mV. If the example comparator 506 determines that the voltage drop and/or current flow is not less than a threshold for one or more corresponding pins (block 810: NO), control continues to block 814. If the example comparator 506 determines that the voltage drop and/or current flow is less than a threshold for one or more corresponding pins (block 810: YES), the example comparator 506 flags (e.g., marks or outputs a logic value) the corresponding test zone(s) and/or control zone(s) as corresponding to a negative result (block 812). At block 814, the example results storage 508 stores the flag(s) in conjunction with corresponding zone(s) and/or the example antenna interface 500 transmits (e.g., via the antenna 115) the results corresponding to the flags. The antenna 115 may also transmit identification information (e.g., device identifier, test number and/or type identifiers, control number and/or type identifiers) with the results.

Figure 8B:
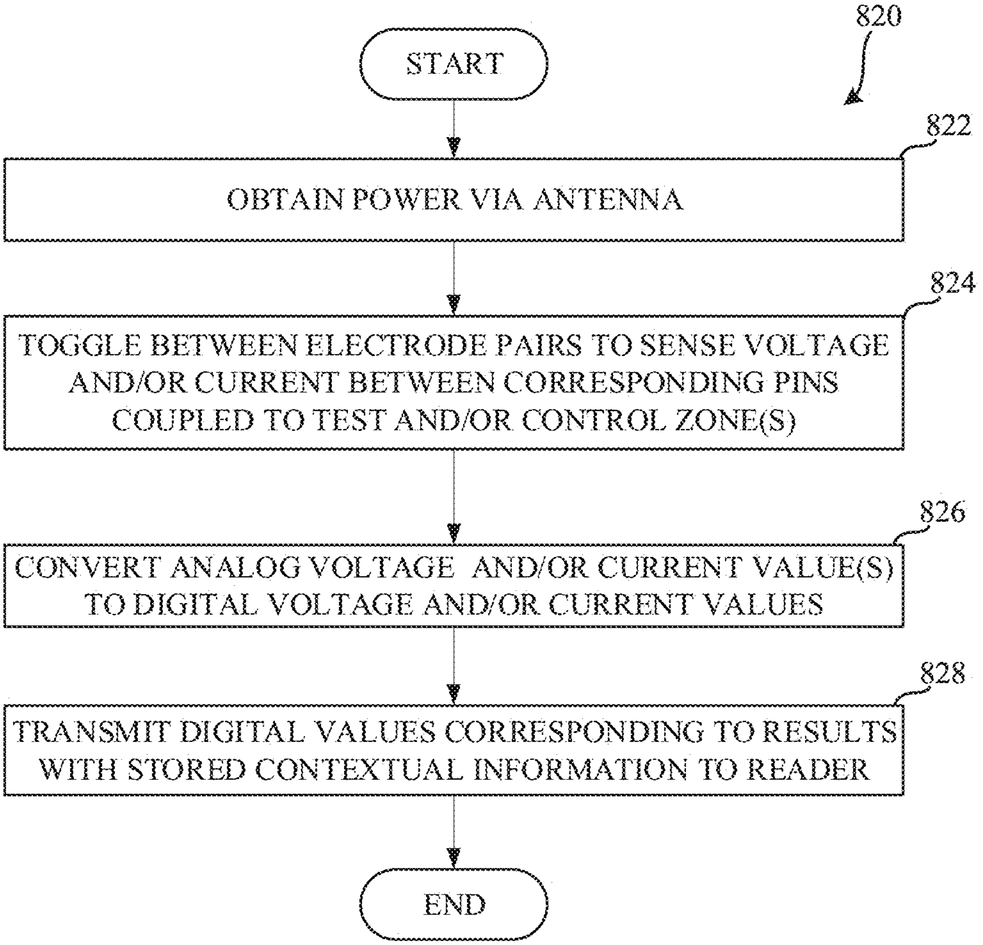

FIG. 8B illustrates an example flowchart representative of alternative machine readable instructions 820 that may be executed to implement the example wireless chip 114 of FIG. 5 to determine the results of a test from the example bioelectrochemical cell LFA device 104 of FIGS. 1A, 1B, 2A, 2B, 2D, 2E, 2G, 2H, and/or 2L-2R. Although the instructions 820 of FIG. 8B are described in conjunction with one of the example machine readable LFA device 104 of FIGS. 1A, 1B, 2A, 2B, 2D, 2E, 2G, 2H, and/or 2L-2R. The example instructions 820 may be described and/or implemented in conjunction with any type LFA device of any structure. The example instructions 800 may be described and/or implemented in conjunction with any type LFA device of any structure including, for example, the LFA device of FIGS. 3A and 3B At block 822, the example antenna interface 500 obtains power via the antenna 115. For example, the example reader 116 generates a local electromagnetic field that induces a current in the example antenna 115 to power the example wireless chip 114. At block 824, the example driver toggles between the electrode pairs so that the sensor 504 can obtain one or more voltage samples and/or current samples between corresponding pins coupled to test and/or control zones. For example, the driver 502 may toggle the select line of one of the example front ends 240, 250 to allow the sensor 504 to sense a voltage drop and/or current flow between corresponding electrodes. As described above, the driver 502 may control the front end 240, 250 to obtain multiple samples of each test line and/or control line. In some examples, the sensor 504 may obtain the voltage/current directly from the channels of the front end 260 without a toggle. Additionally or alternatively, the example LFA device 104 may obtain any data corresponding to a test result. At block 826, the example analog-to-digital converter 512 converts the analog voltage and/or current measurements to digital value(s). At block 828, the example antenna interface 500 transmits (e.g., via the antenna 115) the digital voltage values for the zones along with the corresponding information (e.g., device identifier, test type identifier, product code, etc.) to the reader 116. In some examples, block 826 may be omitted and the example antenna interface 500 may transmit the analog voltage and/or current measurements to the example reader 116. In some examples, the wireless chip 114 may compare the measurements to one or more thresholds to generate results as further described above in conjunction with FIG. 8A.

Figure 9:
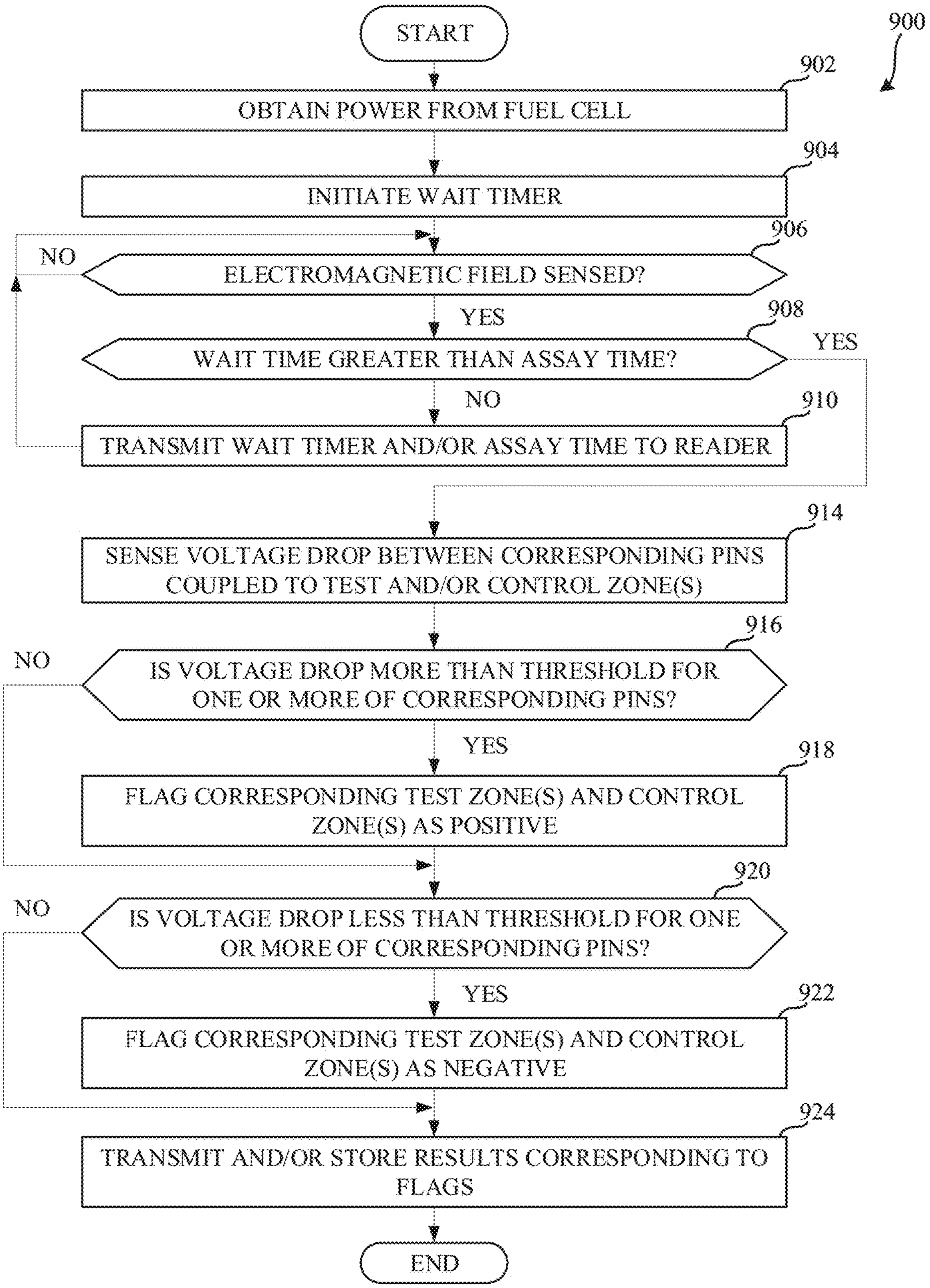

FIG. 9 illustrates an example flowchart representative of machine readable instructions 900 that may be executed to implement the example wireless chip 114 of FIG. 5 to determine the results of a test from the example bioelectrochemical cell LFA device 104 of FIGS. 1A, 1B, 2A, 2B, 2D, 2E, 2G, 2H and/or 2L-2R that is powered from the voltage generated by one of more of the bioelectrochemical cells 111*a*-111*n*. Although the instructions 900 of FIG. 9 are described in conjunction with one of the example machine readable LFA device 104 of FIGS. 1A, 1B, 2A, 2B, 2D, 2E, 2G, 2H, and/or 2L-2R, the example instructions 900 may be described and/or implemented in conjunction with any type LFA device of any structure.

At block 902, the example wireless chip 114 obtains power from one or more of the bioelectrochemical cells 111*a*-*n*. As described above, when one or more of the test zones and/or the control zones immobilizes target analytes, a voltage is generated at one or more for the bioelectrochemical cells 111*a-n*. The generated voltage can be used to power the wireless chip 114. At block 904, the example timer 510 initiates a wait timer. When the wait timer reaches a threshold amount of time (e.g., an assay time), the test is ready to be read. In this manner, if the reader 116 attempts to read the LFA 104 before the LFA 104 is ready to be read, the wireless chip 114 can transmit the wait time and/or assay time so that the reader 116 can display how much time is remaining before the LFA 104 is ready to be read.

At block 906, the example antenna interface 500 determines if an electromagnetic field is sensed via the example antenna 115. When the reader 116 attempts to read the LFA 104, the reader 116 generates an electromagnetic field to initiate communications with the wireless chip 114. If the example antenna interface 500 determines that an electromagnetic field is not sensed (block 906: NO), control returns until an electromagnetic field is sensed. If the example antenna interface 500 determines that an electromagnetic field is sensed (block 906: YES), the comparator 506 determines whether the wait time (e.g., from the example timer 510) is greater than the assay time (e.g., a threshold time corresponding to the test being ready to be read) (block 908). If the example comparator 506 determines that the wait time is not greater than the assay time (block 908: NO), the example antenna interface 500 interfaces with the antenna 115 to transmit the timing information (e.g., the current wait time and/or assay time) to the example reader 116 (block 910). In this manner, the reader 116 can determine how much more time is needed and/or display the amount of time to a user. Premature reading of the results and/or other result read errors are prevented because the process 900 includes determining whether the wait time is greater than the assay time.

If the example comparator 506 determines that the wait time is greater than the assay time (block 908: YES), the example sensor 504 senses the voltage drop between corresponding pins coupled to the test and/or control zones via the example electrodes 308*a*, 308*b* (block 914). The example sensor 504 may sense the voltage drop of each zone in series or in parallel. At block 916, the example comparator 506 determines if the voltage drop is more than a threshold for one or more corresponding pins. For example, the comparator 506 may determine if the sensed voltage drop of each test and/or control is more than 50 mV. If the example comparator 506 determines that the voltage drop is not more than a threshold for one or more corresponding pins (block 916: NO), control continues to block 920. If the example comparator 506 determines that the voltage drop is more than a threshold for one or more corresponding pins (block 916: YES), the example comparator 506 flags (e.g., marks or outputs a logic value) the corresponding test zone(s) and/or control zone(s) as corresponding to a positive result (block 918). The example results storage 508 stores the flag(s) in conjunction with corresponding zone(s), as further disclosed below at block 924.

At block 920, the example comparator 506 determines if the voltage drop is less than a threshold for one or more corresponding pins. For example, the comparator 506 may determine if the sensed voltage drop of each or respective ones of the test and/or control is less than 50 mV. If the example comparator 506 determines that the voltage drop is not less than a threshold for one or more corresponding pins (block 920: NO), control continues to block 924. If the example comparator 506 determines that the voltage drop is less than a threshold for one or more corresponding pins (block 920: YES), the example comparator 506 flags (e.g., marks or outputs a logic value) the corresponding test zone(s) and/or control zone(s) as corresponding to a negative result (block 922). At block 924, the example results storage 508 stores the flag(s) in conjunction with corresponding zone(s) and/or the example antenna interface 500 transmits (e.g., via the antenna 115) the results corresponding to the flags. The antenna 115 may also transmit identification information (e.g., device identifier, test number and/or type identifiers, control number and/or type identifiers) with the results.

Figure 10:
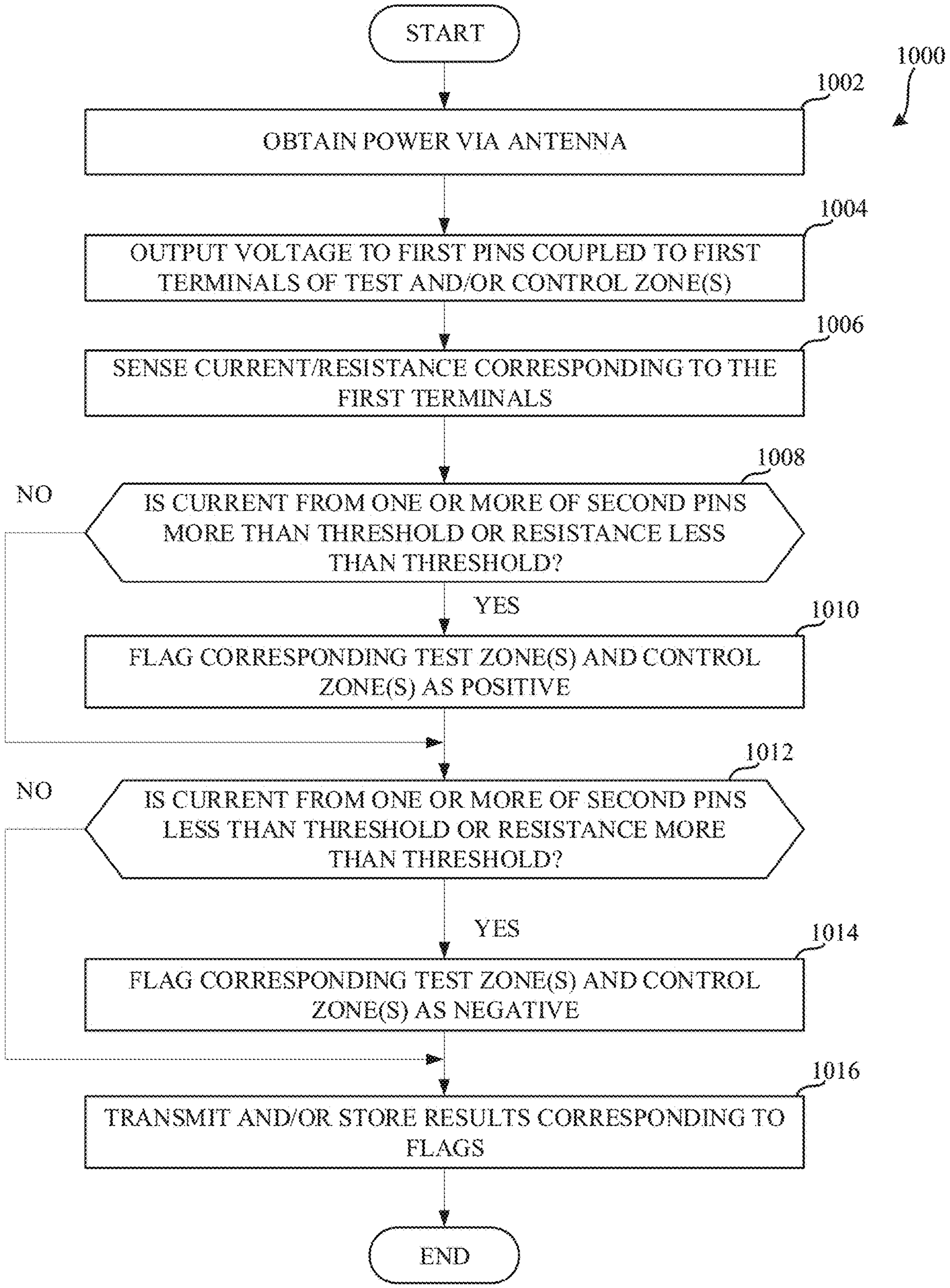

FIG. 10 illustrates an example flowchart representative of machine readable instructions 1000 that may be executed to implement the example wireless chip 114 of FIG. 5 to determine the results of a test from the example circuit completion LFA device 300 of FIG. 3A. Although the instructions 1000 of FIG. 10 are described in conjunction with the example machine readable LFA device 300 of FIG. 3A, the example instructions 1000 may be described and/or implemented in conjunction with any type LFA device of any structure.

At block 1002, the example antenna interface 500 obtains power via the antenna 115. For example, the example reader 116 generates a local electromagnetic field that induces a current in the example antenna 115 to power the example wireless chip 114. At block 1004, the example driver 502 outputs a voltage to first pins coupled to first electrodes 308*a* of the test zone(s) and/or control zone(s). The example driver 502 may output a voltage to each of the first pins in parallel or in series. At block 1006, the example sensor 504 senses the current and/or resistance from second pins coupled to the second electrodes 308*b* of the test zone(s) and/or control zone(s).

At block 1008, the example comparator 506 determines if the current is more than a threshold for one or more corresponding pins or the resistance is less than a threshold. For example, the comparator 506 may determine if the sensed current of each test and/or control is within a defined range. In some examples, the comparator 506 determines if the current/resistance is more than multiple different thresholds. In this manner, the comparator 506 can determine how much the sensed current/resistance was, as described above in conjunction with FIG. 2A-2K. If the example comparator 506 determines that the current is not more than a threshold for one or more corresponding pins of the resistance is not less than a threshold (block 1008: NO), control continues to block 1012. If the example comparator 506 determines that the current is more than a threshold for one or more corresponding pins or the resistance is less than a threshold (block 1008: YES), the example comparator 506 flags (e.g., marks or outputs a logic value) the corresponding test zone(s) and/or control zone(s) as corresponding to a positive result (block 1010). The example results storage 508 stores the flag(s) in conjunction with corresponding zone(s), as further disclosed below at block 1016.

At block 1012, the example comparator 506 determines if the current is less than a threshold for one or more corresponding pins or the resistance is more than a threshold. For example, the comparator 506 may determine if the sensed current of each test and/or control is within a defined range of current and/or resistance. In other examples, the comparator 506 perform a comparison metrics against specific values. For example, in an example implementation, the comparator 506 may determine if the sensed current of a test and/or control is less than 50 mA and/or if the sensed resistance is more than 100 Ohms. In other examples, other values may be used. If the example comparator 506 determines that the current is not less than a threshold for one or more corresponding pins or that the resistance is not more than a threshold (block 1012: NO), control continues to block 1016. If the example comparator 506 determines that the current is less than a threshold for one or more corresponding pins or the resistance is more than a threshold (block 1012: YES), the example comparator 506 flags (e.g., marks or outputs a logic value) the corresponding test zone(s) and/or control zone(s) as corresponding to a negative result (block 1014). At block 1016, the example results storage 508 stores the flag(s) in conjunction with corresponding zone(s) and/or the example antenna interface 500 transmits (e.g., via the antenna 115) the results corresponding to the flags. The antenna 115 may also transmit identification information (e.g., device identifier, test number and/or type identifiers, control number and/or type identifiers) with the results. In some examples, the results storage 606 may store a flag indicative that the results have been determined. The flag may be included in the results of subsequent reads. In this manner, the example reader 116 can identify that the test has already been read.

Figure 11A:
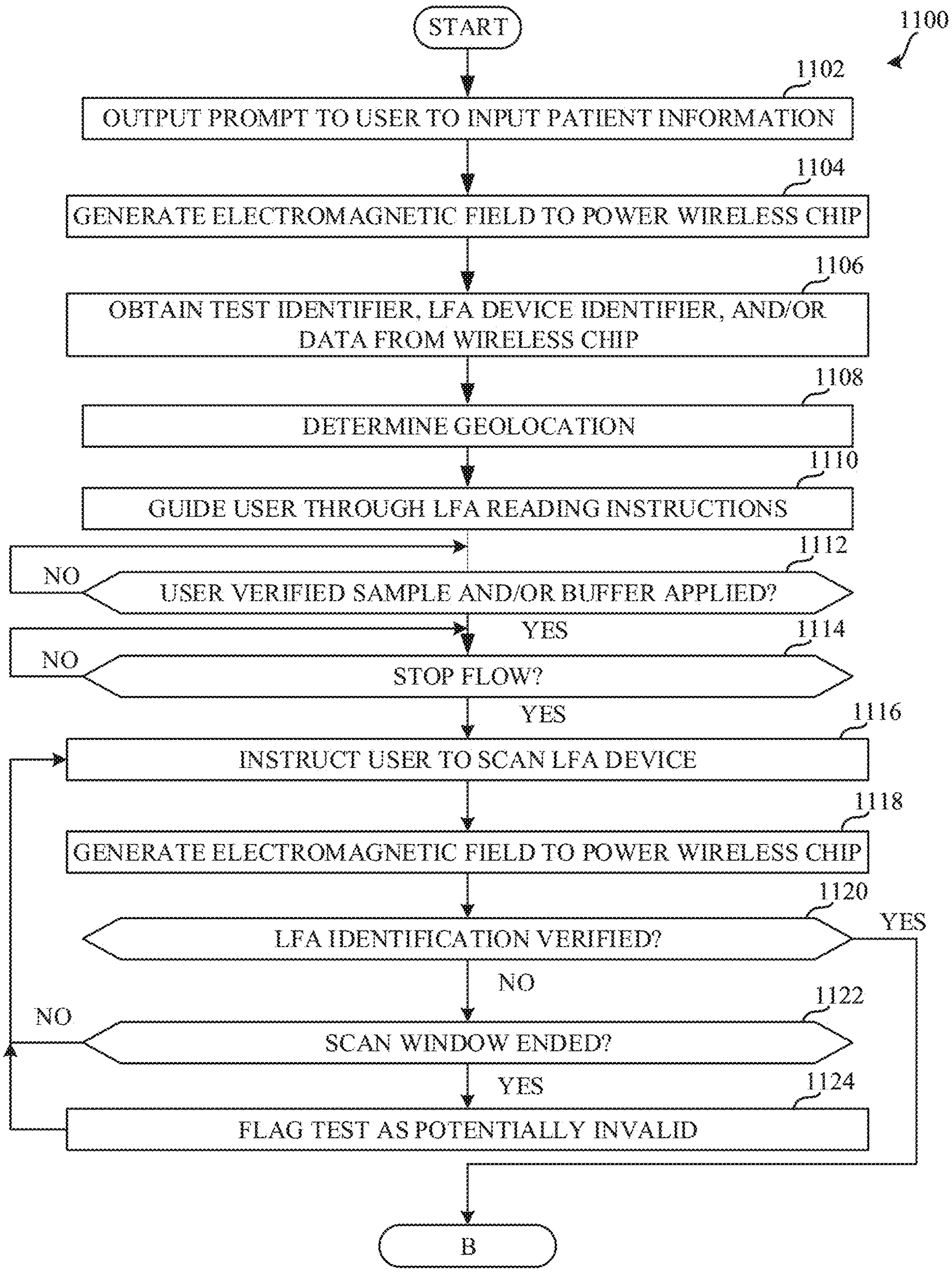
FIGS. 11A-B illustrate a flowchart representative of machine readable instructions which may be executed to implement the machine readable lateral flow immunoassay reader application of FIGS. 1A and/or 6.
Figure 11B:
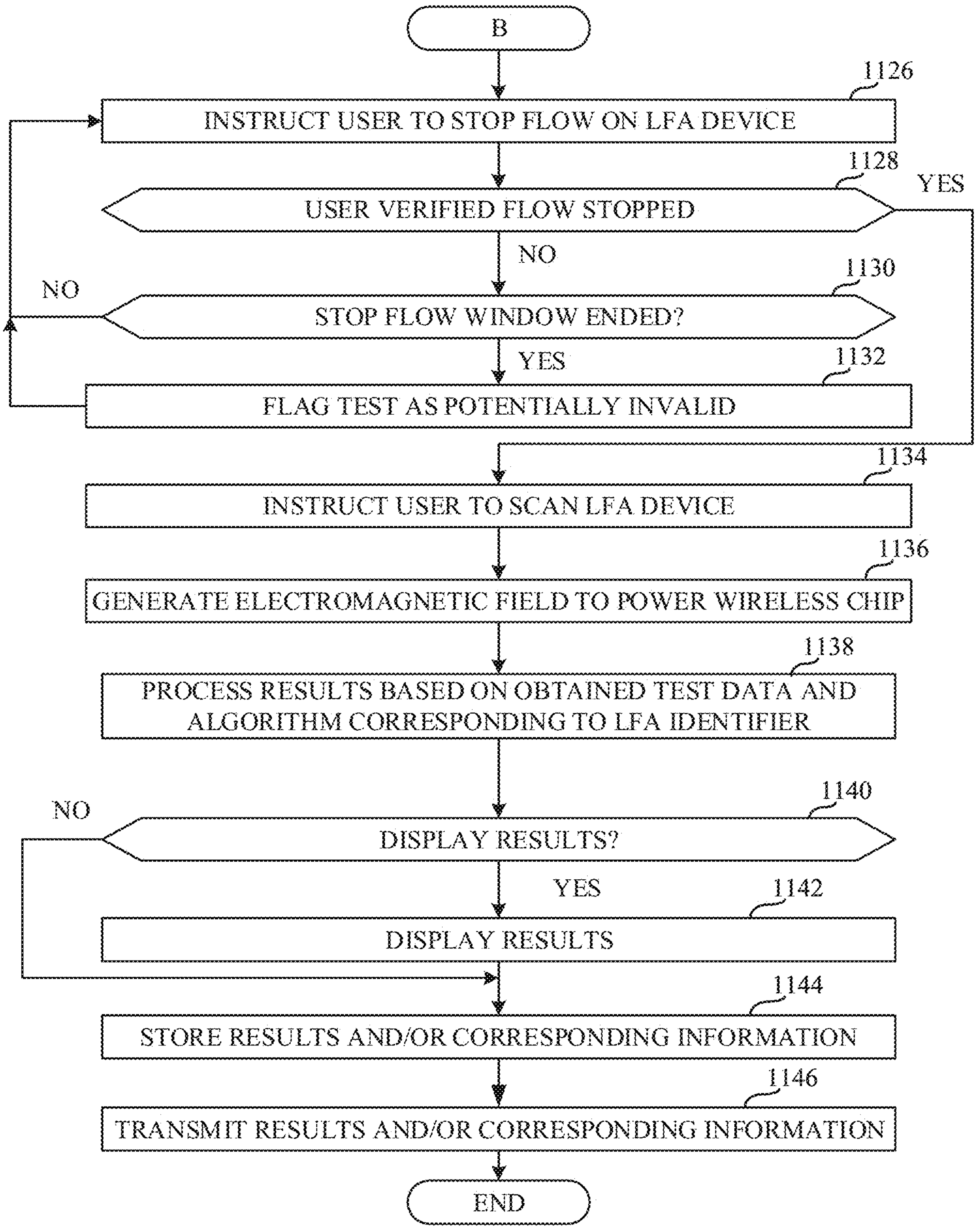

FIGS. 11A-11B illustrate an example flowchart representative of machine readable instructions 1100 that may be executed to implement the example machine readable LFA reader application 117 of FIG. 6 to read test results (e.g., diagnostic test results) of the example machine readable LFA device 104, 300 of FIGS. 1A, 1B, 2A, 2B, 2D, 2E, 2G, 2H, 2L-2R, and/or 3A. Although the instructions 1100 of FIGS. 11A-11B are described in conjunction with the example machine readable LFA device 104, 300 of FIGS. 1A, 1B, 2A, 2B, 2D, 2E, 2G, 2H, 2L-2R, and/or 3A, the example instructions 1100 may be described and/or implemented in conjunction with type of LFA of any structure.

The results determiner 602 instructs the component interface 600 to interface with a user of the reader 116 via the user interface 120. The results determiner 602 may transmit one or more prompts to the user and wait for acknowledgements from the user. For example, if the testing of the LFA 104 not autonomous or semi-autonomous, when the application 117 starts up on the reader 116, the results determiner 602 can transmit instructions to the user of the reader 116. For example, at block 1102, the example results determiner 602 outputs a prompt to the user of the reader 116 instructing the user to input patent information (e.g., name, age, date of birth, gender, etc.). For example, the results determiner 602 instructs the component interface 600 to interface with the user via the user interface 120. The results determiner 602 may transmit one or more prompts to the user and wait for acknowledgements from the user. The patient information may be included (e.g., tagged to the results, included as metadata for the results, etc.) in corresponding information that can be displayed, stored, and/or transmitted to an external database and/or server. In some examples, the external/remote database and/or server is located at or otherwise associated with an EMR, a government agency, an NGO, a doctor's office, a hospital, a hospital information system, a LIMS system, a stock consumption monitor, a clinic, and/or other medical facility, a medical device manufacturer, a medical organization, a health information system, and/or other external entity The results determiner 602 also transmits prompts to the user to register the LFA 104 and/or identify the type of LFA 104. At block 1104, the results determiner 602 instructs the example antenna 118 via the example component interface 600 to generate a magnetic field to power the wireless chip 114 for a first scan (e.g., to identify the LFA device 104). In this manner, the wireless chip 114 can provide (e.g., wirelessly via the example antenna 115) information to the reader 116 while powered. In some examples, the reader 104 can obtain the identification information by scanning a QR code on the LFA device 104 using a camera or having a user manually enter a code on the LFA device 104. The LFA reader application 117 presents an instruction to the user to scan the LFA device 104 (e.g., to bring the reader 116 operating to the reader application 117 into proximity with the LFA device 104). At block 1106, the example results determiner 602 obtains a test identifier (e.g., corresponding to one or more tests that the LFA device is structured to take), an LFA device identifier, a product code, and/or any other encoded or unencoded data from the wireless chip 114. The obtained information may be included (e.g., tagged to the results, included as metadata for the results, etc.) in the corresponding information that can be displayed, stored, and/or transmitted to the external data base and/or server. In some examples, the results determiner 602 uses the obtained information to determine the test type and/or corresponding algorithm to use when obtaining data corresponding to test results from the LFA device 104. In some examples, the results determiner 602 uses the obtained information to authenticate the LFA device 104 and/or prevent the use of an invalid or unauthorized LFA device 104.

At block 1108, the example results determiner 602 determines the geolocation of the LFA device 104. In some examples, the component interface 600 accesses location information from other components of the reader 116 (e.g., if the reader 116 includes a GPS system). In some examples, the geolocation information is received (e.g., accessed, obtained, etc.) from the wireless chip 114. The geolocation information may be included (e.g., tagged to the results, included as metadata for the results, etc.) in corresponding information that can be displayed, stored, and/or transmitted to an external database and/or server.

At block 1110, the example results determiner 602 guides the user of the reader 116 through LFA reading instructions. For example, the results determiner 602 can transmit instructions to (1) instruct the user to apply the sample to the sample pad 106 and wait for user acknowledgement, (2) instruct the user to apply the assay buffer and wait for user acknowledgement, (3) instruct the user to wait for the LFA test, display the time, and/or wait for user acknowledgement, (4) instruct the user to apply a reaction buffer and wait for user acknowledgement, (5) instruct the user to wait for the reactions to occur, display the time, and/or wait for user acknowledgement, etc. In some examples, the results determiner 602 can display an error if, for example, an acknowledgement is not received within a threshold range of time. In a semiautonomous or fully autonomous LFA, some instructions may be eliminated as the LFA 104 may perform one or more of the steps automatically, without the need of the user. The information added may be included (e.g., tagged to the results, included as metadata for the results, etc.) in corresponding information that can be displayed, stored, and/or transmitted to an external database and/or server. In some examples, the external database and/or server is a hospital, a hospital information system, a LIMS system, a stock consumption monitor, a medical facility, a medica device manufacturer, etc.

At block 1112, the example component interface 600 determines whether the user has verified that the sample and/or buffer was applied to the example LFA 104 (e.g., by an acknowledgement on the user interface 120). If the example component interface 600 determines that the user has not verified that the sample and/or buffer has been applied (block 1112: NO), control returns to block 1112 until the user has verified. If the example component interface 600 determines that the user has verified that the sample and/or buffer has been applied (block 1112: YES), the example results determiner 602 determines if flow should be stopped (block 1114). In some examples, the results determiner 602 determines whether flow is to be stopped by tracking a time window, the time window based on the test and/or the LFA identification information. For example, the LFA device 104 of FIGS. 2A-2E and/or 2L-2R uses techniques such as, for example, shearing, cutting, compressing, etc. to reduce or prevent flow on the porous membrane 109 to prevent a product (e.g., hydrogen peroxide) produced at a test or control line from flowing toward the wicking pad 112.

If the example component interface 600 determines that flow should not be stopped (block 1114: NO), control proceeds to block 1114 until the time window ends. If the example component interface 600 determines that flow along the LFA device 104 should be stopped (block 1114: YES), the example component interface 600 instructs the user to scan the LFA device 104 (block 1116). Because the user may conduct multiple tests concurrently from multiple LFA devices within a short duration of time, the user may confuse which test is ready to be read. Accordingly, the LFA reader application 117 instructs the user to scan the LFA device 104 to verify that the device the user scanned is the correct device to move forward with, thereby preventing errors associated with conducting multiple tests concurrently and/or during a short duration of time.

At block 1118, the results determiner 602 instructs the example antenna 118 via the example component interface 600 to generate a magnetic field to power the wireless chip 114 to perform a second scan (e.g., to validate that the user is reading the correct LFA device 104). At block 1120, the example results determiner 602 determines if the LFA device identification is verified (e.g., if the identification of the first scan matches the identification of the second scan). If the example results determiner 602 determines that the LFA device identification has been verified (block 1120: YES), control continues to block 1126 of FIG. 11B. If the example results determiner 602 determines that the LFA device identification has not been verified (e.g., the identifier from the second scan does not match the identifier from the first scan) (block 1120: NO), the example results determiner 602 determines if the scan window (e.g., an amount of time corresponding to when the LFA device 104 should be verified has ended based on the test and/or LFA device type) has ended (block 1122). If the scan window has ended, the results may be less accurate. In some examples, the component interface 600 displays a timer corresponding to the test window in the example user interface 120.

If the example results determiner 602 determines that the scan window has not ended (block 1122: NO), control returns to block 1116. If the example results determiner 602 determines that the scan window has ended (block 1122: YES), the example results determiner 602 flags the test as potentially invalid (block 1124) and control returns to block 1116. In some examples, the test can continue but the results will be flagged with being read after the scan window (e.g., along timing information corresponding to how long after the scan window were the results determined). In some examples, the test is marked as invalided and the component interface 600 identifies the test as invalid.

At block 1126, the example component interface 600 transmits a prompt to the user to stop the flow of the LFA device 104 (block 1114). For example, the component interface 600 may prompt the user to move the switch 278, 292 from the first position to the second position to cause the flow arrestors 280 to cut, shear, compress, and/or otherwise stop impede, and/or resist flow. At block 1128, the results determiner 602 determines whether the user has verified that the flow has been stopped (e.g., via a prompt on the user interface 120). If the example results determiner 602 determines that the user has verified that the flow has stopped (block 1128: YES), control continues to block 1134. If the example results determiner 602 determines that the user has not verified that the flow has stopped (block 1128: NO), the example results determiner 602 determines if the stop flow window (e.g., an amount of time corresponding to when the LFA device 104 should be sheared has ended based on the test and/or LFA device type) has ended (block 1130). If the stop flow window has ended, the results may be less accurate. In some examples, the component interface 600 displays a timer corresponding to the test window in the example user interface 120.

If the example results determiner 602 determines that the stop flow window has not ended (block 1130: NO), control returns to block 1126. If the example results determiner 602 determines that the scan window has ended (block 1130: YES), the example results determiner 602 flags the test as potentially invalid (block 1132) and control returns to block 1126. In some examples, the test can continue but the results will be flagged with being read after the stop flow window (e.g., along timing information corresponding to how long after the stop flow window were the results determined). In some examples, the test is marked as invalided and the component interface 600 identifies the test as invalid.

At block 1134, the example component interface 600 instructs the user to scan the LFA device 104. At block 1136, the results determiner 602 instructs the example antenna 118 via the example component interface 600 to generate a magnetic field to power the wireless chip 114 to perform a third scan (e.g., to obtain the digital values from the LFA device 104). As described above, the digital values may correspond to sensed voltage(s) and/or current(s) from one or more test zones and/or control zones. At block 1138, the example results determiner 602 processes the results based on the obtained test data (e.g., the digital voltages and/or current values tagged to test zones and/or control zones) and an algorithm that corresponds to the LFA identifier. Because the machine readable LFA reader application 117 is capable of scanning different LFA devices and the algorithms for determining and/or categorizing the results based on obtained data may be different for different devices and/or different diagnostic tests, the LFA reader application 117 determines which algorithm to apply based on the test identifier from the LFA device 104 and uses the obtained test data and the selected algorithm to determine the test results. The algorithm may define the threshold that identifies which voltage and/or current values result in a positive result and which voltage and/or current values result in a negative result. Additionally, the algorithm may determine how many number of samples must be positive to result in a positive result (e.g., 5 out of 5 (i.e., all), 4 out of 5 (i.e., a percentage), etc.). In some examples, the wireless chip 114 determines the test results at the wireless chip 114. In such examples, the results determiner 602 may display and/or store the obtained results based on the corresponding algorithm. In this manner, the results determine 602 associated the manufacturing data encoded on the wireless chip 114 (e.g., an ASIC of the wireless chip 114) to the test result without connecting to a secondary system.

At block 1140, the example results determiner 602 determines if results should be displayed on the example user interface 120. For example, for privacy protection a patient may wish to have the results sent to their doctor as opposed to being displayed to the technician. Accordingly, a setting may be enabled or disabled corresponding to whether to display or not to display the results to preserve the privacy of the patient. If the example results determiner 602 determines that the results should not be displayed (e.g., are kept private from the user implementing the test) (block 1140: NO), control continues to block 1144. If the example results determiner 602 determines that the results should be displayed (block 1140: YES), the example component interface 600 instructs the user interface 120 to display the results (block 1142). At block 1144, the example results storage 606 stores the results, corresponding information (e.g., device and/or test identification information), and/or contextual information or supplementary (e.g., time, date, patient information, location information, lot number, expiration date, expiry date, test information, signal quality information, chain of custody, operator information, etc.). In some examples, the results are tagged to a patient, and the corresponding information and/or contextual data are tagged to the results as metadata. Accordingly, the test data can be immediately associated with supplementary data sets.

At block 1146, the example component interface 600 transmits instructions to a transmitter of the reader 116 to transmit the results, corresponding information (e.g., device and/or test identification information), and/or contextual or supplementary information (e.g., time, date, patient information, location information, lot number, expiration date, expiry date, test information, signal quality information, chain of custody, operator information, etc.). The example component interface 600 may transmit the results, corresponding information and/or contextual or supplementary information over a network to one or more remote databases and/or servers located at or otherwise associated with an EMR, a government agency, value propositions for NGOs, a doctor's office, a hospital, a hospital information system, a LIMS system, a stock consumption monitor, a clinic, and/or other medical facility, a medical device manufacturer, a medical organization, a health information system, and/or other external entity. In this manner, different actions may be taken based on the reception of test data. For example, a hospital, doctor's office, manufacturer, agency, etc. can automatically track the use of LFA devices when they are scanned for reading, automatically re-ordering additional inventory from a supplier, generating an alert of an outbreak of a disease or pathogen to a particular area, etc. In some examples, the results and/or other data are uploaded automatically. In some examples, the results and/or other data are uploaded in real time or near real time. In some examples, the reader 116 encrypts the information for transmission to the external database and/or server. If the results and corresponding information is transmitted to a monitoring entity, the monitoring entity can process the results and/or perform statistical analysis to determine whether there is an outbreak of disease, identify whether LFAs are being counterfeited, etc., based on multiple received results from one or more improved LFA reader applications. In some examples, the results determiner 602 prevents duplicate results from being transmitted (e.g., when a device has been flagged as being read more than once). If a network connection is not currently present, the example component interface 600 may delay instructions to the transmitter until a network connection is established. Additionally or alternatively, the example component interface 600 may transmit results from the results storage 606 periodically, aperiodically, and/or based on a trigger (e.g., a result request from a measuring entity).

Figure 12:
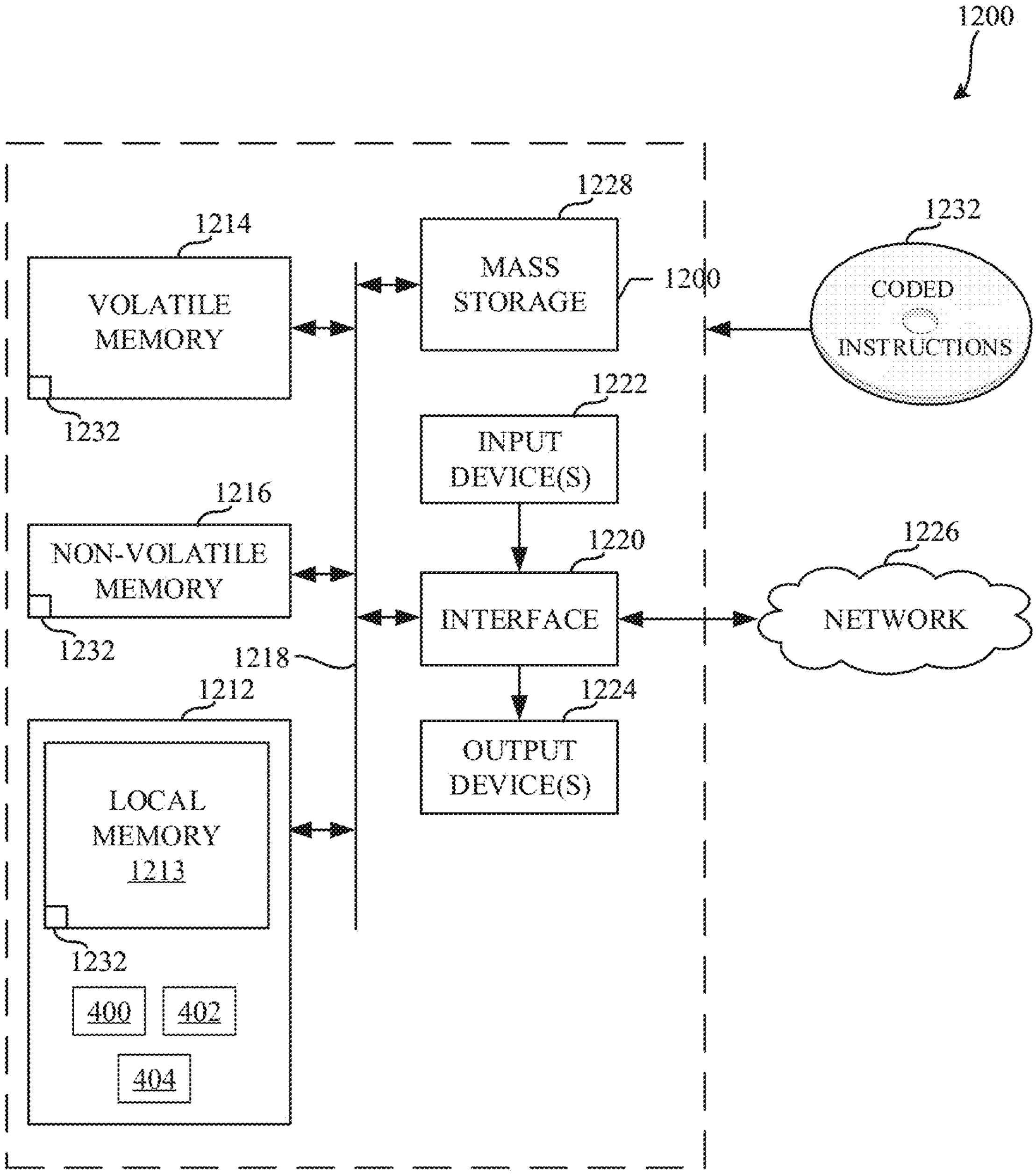
FIG. 12 is a block diagram of an example processing platform structured to execute the instructions of FIG. 7 to implement the lateral flow immunoassay generator of FIGS. 1A, 1B, and/or 4.

FIG. 12 is a block diagram of an example processor platform 1200 structured to execute the instructions of FIG. 7 to implement the machine readable LFA generator 102 of FIG. 4. The processor platform 1200 can be, for example, a server, a personal computer, a workstation, a self-learning machine (e.g., a neural network), an Internet appliance, or any other type of computing device.

The processor platform 1200 of the illustrated example includes a processor 1212. The processor 1212 of the illustrated example is hardware. For example, the processor 1212 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the example user interface 400, the example part generator 402, and the example part applicator 404.

The processor 1212 of the illustrated example includes a local memory 1213 (e.g., a cache). The processor 1212 of the illustrated example is in communication with a main memory including a volatile memory 1214 and a non-volatile memory 1216 via a bus 1218. The volatile memory 1214 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1216 may be implemented by flash memory and/or any other desired type of memory device. Access to the main memory 1214, 1216 is controlled by a memory controller.

The processor platform 1200 of the illustrated example also includes an interface circuit 1220. The interface circuit 1220 may be implemented by any type of interface standard, such as an Ethernet interface, a universal serial bus (USB), a Bluetooth® interface, a near field communication (NFC) interface, and/or a PCI express interface.

In the illustrated example, one or more input devices 1222 are connected to the interface circuit 1220. The input device(s) 1222 permit(s) a user to enter data and/or commands into the processor 1212. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1224 are also connected to the interface circuit 1220 of the illustrated example. The output devices 1224 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 1220 of the illustrated example, thus, typically includes a graphics driver card, a graphics driver chip and/or a graphics driver processor.

The interface circuit 1220 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1226. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1200 of the illustrated example also includes one or more mass storage devices 1228 for storing software and/or data. Examples of such mass storage devices 1228 include floppy disk drives, hard drive disks, compact disk drives, Blu-ray disk drives, redundant array of independent disks (RAID) systems, and digital versatile disk (DVD) drives.

The machine executable instructions 1232 of FIG. 7 may be stored in the mass storage device 1228, in the volatile memory 1214, in the non-volatile memory 1216, and/or on a removable non-transitory computer readable storage medium such as a CD or DVD.

Figure 13:
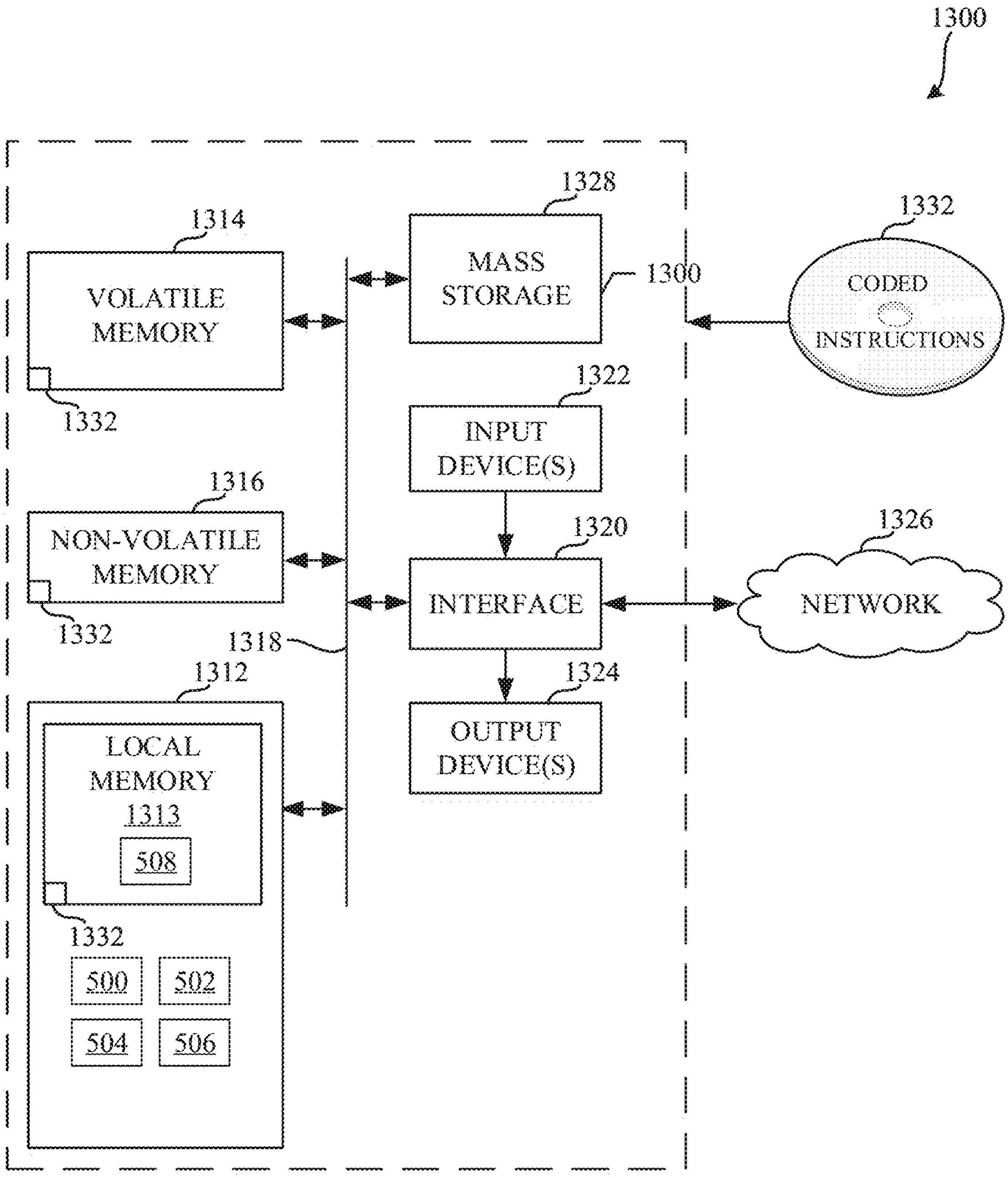
FIG. 13 is a block diagram of an example processing platform structured to execute the instructions of FIGS. 8A-10 to implement the wireless chip of FIGS. 1A, 2A, 2B, 2I-2K, 3A, and/or 5.

FIG. 13 is a block diagram of an example processor platform 1300 structured to execute the instructions of FIGS. 8A-10 to implement the wireless chip 114 of FIG. 5. The processor platform 1300 can be, for example, a machine readable LFA device, a self-learning machine (e.g., a neural network), or any other type of computing device.

The processor platform 1300 of the illustrated example includes a processor 1312. The processor 1312 of the illustrated example is hardware. For example, the processor 1312 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the example antenna interface 500, the example driver 502, the example sensor 504, and the example comparator 506.

The processor 1312 of the illustrated example includes a local memory 1313 (e.g., a cache). The processor 1312 of the illustrated example is in communication with a main memory including a volatile memory 1314 and a non-volatile memory 1316 via a bus 1318. The volatile memory 1314 may be implemented by SDRAM, DRAM, RDRAM® and/or any other type of random access memory device. The non-volatile memory 1316 may be implemented by flash memory and/or any other desired type of memory device. Access to the main memory 1314, 1316 is controlled by a memory controller. The example local memory 1313 implements the results storage 508.

The processor platform 1300 of the illustrated example also includes an interface circuit 1320. The interface circuit 1320 may be implemented by any type of interface standard, such as an Ethernet interface, a USB, a Bluetooth® interface, an NFC interface, and/or a PCI express interface.

In the illustrated example, one or more input devices 1322 are connected to the interface circuit 1320. The input device(s) 1322 permit(s) a user to enter data and/or commands into the processor 1312. The input device(s) can be implemented by, for example, an audio sensor, a button, and/or any other type of input device(s).

One or more output devices 1324 are also connected to the interface circuit 1320 of the illustrated example. The output devices 1324 can be implemented, for example, by display devices (e.g., an LED, an OLED, an LCD, a CRT display, an IPS display, a touchscreen, etc.), and/or speaker. The interface circuit 1320 of the illustrated example, thus, typically includes a graphics driver card, a graphics driver chip and/or a graphics driver processor.

The interface circuit 1320 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1326. The communication can be via, for example, an Ethernet connection, a DSL connection, a telephone line connection, a coaxial cable system, a satellite system, a line-of-site wireless system, a cellular telephone system, etc.

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and DVD drives.

The machine executable instructions 1332 of FIGS. 8A-10 may be stored in the mass storage device 1328, in the volatile memory 1314, in the non-volatile memory 1316, and/or on a removable non-transitory computer readable storage medium such as a CD or DVD.

Figure 14:
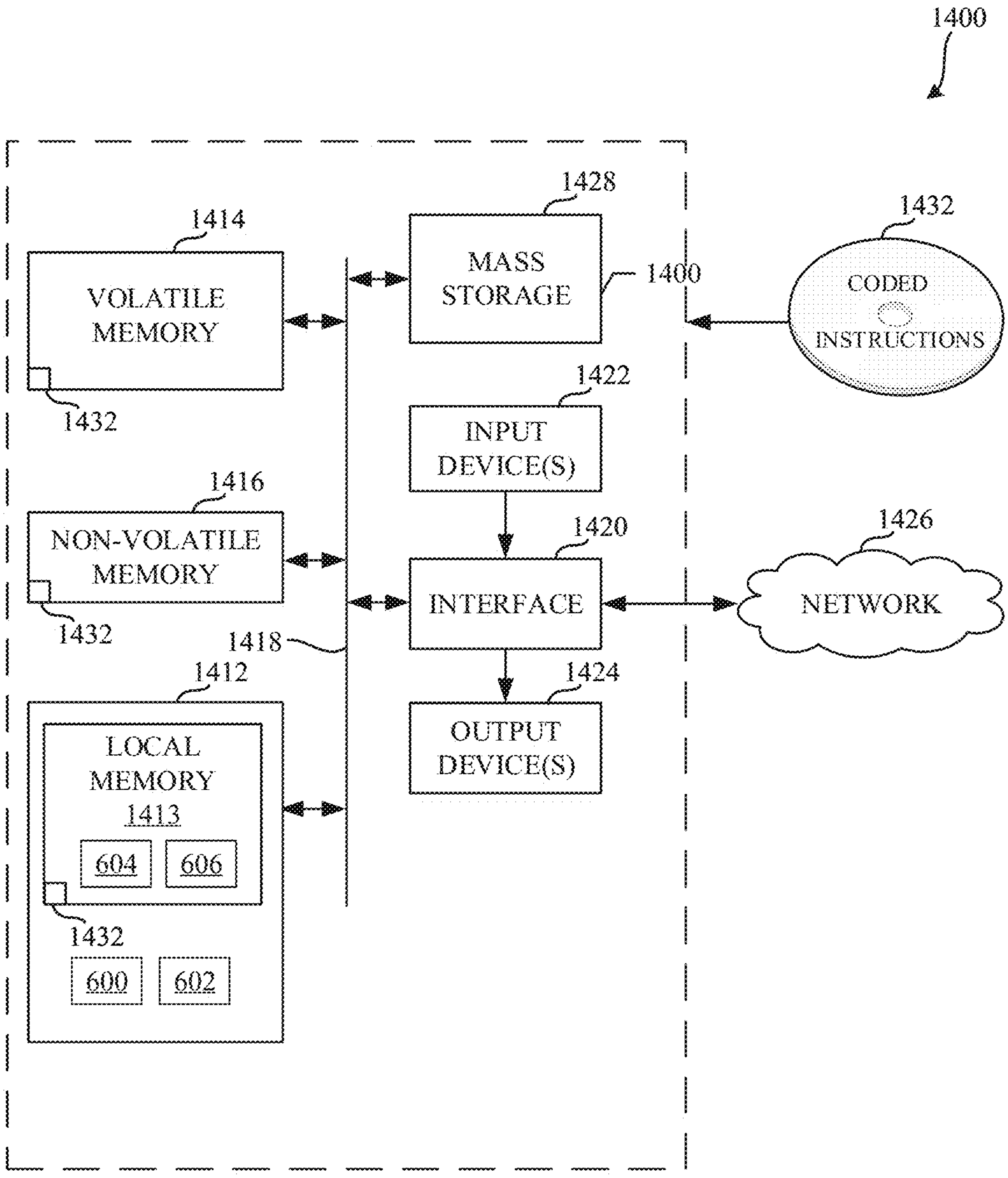
FIG. 14 is a block diagram of an example processing platform structured to execute the instructions of FIGS. 11A-11B to implement the machine readable lateral flow immunoassay reader application of FIGS. 1A, and/or 6.

FIG. 14 is a block diagram of an example processor platform 1400 structured to execute the instructions of FIGS. 11A-B to implement the machine readable LFA reader application 117 of FIG. 3. The processor platform 1400 can be, for example, a personal computer, a workstation, a self-learning machine (e.g., a neural network), a mobile device (e.g., a cell phone, a smart phone, a tablet such as an iPad™), a personal digital assistant (PDA), a personal video recorder, or any other type of computing device.

The processor platform 1400 of the illustrated example includes a processor 1412. The processor 1412 of the illustrated example is hardware. For example, the processor 1412 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the example component interface 600, and the example results determiner 602.

The processor 1412 of the illustrated example includes a local memory 1413 (e.g., a cache). The processor 1412 of the illustrated example is in communication with a main memory including a volatile memory 1414 and a non-volatile memory 1416 via a bus 1418. The volatile memory 1414 may be implemented by SDRAM, DRAM, RDRAM® and/or any other type of random access memory device. The non-volatile memory 1416 may be implemented by flash memory and/or any other desired type of memory device. Access to the main memory 1414, 1416 is controlled by a memory controller. The example local memory 1413 implements the example test type storage 604 and the example results storage 606.

The processor platform 1400 of the illustrated example also includes an interface circuit 1420. The interface circuit 1420 may be implemented by any type of interface standard, such as an Ethernet interface, a USB, a Bluetooth® interface, an NFC interface, and/or a PCI express interface.

In the illustrated example, one or more input devices 1422 are connected to the interface circuit 1420. The input device(s) 1422 permit(s) a user to enter data and/or commands into the processor 1412. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1424 are also connected to the interface circuit 1420 of the illustrated example. The output devices 1424 can be implemented, for example, by display devices (e.g., an LED, an OLED, an LCD, a CRT display, an IPS display, a touchscreen, etc.), a tactile output device, a printer and/or speaker. The interface circuit 1420 of the illustrated example, thus, typically includes a graphics driver card, a graphics driver chip and/or a graphics driver processor.

The interface circuit 1420 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1426. The communication can be via, for example, an Ethernet connection, a DSL connection, a telephone line connection, a coaxial cable system, a satellite system, a line-of-site wireless system, a cellular telephone system, etc.

The processor platform 1400 of the illustrated example also includes one or more mass storage devices 1428 for storing software and/or data. Examples of such mass storage devices 1428 include floppy disk drives, hard drive disks, compact disk drives, Blu-ray disk drives, RAID systems, and DVD drives.

The machine executable instructions 1432 of FIGS. 11A-B may be stored in the mass storage device 1428, in the volatile memory 1414, in the non-volatile memory 1416, and/or on a removable non-transitory computer readable storage medium such as a CD or DVD.

Figure 15:
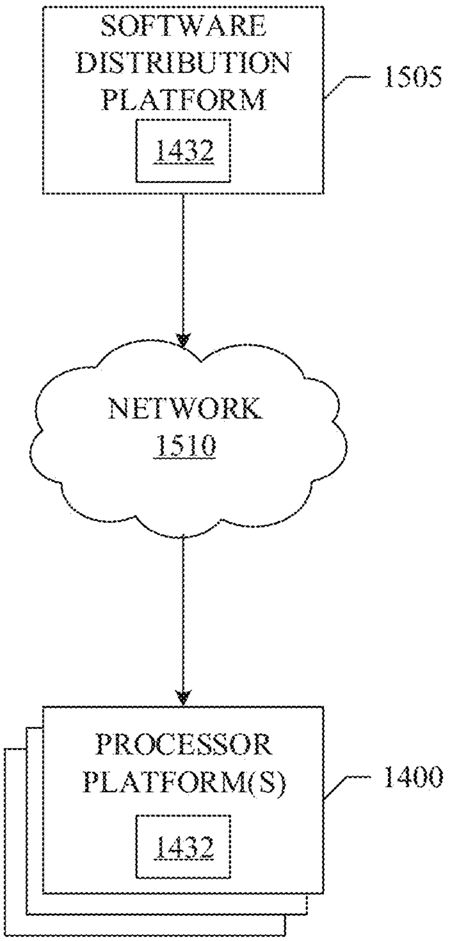
FIG. 15 is a block diagram of an example software distribution platform to distribute software (e.g., software corresponding to the example computer readable instructions of FIGS. 11A-11B) to client devices such as consumers (e.g., for license, sale and/or use), retailers (e.g., for sale, re-sale, license, and/or sub-license), and/or original equipment manufacturers (OEMs) (e.g., for inclusion in products to be distributed to, for example, retailers and/or to direct buy customers).

A block diagram illustrating an example software distribution platform 1505 to distribute software such as the example computer readable instructions 1432 of FIG. 14 to third parties is illustrated in FIG. 15. The example software distribution platform 1505 may be implemented by any computer server, data facility, cloud service, etc., capable of storing and transmitting software to other computing devices. The third parties may be customers of the entity owning and/or operating the software distribution platform. For example, the entity that owns and/or operates the software distribution platform may be a developer, a seller, and/or a licensor of software such as the example computer readable instructions 1432 of FIG. 14. The third parties may be consumers, users, retailers, OEMs, etc., who purchase and/or license the software for use and/or re-sale and/or sub-licensing. In the illustrated example, the software distribution platform 1505 includes one or more servers and one or more storage devices. The storage devices store the computer readable instructions 1432, which may correspond to the example computer readable instructions 1100 of FIGS. 11A and/or 11B, as described above. The one or more servers of the example software distribution platform 1505 are in communication with a network 1510, which may correspond to any one or more of the Internet and/or any of the example networks described above. In some examples, the one or more servers are responsive to requests to transmit the software to a requesting party as part of a commercial transaction. Payment for the delivery, sale and/or license of the software may be handled by the one or more servers of the software distribution platform and/or via a third party payment entity. The servers enable purchasers and/or licensors to download the computer readable instructions 1432 from the software distribution platform 1505. For example, the software, which may correspond to the example computer readable instructions 1100 of FIGS. 11A and/or 11B, may be downloaded to the example processor platform 1400, which is to execute the computer readable instructions 1432 to implement the machine readable LFA reader application 117 of FIGS. 1 and/or 6. In some example, one or more servers of the software distribution platform 1505 periodically offer, transmit, and/or force updates to the software (e.g., the example computer readable instructions 1432 of FIG. 14) to ensure improvements, patches, updates, etc. are distributed and applied to the software at the end user devices.

Example methods, apparatus, systems, and articles of manufacture to make and/or process a diagnostic test devices are disclosed herein. Further examples and combinations thereof include the following: Example 1 includes an apparatus for use with a fluid sample, the apparatus comprising a sensor to measure a current between a first electrode coupled to a first zone corresponding to a target analyze on a porous media of a device and a second electrode coupled to a second zone of the porous media of the device, a processor to compare the current to a threshold, and when the current is more than the threshold, identify that the target analyte is present in a sample, and an antenna to wirelessly transmit results.

Example 2 includes the apparatus of example 1, wherein the processor is to, when the current is less than the threshold, identify that the target analyte is not present in the sample.

Example 3 includes the apparatus of example 1, wherein the porous membrane is to generate the current when the target analyte is present in the sample.

Example 4 includes the apparatus of example 1, wherein the sensor is to measure a second current between a third electrode and a fourth electrode coupled to a control zone, and the processor is to compare the second current to the threshold, and when the second current is more than the threshold, identify that the test is ready to be read, the results including an indication of whether the test is ready to be read.

Example 5 includes the apparatus of example 4, wherein the control zone corresponds to at least one of antibodies, or analytes, or antigens on the porous media of the device.

Example 6 includes the apparatus of example 1, wherein the antenna is to wirelessly transmit the results to a reader.

Example 7 includes a method for use with a fluid sample, the method comprising measuring a current between a first electrode coupled to a first zone corresponding to a target analyze on a porous media of a test strip and a second electrode coupled to a second zone of the porous media of the test strip, comparing, by executing instructions with a processor, the current to a threshold, when the current is more than the threshold, identifying that the target analyte is present in a sample, and wirelessly transmitting results.

Example 8 includes the method of example 7, further including, when the current is less than the threshold, identifying that the target analyte is not present in the sample.

Example 9 includes the method of example 7, wherein the current is generated when the target analyte is present in the sample.

Example 10 includes the method of example 7, further including measuring a second current between a third electrode and a fourth electrode coupled to the test zone corresponding to a control zone, comparing the second current to the threshold, and when the second current is more than the threshold, identifying that the test is ready to be read, the results including an indication of whether the test is ready to be read.

Example 11 includes the method of example 10, wherein the control zone corresponds to at least one of analytes, analytes, or antibodies on the porous media of the test strip.

Example 12 includes the method of example 7, further including wirelessly transmitting the results to a reader.

Example 13 includes a device for use with a fluid sample, the device comprising a conjugate pad including conjugates corresponding a target analyte, the conjugate being labeled with at least one of gold nanoparticles or glucose oxidase, a test zone including at least one of immobilized antigens corresponding to the target analyte or immobilized antibodies corresponding to the target analyte, and a bioelectrochemical cell to generate a current when the target analyte is in a sample.

Example 14 includes the device of example 13, wherein the bioelectrochemical cell is impregnated with at least one of an enzyme substrate, a reducing agent, an electron mediator, or a redox-species.

Example 15 includes the device of example 14, wherein the conjugates are capable of mixing with the at least one of the enzyme substrate, the reducing agent, the electron mediator, or the redox-species to generate the current.

Example 16 includes the device of example 13, wherein the bioelectrochemical cell is fluidically coupled to the test zone.

Example 17 includes the device of example 13, wherein the bioelectrochemical cell is structured to be fluidically coupled to the test zone after user interference.

Example 18 includes the device of example 13, further including an inlet to separate the bioelectrochemical cell into a first portion and a second portion, the inlet to allow a buffer to flow in the inlet to resuspend dried reagents of the bioelectrochemical cell, the resuspension to generate the current at the bioelectrochemical cell.

Example 19 includes the device of example 13, wherein the bioelectrochemical cell is a concentration cell.

Example 20 includes the device of example 13, further including a wireless chip coupled to a first end of the bioelectrochemical cell and a second end of the bioelectrochemical cell.

Example 21 includes the device of example 20, wherein the wireless chip is to sense the current between the first end and the second end to identify whether the target analyte is present in the sample.

Example 22 includes the device of example 21, further including a sensor to determine a result based on the current drop across the bioelectrochemical cell, the result indicative of the target analyte present in the sample, and the wireless chip to wirelessly transmit the result to a reader.

Example 23 includes the device of example 22, wherein the reader is a smart phone application.

Example 24 includes the device of example 13, wherein the bioelectrochemical cell is to cause a reaction resulting in a generation of hydrogen peroxide, further including an electrode coupled to the bio electrochemical cell, the electrode made of at least one of copper or screen printed carbon doped with ferrocyanide, the at least one of the copper or screen printed carbon doped with ferrocyanide to oxidize and the hydrogen peroxide to reduce, resulting in a release of an electron corresponding to the current.

Example 25 includes an apparatus for use with a fluid sample, the apparatus comprising a sensor to measure a resistance between a first electrode coupled to a first end of a test line corresponding to a target analyte and a second electrode coupled to a second end of the test line, the test line on a porous media, a processor to compare the resistance to a threshold, and when the resistance is more than the threshold, identify that the target analyte is present in a sample, and an antenna to wirelessly transmit results corresponding to the identification.

Example 26 includes the apparatus of example 25, wherein the processor is to, when the resistance is less than the threshold, identifying that the target analyte is not present in the sample.

Example 27 includes the apparatus of example 25, wherein the test line is a connection when the target analyte is present in the sample and is an open circuit when the target analyte is not present in the sample.

Example 28 includes the apparatus of example 25, wherein, when the target analyte is present in the sample and silver is applied to the test line, the silver amplifies at the test line until the silver creates a connection between the first electrode and the second electrode.

Example 29 includes the apparatus of example 25, further including a driver to output a voltage to at least one of the first electrode or the second electrode, the voltage causing current to flow between the first electrode and the second electrode, the current corresponding to the resistance.

Example 30 includes the apparatus of example 25, wherein the resistance a first resistance, wherein the sensor is to measure a second resistance between a first end and a second end of a control line, and the processor is to compare the second resistance to the threshold, and when the second resistance is more than the threshold, identify that the test is ready to be read, the results including an indication of whether the test is ready to be read.

Example 31 includes the apparatus of example 30, wherein the control line corresponds to excess analytes on the porous media.

Example 32 includes a method for use with a fluid sample, the method comprising measuring a resistance between a first electrode coupled to a first end of a test line corresponding to a target analyte and a second electrode coupled to a second end of the test line, the test line on a porous media, comparing, by executing an instruction with a processor, the resistance to a threshold, when the resistance is more than the threshold, identifying that the target analyte is present in a sample, and wirelessly transmitting results corresponding to the identification.

Example 33 includes the method of example 32, further including, when the resistance is less than the threshold, identifying that the target analyte is not present in the sample.

Example 34 includes the method of example 32, wherein the test line is a connection when the target analyte is present in the sample and is an open circuit when the target analyte is not present in the sample.

Example 35 includes the method of example 32, wherein, when the target analyte is present in the sample and silver is applied to the test line, the silver amplifies at the test line until the silver creates a connection between the first electrode and the second electrode.

Example 36 includes the method of example 32, further including outputting a voltage to at least one of the first electrode or the second electrode, the voltage causing current corresponding to the resistance to flow between the first electrode and the second electrode.

Example 37 includes the method of example 32, wherein the resistance is a first resistance, the method further including measuring a second resistance between a first end and a second end of a control line, comparing the second resistance to the threshold, and when the second resistance is more than the threshold, identifying that the test is ready to be read, the results including an indication of whether the test is ready to be read.

Example 38 includes the method of example 37, wherein the control line corresponds to excess analytes on the porous media.

Example 39 includes a device for use with a fluid sample, the device comprising a conjugate pad including conjugates corresponding a target analyte, the conjugates labeled with gold, and a test zone including at least one of immobilized antigens corresponding to the target analyte or immobilized antibodies corresponding to the target analyte, the test zone to immobilize the gold at the test zone, and when a solution is applied to the test zone, amplify silver onto the gold.

Example 40 includes the device of example 39, further including a first electrode coupled to a first section of the test zone and a second electrode coupled to a second section of the test zone, the silver amplifying to more than a threshold size resulting in a connection between the first electrode and the second electrode.

Example 41 includes the device of example 39, further including a wireless chip coupled to a first end of the test zone and a second end of the test zone, the wireless chip including a driver to apply a voltage to the first end of the test zone.

Example 42 includes the device of example 41, wherein the wireless chip includes a sensor to sense a voltage drop across the first end and the second end, and a processor to identify whether the target analyte is present in a sample based on the voltage drop.

Example 43 includes the device of example 42, further including an antenna coupled to the wireless chip, the antenna to wirelessly transmit a result to a reader, the result corresponding to whether the target analyte is present in the sample.

Example 44 includes the device of example 43, wherein the reader is a smart phone application.

Example 45 includes the device of example 43, wherein the antenna is wrapped around the wireless chip, the conjugate pad, and the test zone.

Example 46 includes a method comprising obtaining a result to a fluid sample-based test from a wireless chip on a device, displaying the result on a user interface, and transmitting the result and corresponding information to at least one of an external database or an external server.

Example 47 includes the method of example 46, wherein the results are not displayed or indicated on the device, and the obtaining of the results includes obtaining the results in a machine-readable format from the device.

Example 48 includes the method of example 46, wherein the corresponding information includes at least one of a patient identifier, a device identifier, a timestamp, a number of test reads, location information, or demographic information.

Example 49 includes the method of example 46, further including displaying reading instructions on the user interface.

Example 50 includes the method of example 46, further including, in response to receiving timing information from the wireless chip, displaying an amount of time via the user interface until the device is ready to be read.

Example 51 includes the method of example 46, wherein the result identify whether a sample supplied to the device tested positive or negative for a disease or condition.

Example 52 includes a non-transitory computer readable storage medium comprising instructions which, when executed, cause a machine to at least obtain a result to a fluid sample-based test from a wireless chip on a device, display the result on a user interface, and transmit the result and corresponding information to at least one of an external database or an external server.

Example 53 includes the computer readable storage medium of example 52, wherein the results are not displayed or indicated on the device, and the instructions, when executed, cause the machine to obtain the results in a machine-readable format from the device.

Example 54 includes the computer readable storage medium of example 52, wherein the corresponding information includes at least one of a patient identifier, a device identifier, a timestamp, a number of test reads, location information, or demographic information.

Example 55 includes the computer readable storage medium of example 52, wherein the instructions cause the machine to display reading instructions on the user interface.

Example 56 includes the computer readable storage medium of example 52, wherein the instructions cause the machine to, in response to receiving timing information from the wireless chip, display an amount of time via the user interface until the device is ready to be read.

Example 57 includes the computer readable storage medium of example 52, wherein the result indicates whether a sample supplied to the device tested positive or negative for a disease or condition.

Example 58 includes an apparatus comprising an antenna to obtain a result to a fluid sample-based test from a wireless chip on a device, and a user interface to display the result, the antenna to transmit the result and corresponding information to at least one of an external database or an external server.

Example 59 includes the apparatus of example 58, wherein the results are not displayed or indicated on the device, and the antenna is to obtain the results in a machine-readable format from the device.

Example 60 includes the apparatus of example 58, wherein the corresponding information includes at least one of a patient identifier, a device identifier, a timestamp, a number of test reads, location information, or demographic information.

Example 61 includes the apparatus of example 58, wherein the user interface is to display reading instructions.

Example 62 includes the apparatus of example 58, wherein the user interface is to, in response to receiving timing information from the wireless chip, display an amount of time until the device is ready to be read.

Example 63 includes the apparatus of example 58, wherein the result indicates whether a sample supplied to the device tested positive or negative for a disease or condition.

Example 64 includes a non-visual indicating device for use with a fluid sample, the non-visual indicating device comprising a timer to initiate in response to power received from a bioelectrochemical cell, and an interface to, in response to sensing an electromagnetic field from an external device, transmit at least one of (A) a time indicated by the timer or (B) a threshold duration of time when the time indicated by the timer is less than the threshold duration of time.

Example 65 includes the non-visual indicating device of example 64, wherein the interface is to transmit the at least one of the time indicated by the timer or the threshold duration of time to the device that generated the electromagnetic field.

Example 66 includes the non-visual indicating device of example 64, wherein the threshold duration of time corresponds to an assay time.

Example 67 includes the non-visual indicating device of example 64, wherein the time being less than the threshold duration of time corresponds to an incomplete assay.

Example 68 includes the non-visual indicating device of example 64, wherein the bioelectrochemical cell is a first biofuel cell, further including a comparator to determine if a voltage drop across a second biofuel cell is above a threshold voltage when the time indicated by the timer is greater than the threshold duration of time.

Example 69 includes the non-visual indicating device of example 68, wherein the interface is to transmit a result to the device that generated the electromagnetic field based on the determination of whether the voltage drop is above the threshold voltage.

Example 70 includes a system comprising a non-visual indicating device to transmit a test result when an electromagnetic field is sensed, and a reader to generate the electromagnetic field, obtain the test result, and send the test result to at least one of an external database or an external server.

Example 71 includes the system of example 70, wherein the non-visual indicating device is to determine the test result based on at least one of a current or a voltage.

Example 72 includes the system of example 71, wherein the non-visual indicating device includes a bioelectrochemical cell to generate the at least one of the current or the voltage.

Example 73 includes the system of example 70, wherein the non-visual indicating device includes a wireless chip to transmit the test result.

Example 74 includes the system of example 70, wherein the electromagnetic field powers a wireless chip in the non-visual indicating device via an antenna of the non-visual indicating device.

Example 75 includes the system of example 74, wherein the antenna transmits the test result to the reader.

Example 76 includes the system of example 70, wherein the reader is implemented in a portable computing device.

Example 77 includes the system of example 70, wherein the reader displays the test result on a user interface.

Example 78 includes a device for use with a fluid sample, the device comprising a conjugate pad including conjugates corresponding a target analyte, the conjugate labeled with at least one of gold nanoparticles or glucose oxidase, a porous media including a first zone and a second zone, the first zone including at least one of immobilized antigens corresponding to the target analyte or immobilized antibodies corresponding to the target analyte, the porous media to generate a current from the first zone to the second zone when the target analyte is present in a sample, a first electrode in contact with the first zone, and a second electrode in contact with the second zone.

Example 79 includes the device of example 78, wherein the porous media is to be saturated with at least one of an enzyme substrate, a reducing agent, an electron mediator, or a redox-species.

Example 80 includes the device of example 79, wherein the conjugates are capable of mixing with the at least one of the enzyme substrate, the reducing agent, the electron mediator, or the redox-species to generate the current.

Example 81 includes the device of example 78, wherein the porous media forms a bioelectrochemical cell.

Example 82 includes the device of example 78, further including a wireless chip coupled to the first electrode and the second electrode.

Example 83 includes the device of example 82, wherein the wireless chip is to sense the current between the first electrode and the second electrode to identify whether the target analyte is present in the sample.

Example 84 includes the device of example 81, further including a sensor to determine a result based on the current from the first and second electrodes, the result indicative of the target analyte being present in the sample, and the wireless chip to wirelessly transmit the result to a reader.

Example 85 includes the device of example 84, wherein the reader is a smart phone application.

Example 86 includes the device of example 78, wherein the porous media is compartmentless.

Example 87 includes the device of example 78, wherein a reaction is to occur on the porous media resulting in a generation of hydrogen peroxide, and wherein at least one of the first electrode of the second electrode made of at least one of copper or screen printed carbon doped with ferrocyanide, the at least one of the copper or screen printed carbon doped with ferrocyanide to oxidize and the hydrogen peroxide to reduce, resulting in a release of an electron corresponding to the current.

Example 88 includes a system comprising a non-visual indicating biosensor device to transmit a test result when an electromagnetic field is sensed, and a reader to generate the electromagnetic field, and obtain the test result.

Example 89 includes the system of example 88, wherein the non-visual indicating biosensor device includes a bioelectrochemical cell to generate a current when a target analyte is present in a sample.

Example 90 includes the system of example 88, wherein the non-visual indicating biosensor device generates the test result based on a current between a first part of a bioelectrochemical cell and a second part of the bioelectrochemical cell, the bioelectrochemical cell included in the non-visual indicating biosensor device.

Example 91 includes the system of example 88, wherein the non-visual indicating biosensor device includes a porous media with a first zone and a second zone, the test result based on a current between the first zone and the second zone.

Example 92 includes the system of example 88, wherein the non-visual indicating biosensor device includes a porous media with a test zone, the non-visual indicating biosensor device to determine the test result based on a current through the test zone.

Example 93 includes the system of example 88, wherein the reader is a smartphone.

Example 94 includes the system of example 88, wherein the reader is to transmit the test result to an external database.

Example 95 includes a non-visual indicating biosensor device for use with a fluid sample, the non-visual indicating biosensor device comprising a lateral flow test strip to conduct a test for a target analyte in a sample, and an antenna to sense an electromagnetic field from an external device, the electromagnetic field to induce a current in the biosensor device to operate the test, and transmit the test result to the external device.

Example 96 includes the device of example 95, wherein the lateral flow test strip includes a bioelectrochemical cell to generate a current when the target analyte is present in the sample.

Example 97 includes the device of example 96, wherein the current is between a first part of the bioelectrochemical cell and a second part of the bioelectrochemical cell.

Example 98 includes the device of example 95, wherein the lateral flow test strip includes a porous media with a first zone and a second zone, the test result based on a current between the first zone and the second zone.

Example 99 includes the device of example 95, wherein the lateral flow test strip includes a porous media with a test zone, the test result based on a current through the test zone.

Example 100 includes a system comprising a non-visual indicating biosensor device to transmit a result of a test, and a reader to time the test, and obtain the result of the test after a period of time from an initiation of the test.

Example 101 includes the system of example 100, wherein the non-visual indicating biosensor device includes a timer to initiate when the test is initiated.

Example 102 includes the system of example 100, wherein the non-visual indicating biosensor device is to transmit at least one of (a) an initiation time corresponding to the initiation of the test or (b) a time indicated by the timer to the reader.

Example 103 includes the system of example 102, wherein the reader is to display at least one of the initiation time, the time indicated by the timer, or an amount of time before the test is complete.

Example 104 includes the system of example 101, wherein the test is initiated when a wireless chip of the non-visual indicating biosensor device receives power.

Example 105 includes a biosensor for providing a diagnostic result, the biosensor comprising a region for receiving a biological sample to be tested, a test region that generates an electrical current in a circuit when target analyte is present in the biological sample, and an antenna to wirelessly transmit information associated with the target analyte if presented to a reader, wherein the biosensor is powered by a bioelectrochemical cell in contact with the test region.

Example 106 includes the biosensor of example 105, wherein molecules in the test region are to react with molecules of the bioelectrochemical cell to generate the electrical current.

Example 107 includes the biosensor of example 105, further including a chip to measure an electromotoric force corresponding to the electrical current, and generate the information associated with the target analyte based on the current.

Example 108 includes the biosensor of example 107, wherein the electromotoric force is to power the biosensor.

Example 109 includes the biosensor of example 105, wherein the antenna is to sense a magnetic field of the reader.

Example 110 includes a biosensor for providing a diagnostic result, the biosensor comprising a region for receiving a biological sample to be tested, a test region that generates an electrical current in a circuit when target analyte is present in the biological sample, and an antenna to wirelessly transmit information associated with the target analyte if presented to a reader, wherein the antenna is powered by a magnetic field generated by the reader.

Example 111 includes the biosensor of example 110, wherein molecules on the test region are to react with molecules of a bioelectrochemical cell to generate the electrical current.

Example 112 includes the biosensor of example 108, further including a chip to measure an electromotoric force corresponding to the electrical current, and generate the information associated with the target analyte based on the current.

Example 113 includes the biosensor of example 112, wherein the electromotoric force is to power the biosensor.

Example 114 includes the biosensor of example 110, wherein the antenna is to sense the magnetic field of the reader.

Example 115 includes an apparatus comprising a front end to connect to one or more electrodes of a biosensor on a lateral flow immunoassay device to obtain one or more signals from the one or more electrodes, and a wireless chip to obtain the one or more signals from the front end, determine results of a test based on whether one or more target analytes are present in a sample based on the obtained one or more signals, and wirelessly transmit the results to a computing device.

Example 116 includes the apparatus of example 115, wherein the front end includes a first front end input to obtain a first signal of the one or more signals from a first electrode of the one or more electrodes, a second front end input to obtain a second signal of the one or more signals from a second electrode of the one or more electrodes, and an output to output at least one of the first signal or the second signal based on instructions from the wireless chip.

Example 117 includes the apparatus of example 116, wherein the wireless chip includes a first chip input to obtain the output of the front end, the wireless chip to compare the output of the front end to a first signal strength threshold, and a second chip input to obtain the output of the front end, the wireless chip to compare the output of the front end to a second signal strength threshold.

Example 118 includes the apparatus of example 115, wherein the wireless chip includes a first chip input and a second chip input, and the front end includes a front end input to connect to one of the one or more electrodes to obtain one of the one or more signals based on an instruction from the wireless chip, and a front end output to transmit the obtained signal of the one or more signals to one of the first input or the second input of the wireless chip based on the instruction from the wireless chip.

Example 119 includes the apparatus of example 115, wherein the wireless chip includes a first chip input and a second chip input, and the front end includes a first channel to connect a first electrode of the one or more electrodes to the first input of the wireless chip, and a second channel to connect a second electrode of the one or more electrodes to the second input of the wireless chip.

Example 120 includes an apparatus for use with a fluid sample, the apparatus comprising a porous media, a wicking pad in contact with the porous media, and a switch including a flow arrestor to at least one of compress or shear the porous media to at least one of reduce or stop flow of liquid toward the wicking pad.

Example 121 includes the apparatus of example 120, wherein the switch moves from a first position to a second position to at least one of compress or shear the porous media.

Example 122 includes the apparatus of example 121, further including an electrode, the switch to cause the electrode to contact the porous media while the switch is in the second position.

Example 123 includes the apparatus of example 121, wherein the switch is spaced a first distance from the porous media in the first position and spaced a second distance from the porous media in the second position, the second distance less than the first distance.

Example 124 includes the apparatus of example 120, further including a holding component including a liquid buffer.

Example 125 includes the apparatus of example 124, wherein the switch causes the holding component to release the liquid buffer onto the porous media.

Example 126 includes a lateral flow assay device comprising a conjugate pad including conjugates corresponding to a target analyte in a biological sample, the conjugates labeled with an enzyme, a porous media including a first zone and a second zone, the first zone including at least one of immobilized antigens corresponding to the target analyte or immobilized antibodies corresponding to the target analyte, the second zone laterally displaced from the first zone along a longitudinal axis of the lateral flow assay device, the porous media to propagate a flow of the biological sample, the conjugates with the enzyme, and a liquid buffer along the porous media, and a first electrode to contact the porous media in the first zone, a second electrode to contact the porous media in the second zone, the first and second electrodes to detect an electrical signal when the target analyte is present in the biological sample and the enzyme reacts with the liquid buffer, and a positionable flow arrestor to impede the flow in the second zone.

Example 127 includes the lateral flow assay device of example 126, further including a wicking pad coupled to the porous media, wherein the flow arrestor is to at least one of compress or shear the porous media to at least one of reduce or stop the flow toward the wicking pad.

Example 128 includes the lateral flow assay device of example 127, wherein the flow arrestor includes a switch that is movable from a first position to a second position to at least one of compress or shear the porous media.

Example 129 includes the lateral flow assay device of example 128, wherein movement of the switch to the second position causes the first electrode and the second electrode to contact the porous media.

Example 130 includes the lateral flow assay device of example 128, wherein the switch is spaced a first distance from the porous media in the first position and spaced a second distance from the porous media in the second position, the second distance less than the first distance.

Example 131 includes the lateral flow assay device of example 128, further including a circuit board, the first electrode and the second electrode coupled to the circuit board, the switch to move at least a portion of the circuit board proximate to the porous media.

Example 132 includes the lateral flow assay device of example 131, wherein the circuit board is pivotable, the switch to pivot the circuit board when the switch is moved.

Example 133 includes the lateral flow assay device of any of examples 127-132, wherein the flow arrestor includes a first flow arrestor and a second flow arrestor.

Example 134 includes the lateral flow assay device of example 133, wherein the first flow arrestor is to at least one of compress or shear the porous media in the first zone and the second flow arrestor is to at least one of compress or shear the porous media in the second zone.

Example 135 includes the lateral flow assay device of example 134, wherein the first electrode and the second electrode are positioned between the first flow arrestor and the second flow arrestor.

Example 136 includes the lateral flow assay device of any of examples 126-135, wherein the flow arrestor includes a chemical substance that is to form a barrier when wetted.

Example 137 includes the lateral flow assay device of any of examples 126-136, further including an antenna in circuit with the first electrode and the second electrode, the antenna to transmit a wireless signal representative of the electrical signal to an external device.

Example 138 includes the lateral assay device of any of examples 126-137, further including an antenna in circuit with the first electrode and the second electrode, the antenna is to receive a power signal from the external device, a sensor to measure at least one of a voltage or a current between the first electrode and the second electrode, the sensor operable based on the power signal, the at least one of the voltage or the current being the electrical signal, and a processor operable based on the power signal, the processor to compare the at least one of the voltage or the current to a threshold, and when the at least one of the voltage or the current is more than the threshold, identify that the target analyte is present in the biological sample, the antenna to wirelessly transmit results to the external device.

Example 139 includes the lateral assay device of any of examples 126-138, wherein the electrical signal is generated by an enzymatic reaction.

Example 140 includes the lateral assay device of any of examples 126-139, wherein the lateral assay device is batteryless.

Example 141 includes an apparatus for use with a fluid sample, the apparatus comprising a porous media, a wicking pad in contact with the porous media, and a switch including a flow arrestor to at least one of compress or shear the porous media to at least one of reduce or stop flow of liquid toward the wicking pad.

Example 142 includes the apparatus of example 141, wherein the switch is moveable between a first position and a second position to at least one of compress or shear the porous media.

Example 143 includes the apparatus of example 142, further including an electrode, the switch to cause the electrode to contact the porous media while the switch is in the second position.

Example 144 includes the apparatus of examples 142 or 143, wherein the switch is spaced a first distance from the porous media in the first position and spaced a second distance from the porous media in the second position, the second distance less than the first distance.

Example 145 includes the apparatus of any of examples 141-144, further including a reservoir including a liquid buffer, the switch to cause the reservoir to release the liquid buffer onto the porous media.

Example 146 includes the apparatus of any of examples 141-145, wherein the flow arrestor is to shear the porous media by cutting a portion of a depth of the porous media.

Example 147 includes a non-visual indicating biosensor comprising a conjugate pad including conjugates to attach to a target analyte in a biological sample, the conjugates labeled with an enzyme, a porous media having a first end and a second end, the conjugate pad coupled to a first end of the porous media, at least one of immobilized antigens corresponding to the target analyte or immobilized antibodies corresponding to the target analyte coupled to porous media between the first end and the second end, the porous media implementing a bioelectrochemical cell between the first end and the second end downstream from the at least one of immobilized antigens or immobilized antibodies, the bioelectrochemical cell to generate an electrical signal based on a reaction between a buffer and the enzyme when the target analyte is present in the biological sample, a wicking pad to draw fluid along the porous media, and an antenna to generate a wireless signal to communicate a presence of the electrical signal.

Example 148 includes the non-visual indicating biosensor of example 147, further a circuit board selectively engageable with the porous media, the circuit board including a first electrode, and a second electrode downstream from the first electrode, the electrical signal generated based on at least one of a voltage differential between the first electrode and the second electrode or a current between the first electrode and the second electrode.

Example 149 includes the non-visual indicating biosensor of example 148, further including a processor to compare a magnitude of the voltage differential or the current to a threshold, and identify that the target analyte is present in the biological sample when the magnitude satisfies the threshold.

Example 150 includes the non-visual indicating biosensor of example 149, wherein the antenna is to receive a power signal to operate the antenna and the processor.

Example 151 includes the non-visual indicating biosensor of any of examples 147-150, further including a switch moveable between a first position and a second position, wherein movement of the switch from the first position to the second position changes the non-visual indicating biosensor from a first operating mode to a second operating mode.

Example 152 includes the non-visual indicating biosensor of example 151, wherein the switch includes a flow arrestor to at least one of cut or compress the porous media when the switch is in the second position, liquid flowable to the wicking pad in the first operating mode, and liquid flow arrested in the second operating mode.

Example 153 includes the non-visual indicating biosensor of examples 151 or 152, wherein an electrode moves from a disengagement with the porous media to engagement with the porous media as the switch moves from the first position to the second position.

Example 154 includes the non-visual indicating biosensor of any of examples 147-153, wherein the antenna is to sense a first electromagnetic field from an external device at a first time, provide identification data of the non-visual indicating biosensor to the external device in response to sensing the first electromagnetic field, sense a second electromagnetic field from the external device at a second time, and provide the wireless signal to communicate the presence of the electrical signal to the external device in response to sensing the second electromagnetic field.

Example 155 includes the non-visual indicating biosensor of example 154, wherein the antenna is to sense a third electromagnetic field from the external device at a third time, the third time between the first time and the second time, and provide the identification data to the external device in response to sensing the third electromagnetic field.

Example 156 includes the non-visual indicating biosensor of examples 147 or 151-155, wherein the antenna is to provide a signal corresponding to at least one of a voltage or a current generated at the porous media, the at least one of the voltage of the current caused by an enzymatic reaction between the enzyme and the buffer.

Example 157 includes At least one non-transitory computer readable medium comprising instructions that, when executed, cause one or more processors to at least access identification information received from a lateral flow assay device at a first time, implement a counter to monitor a first time period and a second time period, the first time period and the second time period based on the identification information, order a change from a first operating mode of the lateral flow assay device to a second operating mode of the lateral flow assay device after the first time period and for the second time period, access at least one of a voltage value or a current value received from the lateral flow assay device via a near field communication (NFC) at a second time, the second time after the second time period, perform a comparison of the voltage value or the current value to a threshold, the threshold based on the identification information, and identify a diagnostic test result based on the comparison.

Example 158 includes the at least one non-transitory computer readable medium of example 157, wherein the instructions cause the one or more processors to determine a geolocation of the lateral flow assay device, and tag the geolocation of the lateral flow assay device with the diagnostic test result.

Example 159 includes the at least one non-transitory computer readable medium of example 157, wherein the lateral flow assay device is a first lateral flow assay device, the identification information is first identification information, the voltage value is a first voltage value, the current value is a first current value, the comparison is a first comparison, the threshold is a first threshold, and the diagnostic test result is a first diagnostic test result, the instructions to cause the one or more processors to access second identification information received from a second lateral flow assay device via the NFC at a third time, use the counter to monitor a third time period and a fourth time period, the third time period and the fourth time period based on the second identification information, order a change from a first operating mode of the second lateral flow assay device to a second operating mode of the second lateral flow assay device after the third time period and for the fourth time period, access at least one of a second voltage value or a second current value received from the second lateral flow assay device via the NFC at a fourth time, the fourth time after the fourth time period, perform a second comparison of the second voltage value or the second current value to a second threshold, the second threshold based on the second identification information, and identify a second diagnostic test result based on the second comparison.

Example 160 includes the at least one non-transitory computer readable medium of example 159, wherein one or more of (1) the third time period at least partially overlaps with one or more of the first time period or the second time period, or (2) the fourth time period at least partially overlaps with one or more of the first time period or the second time period.

Example 161 includes the at least one non-transitory computer readable medium of example 157, wherein the identification information is first identification information and the lateral flow assay device is a first lateral flow assay device, the instructions to cause the one or more processors to prior to the ordering of the change from the first operating mode to the second operating mode, access second identification information received from a second lateral flow assay device via the near field communication (NFC) at third first time after the first time and before the second time.

Example 162 includes the at least one non-transitory computer readable medium of example 161, wherein the instructions cause the one or more processors to, when the first identification information matches the second identification information, order the change from the first operating mode to the second operating mode, the first lateral flow device being the second lateral flow device.

Example 163 includes the at least one non-transitory computer readable medium of example 161, wherein when the first identification information does not match the second identification information, the instructions cause the one or more processors to display an indication that the second lateral flow device is not the first lateral flow device, and prompt a user to scan the first lateral flow device via the NFC.

Example 164 includes the at least one non-transitory computer readable medium of example 157, wherein the identification information is first identification information, the instructions to cause the one or more processors to, when second identification information that matches the first identification information has not been obtained from the lateral flow assay device within the first time period, tag the diagnostic test result as void.

Example 165 includes the at least one non-transitory computer readable medium of example 157, wherein the instructions cause the one or more processors to tag the diagnostic test result as void when a confirmation of the change from the first operating mode to the second operating mode has not been obtained within the second time period.

Example 166 includes the at least one non-transitory computer readable medium of any of examples 157-165, wherein the at least one of the voltage or the current is wirelessly detected by the NFC.

Example 167 includes the at least one non-transitory computer readable medium of example 157, wherein the instructions cause the one or more processors to wirelessly transmit the diagnostic test result and corresponding patient data to at least one of a remote database or a remote server.

Example 168 includes At least one non-transitory computer readable medium comprising instructions that, when executed, cause one or more processors to at least access first identification information received from a lateral flow assay device via a near field communication (NFC) scan at a first time, implement a counter to monitor a first time period, the first time period based on the identification information, before the first time period ends, access second identification information via a second NFC scan at a second time after the first time, compare the first identification information to the second identification information, when the first identification information matches the second identification information, access at least one of a voltage value or a current value received from the lateral flow assay device via a third NFC scan at a third time, the third time after the second time, and identify a diagnostic test result based on the at least one of the voltage value of the current value.

Example 169 includes At least one non-transitory computer readable medium comprising instructions that, when executed, cause one or more processors to at least access identification information corresponding to a lateral flow assay device, implement a counter to monitor a time period, instruct a user to scan the lateral flow assay using a near field communication (NFC) after the time period, access at least one of a voltage value or a current value received from the lateral flow assay device via the scan, perform a comparison of the voltage value or the current value to a threshold, the threshold based on the identification information, and determine a diagnostic test result based on the comparison.

Example 170 includes the at least one non-transitory computer readable medium of example 169, wherein the instructions cause the one or more processors to guide the user to apply at least one of a sample or a buffer to the lateral flow assay device, and implement the counter after the user has confirmed that the at least one of the sample or the buffer was applied.

Example 171 includes the at least one non-transitory computer readable medium of example 169, wherein the instructions cause the one or more processors to instruct the user to scan the lateral flow assay using the NFC to obtain the identification information.

Example 172 includes the at least one non-transitory computer readable medium of example 169, wherein the instructions cause the one or more processors to instruct a user to scan the lateral flow assay using the NFC at a time prior to the access of the at least one of the voltage value or the current value.

Example 173 includes the at least one non-transitory computer readable medium of example 172, wherein the identification information is first identification information, the instruction to cause the one or more processors to access second identification information via the NFC in response to the scan at the second time, compare the second identification information to the first identification information, and alert a user to an error when the second identification does not match the first identification information.

Example 174 includes a method for determining a presence or absence of a target analyte in a biological sample, the method comprising instructing a user via an interface of a user device to apply the biological sample to a lateral flow device, generating, by executing instructions with a processor of the user device, a test result by determining whether the target analyte is present in the biological sample based on an electrical signal wirelessly received from the lateral flow device, and transmitting, from the user device, the test result to at least one of an external server or an external database.

Example 175 includes the method of example 174, wherein the electrical signal corresponds to an enzymatic reaction on the lateral flow device.

Example 176 includes the method of example 174, further including instructing the user via the interface to take an action to arrest flow on the lateral flow device.

Example 177 includes the method of example 176, wherein arresting the flow strengthens the electrical signal.

Example 178 includes the method of example 176, further including implementing a timer via the user device, wherein the instructing of the user to take the action to arrest flow is based on an output of the timer.

Example 179 includes the method of example 174, wherein the generating the test result includes comparing, by executing instructions with the processor, the electrical signal to a threshold, the electrical signal being at least one of a voltage or a current generated at a porous membrane of the lateral flow device.

Example 180 includes the method of example 174, further including preventing display the test results on the interface of the user device to preserve privacy of a patient.

Example 181 includes the method of example 174, further including obtaining, by executing instructions with the processor, a first identifier from the lateral flow device at a first time prior to instructing the user to apply the biological sample and obtaining, by executing instructions with the processor, a second identifier from the lateral flow device prior to obtaining the electrical signal.

Example 182 includes the method of example 181, further including identifying, by executing instructions with the processor, an algorithm based on the first identifier, the determining whether the target analyte is present in the biological sample being based on the algorithm.

Example 183 includes the method of example 181, further including validating, by executing instructions with the processor, that the electrical signal corresponds to the lateral flow device when the first identifier matches the second identifier.

Example 184 includes the method of example 174, wherein the transmitting of the test result includes transmitting the test result in conjunction with patient information and geolocation information.

The disclosed methods, apparatus and articles of manufacture improve the efficiency of determining results of the machine readable diagnostic test. To reduce and/or otherwise eliminate environment light issues, examples disclosed herein provide a machine readable diagnostic that can be read with a smartphone as opposed to visually. The disclosed methods, apparatus and articles of manufacture are accordingly directed to one or more improvement(s) in the functioning of a diagnostic test and diagnostic readers.

In addition, as discussed above, visual interpretation of test results is prone to operator subjectivity and error. More accurate and objective results can be obtained with the electrical-based examples disclosed herein. Examples disclosed herein include a LFA device that generates an electrical signal (e.g., a current, a voltage, etc.) using various techniques (e.g., a bioelectrochemical cell technique, a circuit completion technique, etc.) that corresponds to a test results. The electrical signal can be measured and wirelessly provided to a reader without a battery device included in the LFA device. In some examples, the LFA device can determine the test result based on the electrical signal and transmit the result to the reader. The reader can obtain the test result and/or process the electrical signal to determine a test result distribute the test result to an external server or database (e.g., via the reader) to provide near real-time data corresponding to disease and/or the spread of a disease.

Further, examples disclosed herein provide a mechanism for arresting flow and/or positioning electrodes on the LFA device to obtain a stronger electrical signal that is able to be measured for a longer duration for time than other diagnostic tests. The examples disclosed herein also enable multiplexing where multiple lines may be used to detect multiple marks (e.g., multiple types of antibodies/antigens) based on one sample that would be difficult or impossible to decern with the human eye. Multiplexing has applications, for example, in a single diagnostic test that could test for multiple types of venereal diseases.

The example controls disclosed herein also control the run time of the diagnostic tests to ensure that an operator does not attempt to obtain results too soon (i.e., before the test is complete), obtain results too late, arrest flow too soon, arrest flow too late, etc. This provides further error proofing in obtaining accurate testing results. Additionally, the example controls facilitate multiple scans to (a) identify the LFA device, (b) verify that the test being read corresponds to the test that is supposed to be read (e.g., when performing multiple tests on different LFAs in parallel using a single reader), and (c) obtain electrical signals corresponding to the test results. This provide further error proofing in obtaining multiple tests with overlapping read windows to ensure that the wrong test is not read.

Examples disclosed herein also include additional information (lot number, expiration date, expiry date, test information, signal quality information, chain of custody, etc.) with the tests results, which can all be transferred together with the NFC technology. Traditional methods use additional readers such as, for example, a bar code reader to read information about a test, which would be in additional to an optical reader that determines/interprets the test results. Thus, the disclosed examples reduce the number of readers needed to obtain a greater amount of information.

Also, the example rapid diagnostic testing using the electronic-based approach have higher sensitivity than conventional, visually read tests. In the examples disclosed herein, a lower detection threshold is possible using the electronic-based technology than can be employed when the results are based on the visual interpretation of an operator.

The examples disclosed herein may include NFC chips that can be encoded an encrypted. The associated tests and manufacturing specific data can subsequently be re-coded if adjustments are made to the product labelling data including, for example, to extend shelf-life and/or if other retrofitting is desired. In some examples, the encoding and/or encryption can be updated and/or configured remotely.

Descriptors "first," "second," "third," etc. are used herein when identifying multiple elements or components which may be referred to separately. Unless otherwise specified or understood based on their context of use, such descriptors are not intended to impute any meaning of priority, physical order or arrangement in a list, or ordering in time but are merely used as labels for referring to multiple elements or components separately for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for ease of referencing multiple elements or components.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, and (3) at least one A and at least one B.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The following claims are hereby incorporated into this Detailed Description by this reference, with each claim standing on its own as a separate embodiment of the present disclosure.

What is claimed is:

1. A lateral flow assay device comprising:

a conjugate pad including conjugates corresponding to a target analyte in a biological sample, the conjugates labeled with an enzyme;

a porous media including a first zone and a second zone, the first zone including at least one of immobilized antigens corresponding to the target analyte or immobilized antibodies corresponding to the target analyte, the second zone laterally displaced from the first zone along a longitudinal axis of the lateral flow assay device, the porous media structured to propagate a flow of the biological sample, the conjugates with the enzyme, and a liquid buffer along the porous media;

a first electrode operable to contact the porous media in the first zone;

a second electrode operable to contact the porous media in the second zone, the first and second electrodes structured to detect an electrical signal when the target analyte is present in the biological sample and the enzyme reacts with enzyme substrates in the liquid buffer; and a first flow arrestor and a second flow arrestor, the first flow arrestor to, when deployed, at least one of compress or shear the porous media in the first zone, the second flow arrestor to, when deployed, at least one of compress or shear the porous media in the second zone to impede the flow in the second zone, the first electrode and the second electrode positioned between the first flow arrestor and the second flow arrestor.

2. The lateral flow assay device of claim 1, further including a wicking pad coupled to the porous media, wherein at least one of the first flow arrestor or the second flow arrestor is to at least one of compress or shear the porous media to at least one of reduce or stop the flow toward the wicking pad.

3. The lateral flow assay device of claim 2, wherein at least one of the first flow arrestor or the second flow arrestor includes a switch that is movable from a first position to a second position to at least one of compress or shear the porous media.

4. The lateral flow assay device of claim 3, wherein movement of the switch to the second position causes the first electrode and the second electrode to contact the porous media.

5. The lateral flow assay device of claim 3, wherein the switch is spaced a first distance from the porous media in the first position and spaced a second distance from the porous media in the second position, the second distance less than the first distance.

6. The lateral flow assay device of claim 3, further including a circuit board, the first electrode and the second electrode coupled to the circuit board, the switch to move at least a portion of the circuit board proximate to the porous media, wherein the circuit board is pivotable, the switch to pivot the circuit board when the switch is moved.

7. The lateral flow assay device of claim 1, including a chemical substance that is to form a barrier when wetted.

8. The lateral flow assay device of claim 1, further including an antenna in circuit with the first electrode and the second electrode, the antenna to transmit a wireless signal representative of the electrical signal to an external device.

9. The lateral flow assay device of claim 1, further including:

an antenna in circuit with the first electrode and the second electrode, the antenna is to receive a power signal from an external device;

a sensor to measure at least one of a voltage or a current between the first electrode and the second electrode, the sensor operable based on the power signal, the at least one of the voltage or the current being the electrical signal; and a processor operable based on the power signal, the processor to:

compare the at least one of the voltage or the current to a threshold; and when the at least one of the voltage or the current is more than the threshold, identify that the target analyte is present in the biological sample, the antenna to wirelessly transmit results to the external device.

10. The lateral flow assay device of claim 1, wherein the electrical signal is generated by an enzymatic reaction.

11. The lateral flow assay device of claim 1, wherein the lateral flow assay device is batteryless.

12. The lateral flow assay device of claim 3, further including a reservoir including a liquid buffer, the switch to cause the reservoir to release the liquid buffer onto the porous media.

13. The lateral flow assay device of claim 3, wherein at least one of the first flow arrestor or the second flow arrestor is to shear the porous media by cutting a portion of a depth of the porous media.

14. The lateral flow assay device of claim 1, wherein at least one of the first flow arrestor or the second flow arrestor is to impede the flow in the second zone by cutting a portion of a depth of the porous media.

15. The lateral flow assay device of claim 1, further including a reservoir including a liquid buffer for release onto the porous media.

16. The lateral flow assay device of claim 1, further including an antenna to:

sense a first electromagnetic field from an external device at a first time;

provide identification data of the lateral flow assay device the external device in response to sensing the first electromagnetic field;

sense a second electromagnetic field from the external device at a second time;

provide a wireless signal to communicate a presence of the electrical signal to the external device in response to sensing the second electromagnetic field;

sense a third electromagnetic field from the external device at a third time, the third time between the first time and the second time; and provide the identification data to the external device in response to sensing the third electromagnetic field.

17. The lateral flow assay device of claim 1, further including an antenna to provide a signal corresponding to at least one of a voltage or a current generated at the porous media, the at least one of the voltage or the current caused by an enzymatic reaction between the enzyme and the liquid buffer.

* * * * *